(12) United States Patent
Fried

(10) Patent No.: US 7,957,132 B2
(45) Date of Patent: Jun. 7, 2011

(54) EFFICIENTLY COOL DATA CENTERS AND ELECTRONIC ENCLOSURES USING LOOP HEAT PIPES

(76) Inventor: Stephen S. Fried, Kingston, MA (US)

( * ) Notice: Subject to any disclaimer, the term of this patent is extended or adjusted under 35 U.S.C. 154(b) by 140 days.

(21) Appl. No.: 12/103,695

(22) Filed: Apr. 15, 2008

(65) Prior Publication Data

US 2008/0259566 A1 Oct. 23, 2008

Related U.S. Application Data

(60) Provisional application No. 60/923,588, filed on Apr. 16, 2007.

(51) Int. Cl.
G06F 1/20 (2006.01)
H05K 7/20 (2006.01)

(52) U.S. Cl. ......... 361/679.47; 361/679.48; 361/679.54; 361/694; 361/695; 361/697; 361/700; 361/702; 361/704; 361/719; 165/80.2; 165/185

(58) Field of Classification Search .......... 361/679.47–679.48, 679.51–679.54, 361/694–704, 715, 719; 165/80.2–80.5, 165/104.33, 185
See application file for complete search history.

(56) References Cited

U.S. PATENT DOCUMENTS

| | | | | | |
|---|---|---|---|---|---|
| 5,203,399 | A * | 4/1993 | Koizumi | .................. | 165/104.33 |
| 5,998,863 | A * | 12/1999 | Kobayashi et al. | ........... | 257/715 |
| 6,643,132 | B2 * | 11/2003 | Faneuf et al. | ................. | 361/700 |
| 6,657,121 | B2 * | 12/2003 | Garner | ......................... | 174/16.3 |
| 6,693,797 | B2 * | 2/2004 | Faneuf et al. | ................. | 361/689 |
| 6,789,611 | B1 * | 9/2004 | Li | ............................ | 165/104.29 |
| 6,796,372 | B2 * | 9/2004 | Bear | ....................... | 165/104.21 |
| 6,829,142 | B2 * | 12/2004 | Belady et al. | ............ | 361/679.47 |
| 6,840,304 | B1 * | 1/2005 | Kobayashi et al. | .......... | 165/11.1 |
| 6,967,841 | B1 * | 11/2005 | Chu et al. | ....................... | 361/700 |
| 6,972,365 | B2 * | 12/2005 | Garner | ......................... | 174/16.3 |
| 6,981,543 | B2 * | 1/2006 | Chesser et al. | ........... | 165/104.26 |
| 7,068,509 | B2 * | 6/2006 | Bash et al. | ..................... | 361/700 |
| 7,071,408 | B2 * | 7/2006 | Garner | ......................... | 174/16.3 |
| 7,133,283 | B2 * | 11/2006 | Faneuf et al. | ................. | 361/689 |
| 7,203,063 | B2 * | 4/2007 | Bash et al. | ..................... | 361/699 |
| 7,233,491 | B2 * | 6/2007 | Faneuf et al. | ................. | 361/689 |
| 7,380,585 | B2 * | 6/2008 | Liu et al. | .................. | 165/104.33 |
| 7,403,384 | B2 * | 7/2008 | Pflueger | ....................... | 361/688 |
| 7,539,020 | B2 * | 5/2009 | Chow et al. | ................... | 361/726 |
| 7,599,184 | B2 * | 10/2009 | Upadhya et al. | ............. | 361/699 |
| 7,650,932 | B2 * | 1/2010 | Li | ............................. | 165/104.33 |
| 7,654,310 | B2 * | 2/2010 | Li | ............................ | 165/104.33 |
| 2006/0113066 | A1 * | 6/2006 | Mongia et al. | ........... | 165/104.33 |

FOREIGN PATENT DOCUMENTS

DE 102008020038 A1 * 11/2009
JP 59029992 A * 2/1984

* cited by examiner

Primary Examiner — Jayprakash N Gandhi
Assistant Examiner — Robert J Hoffberg
(74) Attorney, Agent, or Firm — Michael Ries

(57) ABSTRACT

Disclosed in the present invention are methods for cooling components contained in enclosures that reject 500 or more Watts employing two phase passive heat transfer devices including Loop Heat Pipes and devices we refer to as LHPLs. The methods minimize the amount of energy employed in cooling while at the same time maximizing the quality of heat rejected to the secondary cooling loops that transmit the heat to the outside world. Where data centers provide direct access to chilled water it becomes possible to reject heat directly to cooling towers in locations as hot and humid as Atlanta Ga. eliminating 40% or more of the total energy consumed. The key advances that make this energy efficient performance possible employ LHPLs that have the smallest possible total thermal resistance, methods that maximize their effectiveness and ancillary devices that minimize the energy consumed in cooling with air.

3 Claims, 35 Drawing Sheets

EFFICIENTLY COOL DATA CENTERS AND ELECTRONIC ENCLOSURES USING LOOP HEAT PIPES

This application claims priority to U.S. Provisional Application 60/923,588 filed 04-16-2007, the entire disclosure of which is incorporated by reference.

BACKGROUND

A way and apparatus that may be employed to efficiently cool data centers and electronics housed in enclosures that employs Loop Heat Pipes and other passive technologies to cool the primary heat loads in such systems and which employ a combination of other methods to cool the secondary heat loads.

The cooling of electronics housed in enclosures has for many years been dominated by methods that were more concerned about getting the job done than the energy it took. Methods for improving the efficiency of electronic cooling using passive heat transfer such as heat pipes have been available since the Manhattan project, yet have only become inexpensive with the advent of CPUs that rejected 40 or more Watts, and needed to extend the operating capabilities of finned heat sinks. This disclosure employs passive closed loop heat transfer devices that can dramatically improve not only the energy efficiency of electronic cooling but also makes it possible to cool devices that reject 500 or more Watts mounted on densely packed printed circuit boards and in the case of a data centers, reduce the energy required to cool it by 80% or more!

The devices at the heart of this disclosure are Loop Heat Pipes, Capillary Pumped Loops and derivatives of Loop Heat Pipes that include devices like pumps in the condenser lines. We lump all these devices together into the category Loop Heat Pipe Like (LHPL).

In general the LHPLs employed provide the best energy efficiency of any electronic cooling device ever invented. Not only are they passive, but their ability to reject heat to new locations is often measured in meters employing very small condenser pipes (often less than 3 mm) that make it possible for them to move heat out of tight spaces to condensers that can very efficiently reject heat employing heat transfer devices that have large contact areas to secondary coolants such as air and water. LHPLs minimize the energy required to reject energy, but they also maximize the quality of the heat being passed to their secondary coolant streams. It is this second attribute that often just as important as the first, when it comes to producing systems whose overall energy efficiency has been maximized. It is their ability to transport heat to new locations in a chassis or enclosures and then pass it through a reasonably long small pipe to a condenser that distributes it over a reasonably large area, that makes it possible to efficiently transfer the heat being rejected directly to a secondary coolant such as chilled water that results in the high quality heat that make it possible to transport the heat leaving rack mount servers directly to devices cooling towers that make these devices so valuable in data center cooling. The secondary coolants that receive this heat end up with the highest delta T's of any primary heat load rejection technology that we know of.

It is the low total thermal resistances of 0.15° C./Watt and heat transfer coefficient of 0.15° C./(Wcm$^2$) that make this outstanding performance possible. The state of the art Loop Heat Pipes employed in this disclosure employed devices disclosed in the past that people familiar with the art know how to make and were made of Nickel with stainless steel condenser pipes or copper and employed Ammonia and Water working fluids. The evaporators of these devices were only 0.3 inches tall and mounted on the heat spreaders of CPUs were small enough to easily fit on PCBs set on 0.8 inch centers. In the case of a 100 Watt CPU whose LHP condenser was cooled by 30° C. water and whose condenser produced 47° C. water, the CPU being cooled reported a die temperature of just 62° C. Translated into practical terms, employed in the 1 U rack mount chassis that dominate modern data centers, this device makes it possible to remove the heat directly from a server to the data center's cooling tower or other heat sink. In the process, the noisy fans in the racks that add numerous points of failure and consume as much as 30% of the server's power along with the CRAC unit's air blowers and water chillers (that together consume 35% of the data center's total power) can be eliminated! The 30° C. temperature chosen came from the ASHRAE "0.4%" tables for Atlanta Ga. —this was the worst case cooling effluent that could be expected from a commercially available evaporative cooling tower at that location. A quick comparison of the power consumption at institutions like Lawrence Livermore National Labs suggests that:

| | |
|---|---|
| Electronics | 50% |
| Water Chiller | 25% |
| Air Blower | 10% |
| 1U fans | 9% |
| UPS | 5% |
| Lighting | 1% | changes to this:

| | |
|---|---|
| Electronics | 83% |
| 1U fans | 1.6% |
| Cooling Tower | |
| Pump and fan | 5% |
| UPS | 8.3% |
| Lighting | 1.6% |

Which is to say the total power consumed by the data center goes down by 40%!

The same energy benefits that accrue to data center cooling also accrue to the general cooling of all electronic enclosures that are air cooled, but to a lesser extent, for the simple reason that air is a much poorer heat transport medium than the chilled water. At the head of the list of benefits in addition to reduced energy costs are huge reductions in noise, the elimination of heat arriving at the walls of enclosures that can be so hot that it is almost possible to get burned touching them, the frequent failure of rotating cooling components including fans and pumps (in the case of pumped liquid cooling) which now occur so often that the systems that employ them have to mount them so that they can be easily swapped out without turning the machine off along with the ability to reject heat loads from devices that produced 500 or more Watts and to cool efficient devices such as CPUs and GPUs mounted in laptops where improved energy efficiency can improve battery life.

To appreciate the benefits of employing LHPLs to cool electronic enclosures, including air and water cooled electronic devices used to do everything from space vehicles to the rejection of heat to the cooling towers of data centers, it is first necessary to consider the goals of this disclosure. These are to efficiently cool electronic enclosures that contain semiconductor devices that may reject 200 or more Watts in the future and often end up being mounted on densely packed PCBs along with the devices that support them and reject much less heat. And, to carry out this task while maximizing the quality of the heat being rejected to the cooling systems providing the coolants being employed, as much as possible. In the case of air cooled enclosures housed in rack mounted chassis, we wanted to make both efficiency and maximization of heat quality achievable at the same time which can dramatically reduce the cost of cooling serves that continue to be housed in air cooled data centers. In cases where liquid cooling including chilled water is available, our goal was to reject high quality heat all the way back to the data center cooling tower, on a year round basis in most localities in the world. To achieve these goals, we employed LHPLs, some of whose other outstanding properties ignoring the fact they consume no energy turns out to be that they eliminate most of the electric motors, fans, blowers, compressors and other rotating devices found in servers and throughout the data center that end up making noise, contribute to frequent server failures and cost money to maintain and operate.

These goals don't get met without skepticism from practitioners of the art that employ alternative and competitive technologies, so we will now address the advantages of our approach in detail, while at the same time laying out the critical items that need to be overcome to reach our goals.

There are a large number of inventions that have been recently been investigated whose main purpose has been to improve the heat transfer capabilities of devices that can be used to cool semiconductor devices that reject large quantities of heat. LHPLs continue to provide as good or better performance as any of these other devices while at the same time reducing total energy expenditures. The highest performance competitors that we are aware of that actually work and compete with passive two phase solutions typically employ sensible cooling, including microchannels and jet impingement both of which employ liquids pumped under pressure. Microchannels drive the liquid across a heat spreader whose contact area with the heat source being rejected is increased using serpentine shaped channels. The porous metallic wicks employed by LHPLs can provide total contact areas between the working fluid and the heat coming into the wick that are thousands of times greater than the cross sectional areas of the dies being cooled. It is difficult to achieve the same surface area ratios using microchannels and at the same time provide uniform cooling across the die. In addition, it is difficult in general for sensibly cooled devices to make up for the 100 to 1 increase in cooling performance per gram of working fluid that phase change technologies provide. The other problem with either approach is that It does not provide the counterflow heat transfer principles that LHPL wicks make possible (i.e. in microchannels the flow is across the die and dies tend to be hot everywhere, whereas the flow in a wick starts at the cold end away from the die and progresses towards it hot end getting hotter as it gets closer to the heat source (uniformly across the die) until the working fluid finally reaches the temperature where it boils, at which point it exits stage right through a channel designed to carry it off leaving the liquid that has not reached boiling behind and not mixing with it: what leaves for the condenser is hot gas and nothing but hot gas.

Jet impingement technology on the other hand ought to provide uniform cooling but suffers from another problem, which is mixing of hot and cold liquid in the cavity where the heat exchange between the die (or its heat spreader) go on in each of many such cavities. This mixing is an invariable result of the fact that to get good transfer between the surface being cooled and the working fluid turbulent flows need to be employed. The heat transfer coefficients measured using this technique like the former can be very high, simply because they do not take into account the quantity of coolant that needs to be pumped across the processor. In our case, the water flow rate required to transfer 100 Watts turns out to be just 1.2 ml/sec, which is one of the reasons that we frequently measured delta T's as high as 17° C. when cooling with our ideal secondary coolant, water. In either event the two most crucial attributes that get solved by LHPLs when it comes to problem of things like global warming are the efficient removal of energy from the CPUs and the retransmission of this energy to a secondary coolant without making a major reduction of the quality of the heat being rejected by the CPU.

One of the big problems in energy conservation is not understanding the important role that the quality of the heat being rejected to the final cooling device in major thermodynamic systems plays in the overall cost of buying and operating such systems. In the case of studies done for DOE on employing an Ammonia Rankine Bottom Cycle to increase the energy efficiency of a 12 megawatt fuel cell power plant it was discovered that extracting too much energy from the exhaust flow of the fuel cell ended up driving up the cost of the energy required to run the cooling fan in the air cooling tower, limiting the account of energy that could be saved to around 8% but adding a five year payback on the device that improved plants efficiency. The implication for data center cooling is, keep the quality of the heat up, unless you want to spend a lot of money to reject it at the cooling tower. In existing data centers the buck gets passed to the HVAC guys whose job it is to sell uses of large enough water chiller to raise the temperature of the CRAC unit's output so it can drive a cooling tower. This consumes 25% of the total energy budget of the data center.

The naïve approach to the use of passive heat devices suggests that like the extra cooling loops that currently consume close to 35% of the energy required to run a data center, not understanding how to apply them, can result in similar losses. It is quite easy to show, for example, that a sequential series of passive heat transfer devices passes less energy along than a single efficient passive device for the simple reason that energy losses in passive devices are dominated by the thermal resistance at the end points and any sequence of such devices has more such end points. It also turns out that in the case of optimizing the energy consumption of a data center cooling system, the crucial role played by passive devices turns out to be moving the energy as quickly (i.e. using the shortest length of condenser tubing) as possible to the best possible device that can move it the long distance it needs to travel to get to the cooling tower suffering the smallest reductions in heat quality. And the device that does the best job at this last task is called an insulated pipe and what runs down that pipe most often turns out to be water. It turns out moving megawatts of energy from the data center floor to the cooling tower simply is not practical for the same reason that moving the hot air in a data center room back to the cooling tower is not. So by definition one of our ultimate tasks is now well defined, create the LHPLs required to remove the primary heat loads using the most efficient condensers and evaporator to CPU interfaces that can be made, and in the case of a secondary coolant that happens to be chilled water, interface them to this supply using the shortest possible condenser lines so that the temperature of the water being produced is as high as possible. And the secondary task turns out to be, transfer the remainder of the energy in the system to chilled water as well, employing the smallest amount of power.

This last paragraph in a nutshell contains our marching orders. And, the two crucial things that we need to do to carry out this set of commands when it comes to the use of LHPLs, is remove the heat from the die being cooled wasting the smallest amount of heat. And, when the vapor the LHPL has created ends up at a condenser, make sure that the condenser gets its job done wasting the smallest amount of heat while at the same time maximizing the quality of the heat being transferred. The first chore is done using heat spreaders that mate to the CPUs we need to cool and don't waste any heat depositing it in the LHPL's evaporator wick. The second chore is designing condensers that waste as little energy as possible and when it comes time to cool with liquids, employ efficient counter-flow techniques to the problem that maximize the quality of the heat being rejected. While it sounds simple, the majority of the prior art that we have visited ignores the problem of maximizing the quality of the heat, which is not all that surprising, we did as well at the start of our research until we remembered the lessons learned designing fuel cell power plants and figured out how they applied to efficiently rejecting heat in electronics housed in buildings and data centers.

Similar naïve concepts about the best way to employ Loop Heat Pipes and their derivatives to employing air to cool electronic enclosures that contain components rejecting large quantities of heat have also been around for quite some time. The first set of claims in this disclosure apply to air cooled enclosures only and use the concept that the LHPL condensers save the largest amount of energy in an air cooled enclosure when they are placed at points in the enclosure where the cooling air leaves the enclosure. In many instances this turns out to be the spot where the chassis's exhaust cooling fans are located. Placing LHPL condensers at these locations results in a reduction of the ambient temperature of the air in the chassis which in turn reduces the air flow rates needed to cool components cooled by circulating ambient air as well as the elimination of fans on the CPUs and other hot components cooled by the LHPL evaporators. In situations where there are many rows of hot devices the elimination of non-uniform cooling and the attendant reduction in flow speeds is great enough to make it possible for the fans that perform the chassis exhaust cooling to simultaneously cool the LHPL condensers, while at the same time pulling much less total air through the chassis which results in a large reduction in the energy needed to employ air cooling to cool electronics and dramatic reductions in side effects like noise.

While Loop Heat Pipes have been around for many years, the assumption of the people with prior art is simply that just employing passive heat transfer devices must end up reducing the cost of rejecting energy. While this is true, because you are eliminating fans, what they are ignoring is the fact that proper condenser design and placement can often double the energy savings.

It turns out that 30 to 40% of the energy rejected by servers comes from ancillary components, so we will also have to worry about minimizing these energy costs as well. In data centers in which the average rack cabinet only consumed 5 KW, the fans on the rear of rack cabinets were a convenient way to help cool the contents. However, their main function at today's power levels of 20+KW, is mostly to hide the unsightly cables that connect them. A significant portion of the air being drawn through a typical rack cabinet ends up being drawn around the stack of server chassis within it and often the asymmetric flows within the cabinet can result in eddies that circle back to the front of the cabinet near the top, heat up the top servers by as much as 15 degrees F. To get around that problem fans can be added to the top of the rack cabinet and baffles inserted between the servers and the side panels. A better way to employ such fans, is simply to insert a duct in the cabinet that can be used to gather up all the air from the rack mounted chassis and exhaust it out the rear of the cabinet by connecting it the fans on the rear door or out the top using fans mounted on the top panel or possibly to the CRAC units return air flow ducting. To make sure that this duct does what it is intended to do, a mechanism has been provided in the disclosure to seal the chassis to the duct and at the same time make sure that in the event that a chassis is not installed the duct does not leak. Furthermore, to help solve the problem of potential leaks in situations where direct chilled water is being employed within the rack cabinets, the duct can be used to contain the chilled water manifolds that serve the rack mount chassis. Finally, to make it possible for the air being removed from the rack to be reused without having to make the long trip back to the CRAC units blower, simply inserting chilled water air heat exchangers in the exit path from the rack mount chassis to the duct, makes it possible to eject the air from the cabinet at the ambient air temperature of the room. This strategy has a number of benefits that other approaches to the cooling of high power rack mount chassis that employ water cooled air heat exchangers within the rack cabinet do not. Besides taking up much less space in the rack cabinet, and making it possible to employ distributed heat exchangers whose total area is much larger than the ones employed by other solutions, it also reduces the total high speed fetch that the air has to make. And in the process, the amount of energy that gets injected into air flows ends up being minimized.

Reducing the energy employed moving air is one of our overall goals. When we have to do it, our goal is to move the air the smallest distance at the smallest possible speed that gets the cooling job done. The reason for this is quite simple, energy losses due to drag do not scale linearly with velocity, but at a faster rate. Keeping the velocity and distance down, makes an enormous difference in the energy consumed by the fans driving the serves, rack cabinets and the data center itself. This can be simply verified by examining the power required to operate 1 U fans. The earlier devices that turned at 10,500 RPM consumed one to two Watts and provided 12 CFM. The latest fans provide twice the cooling flow rate but consume three to four times as much energy, with the latest motor devices consuming as much as 8 times the power. The technology we employ cuts down on these losses three different ways. First, when exchanging energy between air and either the primary coolant being chilled in a condenser, or a chilled liquid that is cooling it, our methods employ finned condensers that have large areas, which the small size of LHPL evaporators enables by doing things like moving the heat being rejected out of the tight spaces between PCBs where there is no room to place large heat exchangers which in turn ends up reducing the velocity of the air required. Next, by moving air the smallest distances possible. Often this means going to rack mount chassis like 1 U chassis in which the tops and bottoms end up behaving like airflow baffles. While not necessary for our technology to function, the choice of the right chassis architecture can impact the overall efficiency of the cooling being provided. The other technique we employ is to cut down on the distance that air needs to flow at high velocities when it is being employed by enclosures housed in rack cabinets. One of our embodiments employs a negative pressure duct that is sealed to the chassis it is evacuating air out of and which can completely eliminating the need for the air to travel back to the data center's air heat exchanger making large reductions in the amount of energy that needs to employed by air fans and blowers. When compared with other techniques for cooling rack mount chassis housed in rack cabinets this embodiment ends up reducing energy by reducing the distance that the air has to move at high velocities while at the same time eliminating the need in many instances for the use of hot and cold isles. When this embodiment is coupled with the use of liquid cooled air heat exchangers mounted at the exit point of rack mount chassis, it makes it possible for air to simply leave the rack quickly, and then proceed across the isle to the next row of rack cabinet inputs, minimizing the total distance the air needs to be routed through high speed ducts and also reducing things like losses in ducts due to other problems like poor sealing. This strategy plays an important role in our energy conservation effort, and is embodied in both our sealed chassis and sealed duct designs.

The final energy reduction principle that needs to be taken into account that out embodiment improves is water condensation. In some data centers, as much as 40% of the energy being employed by water chillers gets used to remove (by condensation) water vapor from the cooling flow which then, apparently needs to get added back into the flow to keep IT people wandering through the data center happy. It turns out that there no longer is and ESD requirement on the minimum air content of the air being employed in data centers, which basically means that keeping the relative humidity below the point where condensation occurs in the equipment can now be achieved by simply making sure the dew point of the air in the systems being cooled is less than the temperature of the liquid coolant being employed to cool systems, saving roughly 10% of the energy employed to cool some data centers, especially those in humid localities.

Our sealed chassis embodiments make this possible by keeping the dew point of the air inside of the rack mount chassis below the temperature of the coldest liquid coolant employed. This is simply accomplished in an embodiment in which we pass slightly pressurized air through a cold trap that removes excess water from it before slowly bleeding it into the "sealed" chassis, that are allowed to slowly leak air back to the ambient, at a rate that guarantees that the average air content of the chassis remains dry enough to avoid condensing if and when it comes into contact with chilled surfaces.

When it comes to cooling air cooled enclosures in general, LHPLs make it possible to make great strides in efficient uniformly distributed air cooling, by the simple act of placing the LHPL condenser at the point in the chassis where the air flow is normally exhausted out of the chassis. In the two enclosures we have studied, 1 U rack mount chassis and desktop cooled chassis, the fans that are employed on the exterior surfaces of these chassis have provided high enough flow rates to in the case of a 1 U chassis only require a single blower (already employed to pull air out of the chassis) to cool a pair of 120 Watt processors (it normally takes four to eight 1 U fans to accomplish the same task) and a single 120 mm fan running at just 1800 RPM to cool a 500 Watt CPU sitting in either the PCIe bus of the system. In all of the chassis we have examined, including the 4 U chassis employed to cool four to eight Opteron multi-core processors, the existing fans on the rear wall of the chassis that we have examined have more than enough cooling fans to make it possible to cool all of the processors, without the need for CPU fans. Which is to say, all of the chassis tested, when their CPUs were cooled using LHPLs, could get by without the need for CPU cooling fans. Not only that, the CPUs that were being cooling in situations like the 4 P/8 P chassis, normally require very high air flow rates even with cooling fans that fit into 2 U tall spaces simply because the CPUs in the front row end up heating the air used to cool the rear row of processors. This problem goes away with LHPLs, making it possible to actually reduce the air flow rates on the rear wall while at the same time eliminating the four to eight fans typically used to cool processors. And, while we can't claim that air cooling does as good a job as water cooling, we have gone about as far as you can go with air cooling to maintain the quality of the heat being rejected. In addition to providing sealed ducts, more uniform distribution of cooling air across the chassis and the reduction of the ambient temperature within the chassis, we have also introduced LHPL condenser designs which employ counter-flow cooling, which results in increased exit flow air temperatures which in turn end up improving the efficiency of an air cooled data center's water chiller.

As a general principle then, one of our goals is to wherever possible, remove the heat being rejected by the hottest components in an enclosure and then deposit it someplace where it can be ejected to the next cooling loop, which keeps it from circling around and haunting us. The duct above helps make this possible by gathering it up and shipping it off to the next cooling loop. When installed in poorly designed rack cabinets or data center rooms, up to 20% of the heat that is being rejected will often end up congregating in high spots, and then come back to haunt the top most chassis in a rack mount enclosure. The other major problem we face is the secondary components that we have created embodiments to handle, which gather up their heat using the smallest amount of energy.

One major gray area here is DIMM modules which can often reject a surprising amount of heat, that needs to be rejected. Fully buffered DIMM modules can now reject up to 15 Watts each, which means an array of 16 such modules can reject 240 Watts, classifying this group of devices as a hot electronic device. While the industry is getting away from this particular type of module, there is no guarantee that in the future such devices will not reappear. One solution if there are not too many, is to simply cut a Nomex (a thin card board like material that is fire proof) baffle in the form of a channel, that fits over them, attach to the motherboard with adhesive to form a duct and then pull air vigorously through the channel. This works better than so called DIMM module coolers. We have included a FIG. 35) which demonstrates how to make a metal channel out of aluminum or copper than can fit over DIMM modules that have been equipped with heat spreaders, that removes the heat from the modules making it possible to distribute that heat into the motherboard they are mounted on. This device also will work well with blade solutions (see FIG. 21) where we suggest using this device and adding a heat pipe to it that then interfaces the cold spreader at the edge of the card using a simple device such as a stand off and screw that brings the heat pipe's condenser end into thermal contact with the card's cold spreader. In extreme situations where there are more than four DIMM modules being cooled the heat pipe could actually be replaced with a miniature LHP similar to the ones employed to cool CPUs.

When it comes to liquid cooling, the embodiments provided make it possible to employ LHPL cooling with condensers that are either directly or indirectly cooled with chilled liquids including water, safely. A new method for interfacing all closed loop passive heat transfer devices to chilled liquids has been introduced which employs a cold plate along with what we call a cold spreader (that is thermally attached to the LHPL working fluid's condenser lines) that comes into contact with the cold plate when a rack mount chassis gets installed inside of a rack cabinet. This interface, while not quite as efficient as the directly cooled interface we are about to describe, in certain situations, like blade and COTS Single Board Computer (SBC) situations, makes it possible to cool these devices as well, without using the quick disconnects that direct chilled liquids require. To improve the quality of the heat being rejected by these split condensers, a counter-flow version is also embodied and examples are provided of how to employ the cold plates that are a component of a split condenser to also cool air that is either circulating within a sealed chassis or being passed through a chassis that is being evacuated either by internal fans or a negative pressure air duct.

The majority of the world's data centers today employ air cooling and water chillers. Last year, when asked if they needed water on the data center floor, a majority of data center users said no. This year, the tide is changing and a majority now say they need it, especially in places like Europe where there is no excess capacity available on the grid to power data centers. As data centers shift to water on the floor cooling, they will be able to take advantage of the most efficient physical methods which this disclosure employs. These methods employ LHPLs that are directly cooled with chilled liquids whose components are housed in a sealed enclosure in which the remainder of the components within the enclosure are being cooled by either liquid cooled cold plates or by a combination of them and air that is circulating about a chassis or by a chassis that has access to chilled liquid cooled air heat exchanger—any combination of the three work equally well although cooling things like power supplies which have concentrated loads is always a benefit. In situations where there is a large content of cold plates the area within the chassis that can be classified as cold is huge making it possible for slow moving fans to actually out perform liquid chilled air heat exchangers. The precise combination is clearly a function of the components housed in any particular enclosure that is being cooled.

One of the most crucial aspects of any system whose goal it is to produce secondary coolants whose temperature is hot enough to make it all the way back to the cooling tower of a data center is the design employed in the LHPL chilled water condenser. The condenser design that we created that did the best job of producing high temperature effluent employed counter-flow heat exchange and used a chilled water jacket that was made of a material that does not readily conduct heat in addition to employing a helical wire that was thermally attached to the serpentine shaped condenser pipe, forcing the liquid to take a longer path and simultaneously increasing turbulent flow within the channel that improved heat transport between the liquid and the jacket that contained.

The final claim in the disclosure is for a data center cooled with the afore mentioned devices in which the servers in the data center room is directly attached to the cooling tower, eliminating the need for air ducting, special insulation in the walls of the data center (to keep humid air out), the need for an air blower and finally the water chiller employed by the air blower, in localities in the United States, when on the hottest most humid days of the year, an evaporative cooling tower will return water to the data center room that is at least 30 C, which is to say for most locations as hot and humid as locations like Atlanta Ga., 365 days of the year.

Definitions Used in Disclosure and Claims

Coefficient of Performance (COP)
The ratio of the amount of heat transferred by a heat transfer device divided by the amount of electric power required to carry out the transfer. This ratio is commonly used to define the performance of devices like water chillers, whose COP typically runs between 3 and 5, but can be as low as 1 for absorption chillers which employ waste heat to cool water. The concept is now also used to define the performance of electronic cooling devices such as Peletier Coolers whose COP is also 1, which is not very good. The COP of an LHPL is infinite!

ECOP
The COP of an electronic enclosure—simply the power consumed by the enclosure, minus the power used to cool it, divided by the power used to cool it. A computer which consumes 400 Watts and uses 100 Watts to run its cooling fans has a ECOP of 3. In situations where Peletier cooling and other methods that do not employ motors, the electric power needs to be added to the cooling load.

TCOP
In large installations such as data centers, the total power consumed, minus the power used to run all cooling including all of the energy sources that contribute to ECOP. This value is typically 1 for modern data centers but using the techniques and inventions divulged in this disclosure can be raised to 2.

Loop Heat Pipe (LHP)
A Passive two phase closed loop heat transfer device that consists of an evaporator that contains a wick that effects heat transfer between the item being cooled and the LHP's working fluid by allowing its working fluid to boil and employs the structure of the wick to produce the capillary pressure needed to drive the working fluid about a closed loop employ a compensation chamber on the liquid input side of the evaporator along with a set of condenser tubes that transports the working fluid to and from a condenser where it gets cooled, changes phase and delivers its heat load to flow cooling it.

Loop Heat Pipe Like (LHPL)
A device that contains all the ingredients of a Loop Heat Pipe or Capillary Pumped Loop that has some additional derivative feature such as a pump at any point along its condenser path designed to either increase the working pressure of the working fluid or extend its reach.

Capillary Pumped Loop (CPL)
A device that contains all of the ingredients of a Loop Heat Pipe but in which the compensation chamber is no longer situated at the liquid entry point to the evaporator.

Standard Heat Pipe (HP)
A closed tube that gets heated at its evaporator end causing its working fluid to vaporize before moving to the other end where it condenses and then returns to the evaporator end through a wick that lines the walls of the tube.

Two Phase Passive Heat Transfer Cooling Devices
LHPs, LHPLs, CPLs and HPs

Primary Heat Load
The sum of the heat being rejected by the "hot electronic components" within an electronic enclosure.

Secondary Heat Load
The heat being rejected by devices other than those included in the primary heat load.

Hot Electronic Component
Any electronic device that rejects 50 or more Watts or consumes more than 50% of the power in a system composed of electronic components.

Densely Packed Hot Electronic Components
Any hot electronic component operating in an environment in which conventional electronic cooling devices can not be employed without wasting large quantities of energy.

Conventional Electronic Cooling Devices
Include fans, blowers and heat sinks cooled by them and in the case of liquid coolants, cold plates and devices designed to absorb energy but specifically excluding pumps other than pumps found in LHPLs.

Thermally Attached

Techniques which connect a pair of heat transfer devices together in such a manner that the resulting thermal resistance of the combined device is minimized.

SUMMARY

Methods were disclosed which make it possible to employ Loop Heat Pipe, Capillary Pumped Loops and other passive closed loop heat transfer devices to cool electronic components housed in electronic enclosures, including rack mount chassis housed in rack cabinets, desktop computers, COTs computers, telecommunications equipment, electronics employed in vehicles and virtually any electronic enclosure one can imagine in which either air or a chilled liquid can be provided to cool the enclosure.

The resulting methods made dramatic reductions in the amount of energy employed to cool electronic components housed in electronic enclosures while at the same time making dramatic improvements in other operating characteristics, including reliability, the amount of heat being reject to the outside world, the amount of noise produced, the size of the power supplies needed to power units, the cost to build and operate data centers and last but not least, the ability to cool very hot electronic devices housed in electronic enclosures that are densely packed.

The embodiments included designs for LHPL condensers, including air and water cooled condensers that employed counter-flow techniques, LHPL CPU heat spreaders, sealed chassis and sealed air ducts, methods for controlling the vapor content of air within sealed chassis, methods for connecting chilled liquid sources to condensers including split condensers that eliminate the need for quick disconnects and quick disconnects that are shielded from the chassis being cooled by a duct.

The methods included embodiments that make it possible to cool the majority of the data centers operating in the United States without having to employ either air blowers or air chillers 365 days of the year, reducing the acquisition costs significantly while at the same time reducing the energy consumed by 40% or more.

FIG. 12 is a different view of the chassis shown in FIG. 11, with all but the top most chassis penetrating through the sealing flap within the negative pressure air duct they are attached to;

Figure 15:
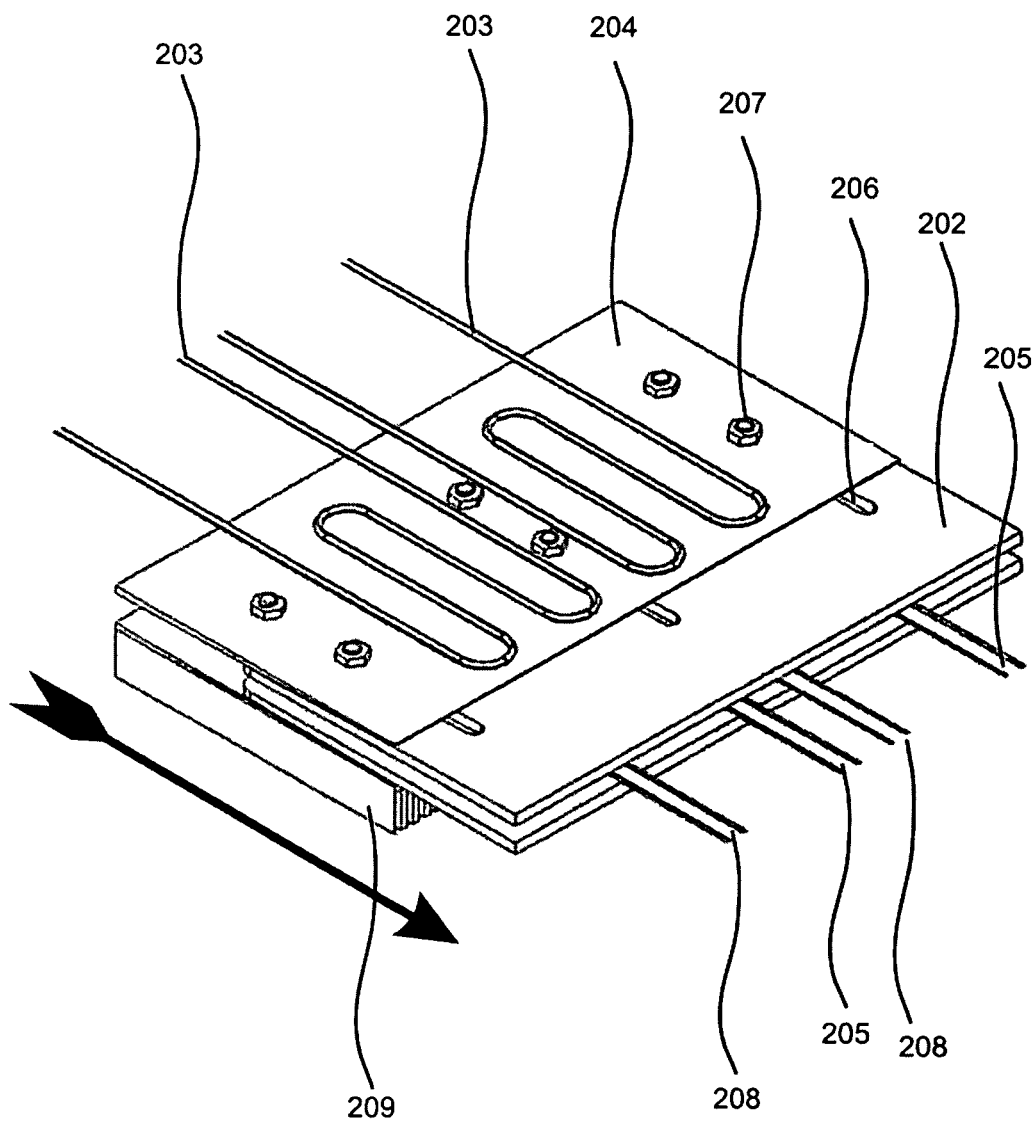
FIG. 15 is a detailed perspective view of a split condenser in which a male cold plate gets inserted into a female cold spreader that is attached to the condenser tubing of an LHP.
Figure 16:
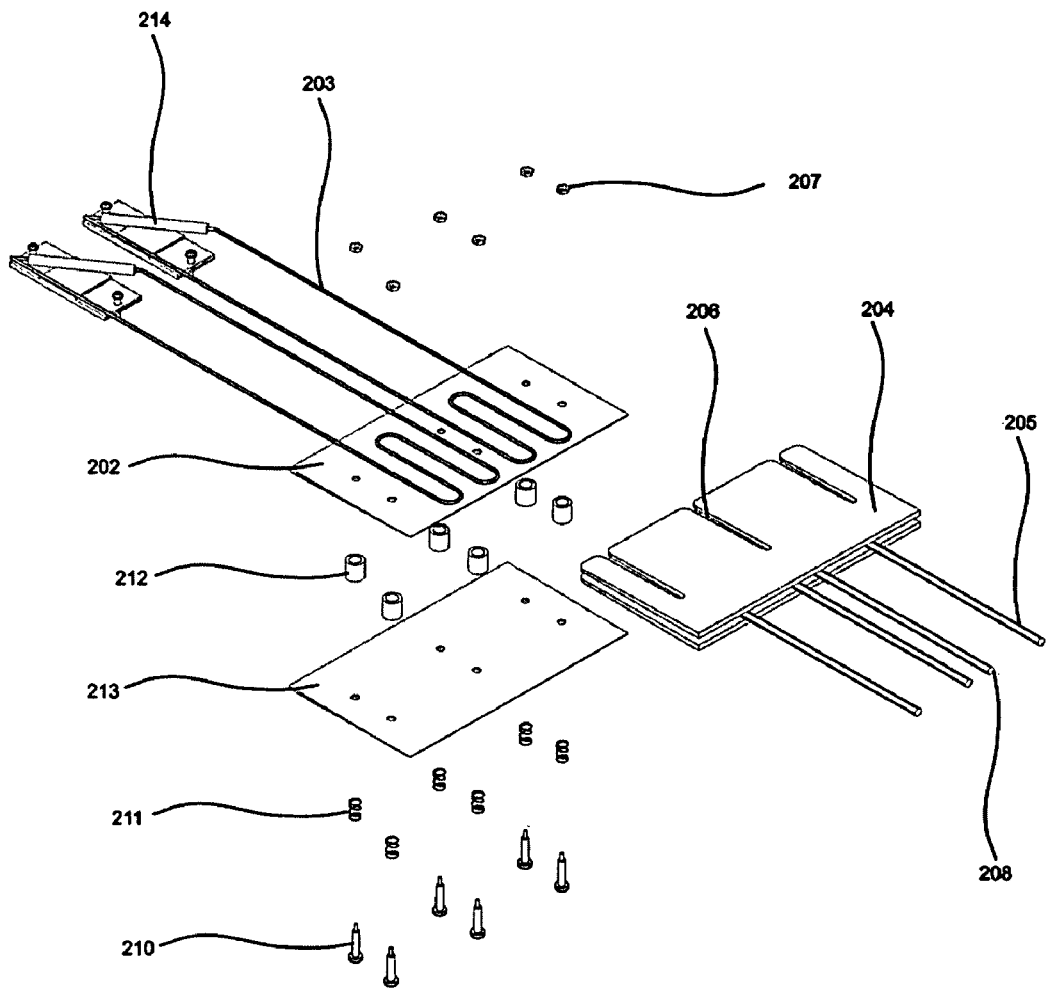
Figure 17:
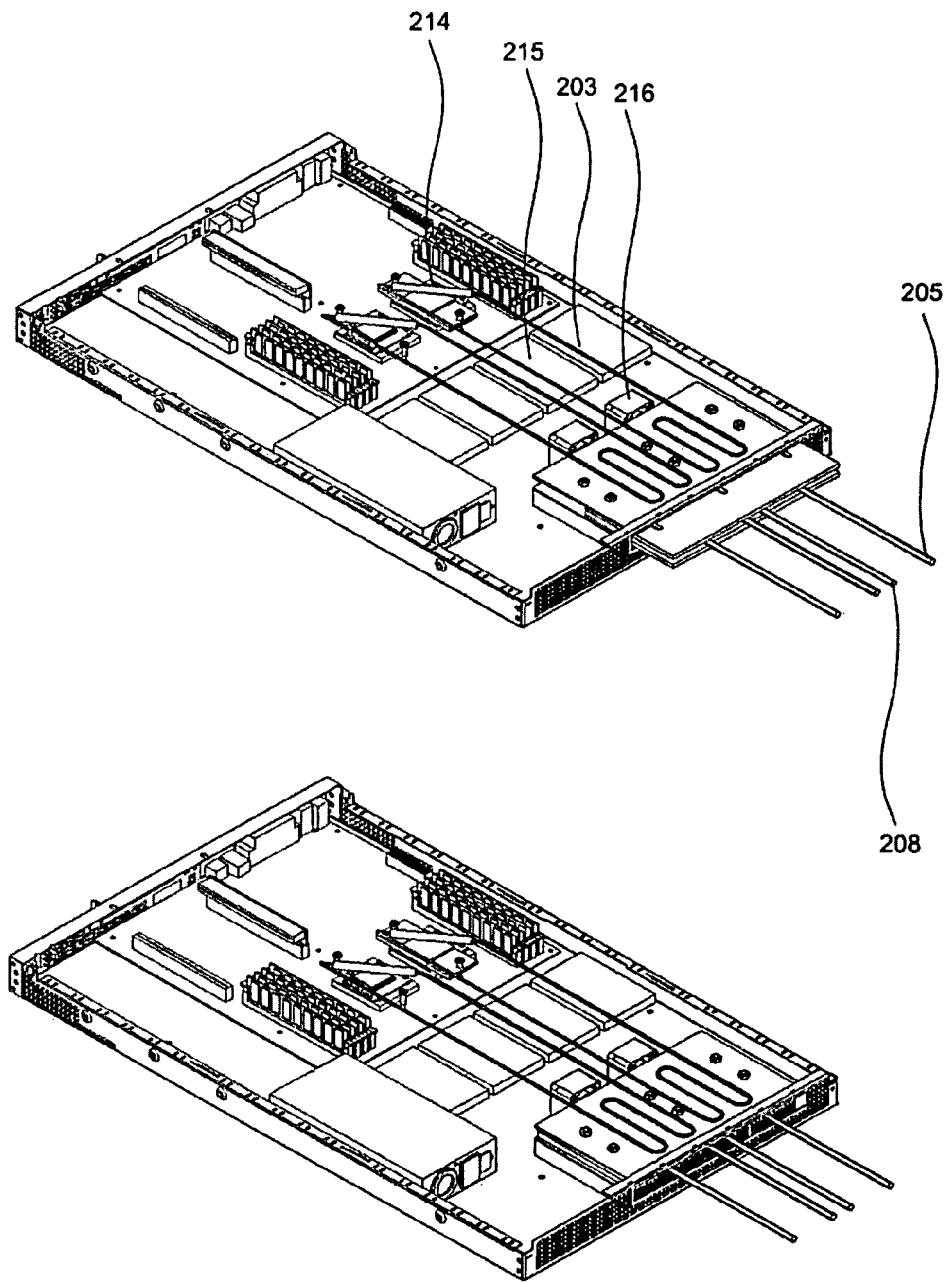
Figure 18:
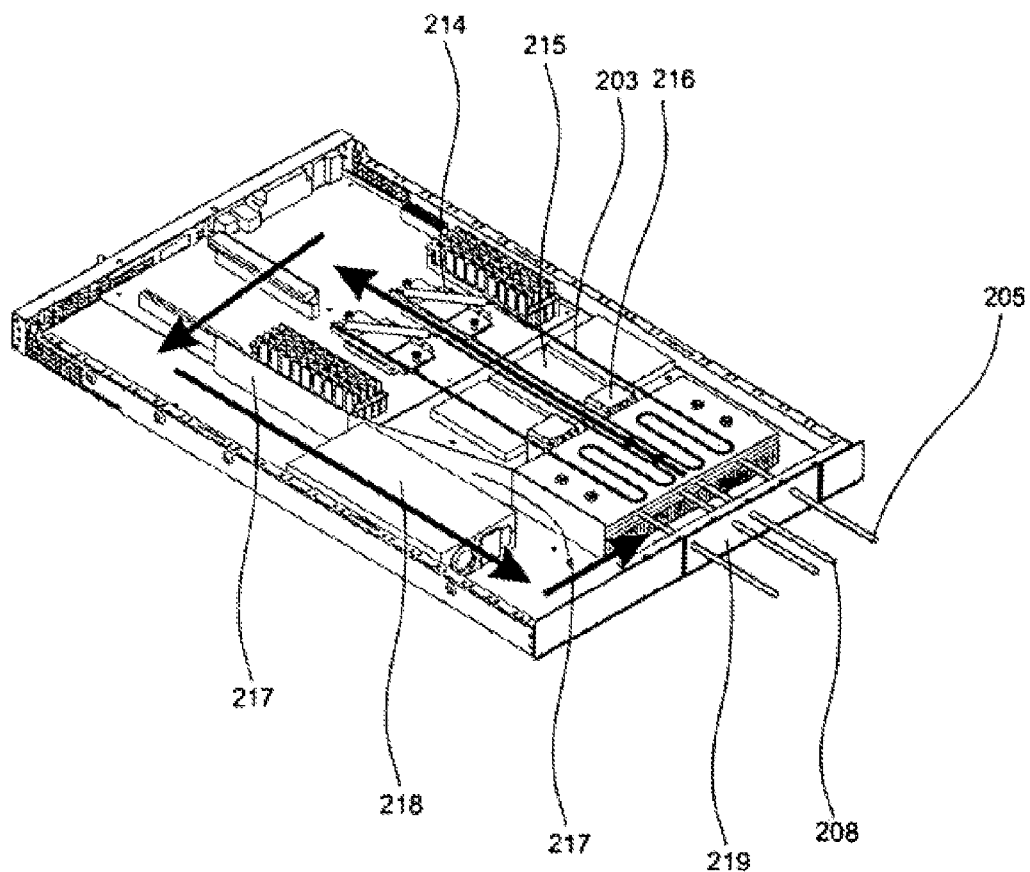
Figure 19:
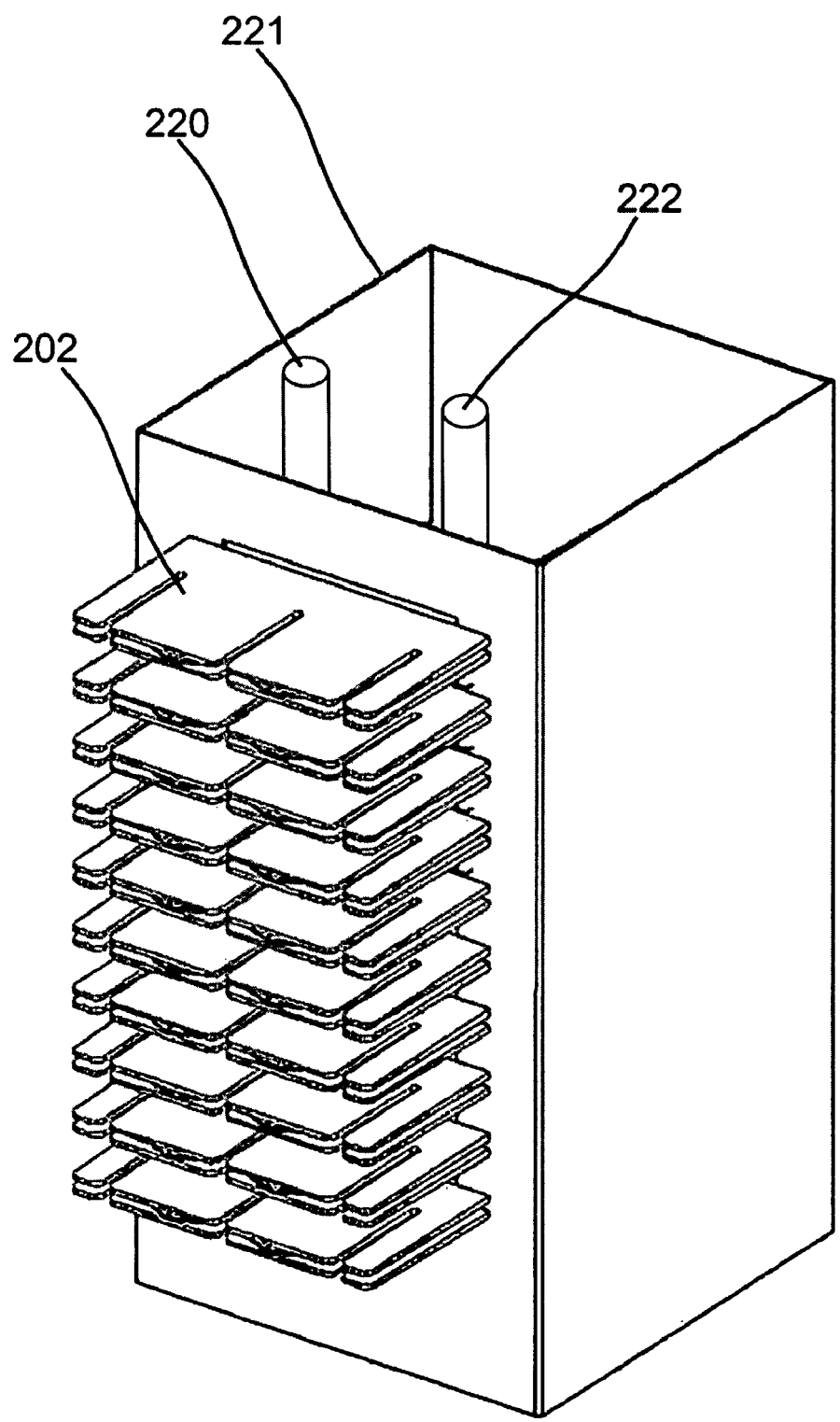
Figure 20:
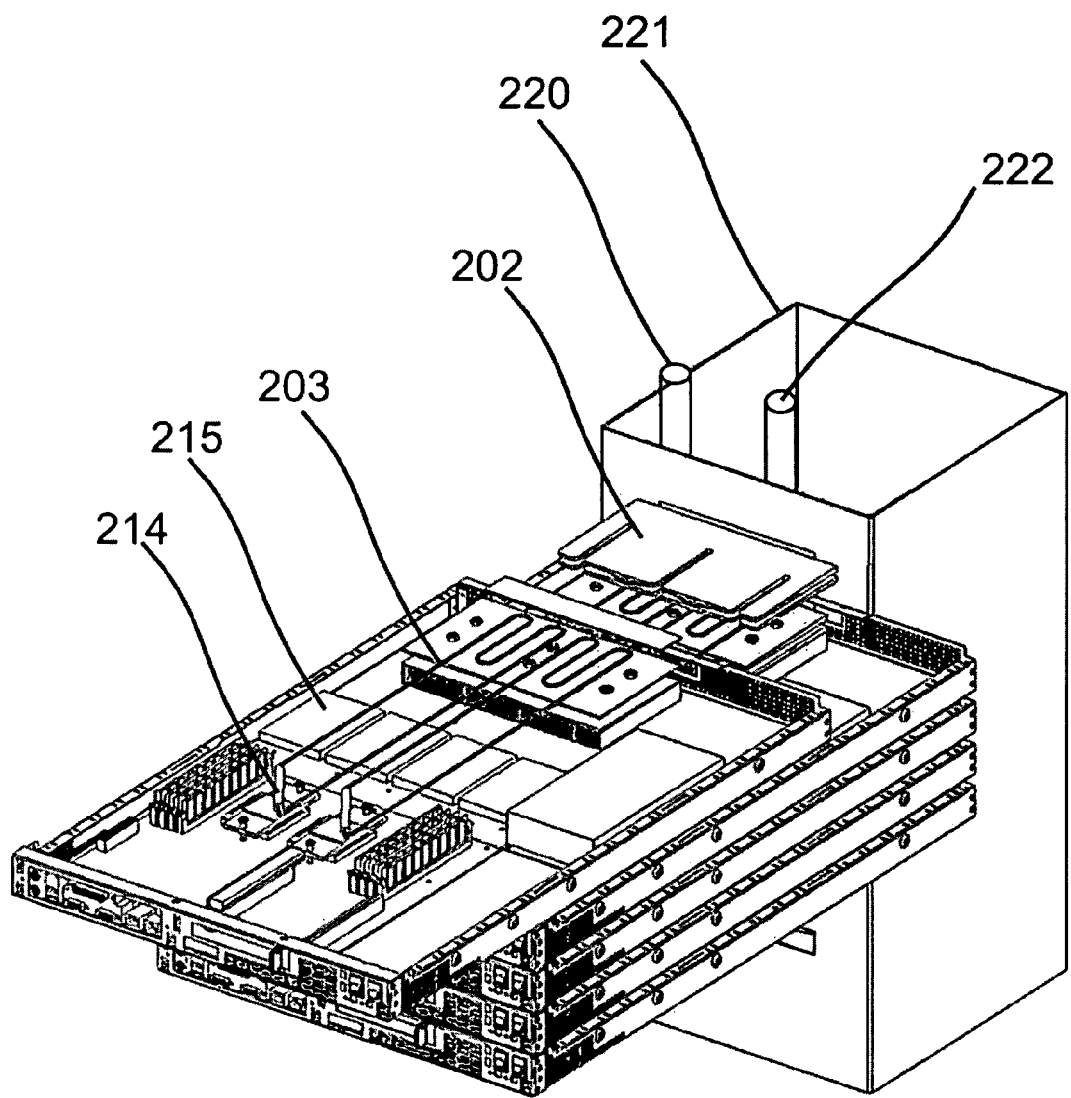
Figure 21:
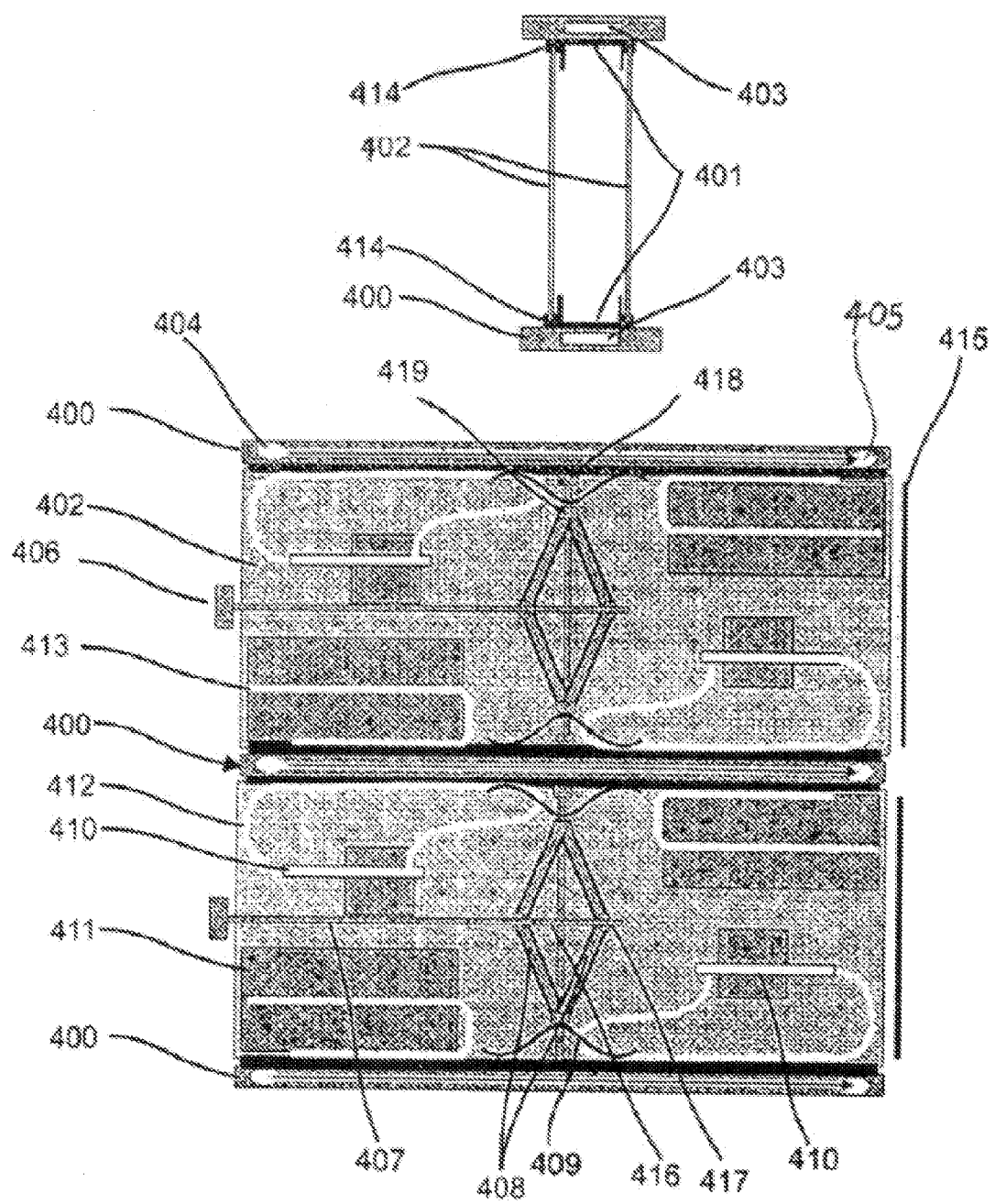
Figure 22:
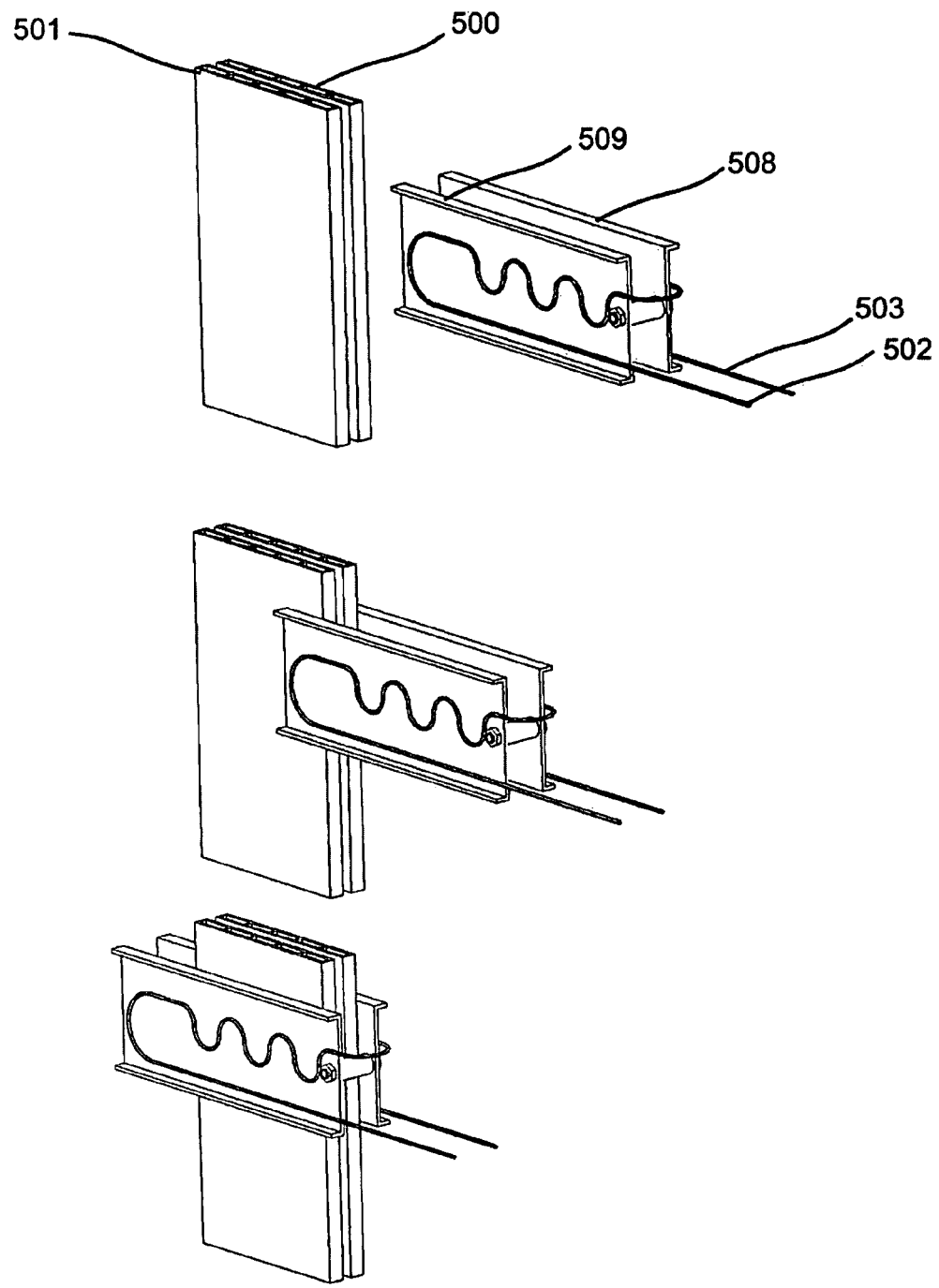
Figure 23:
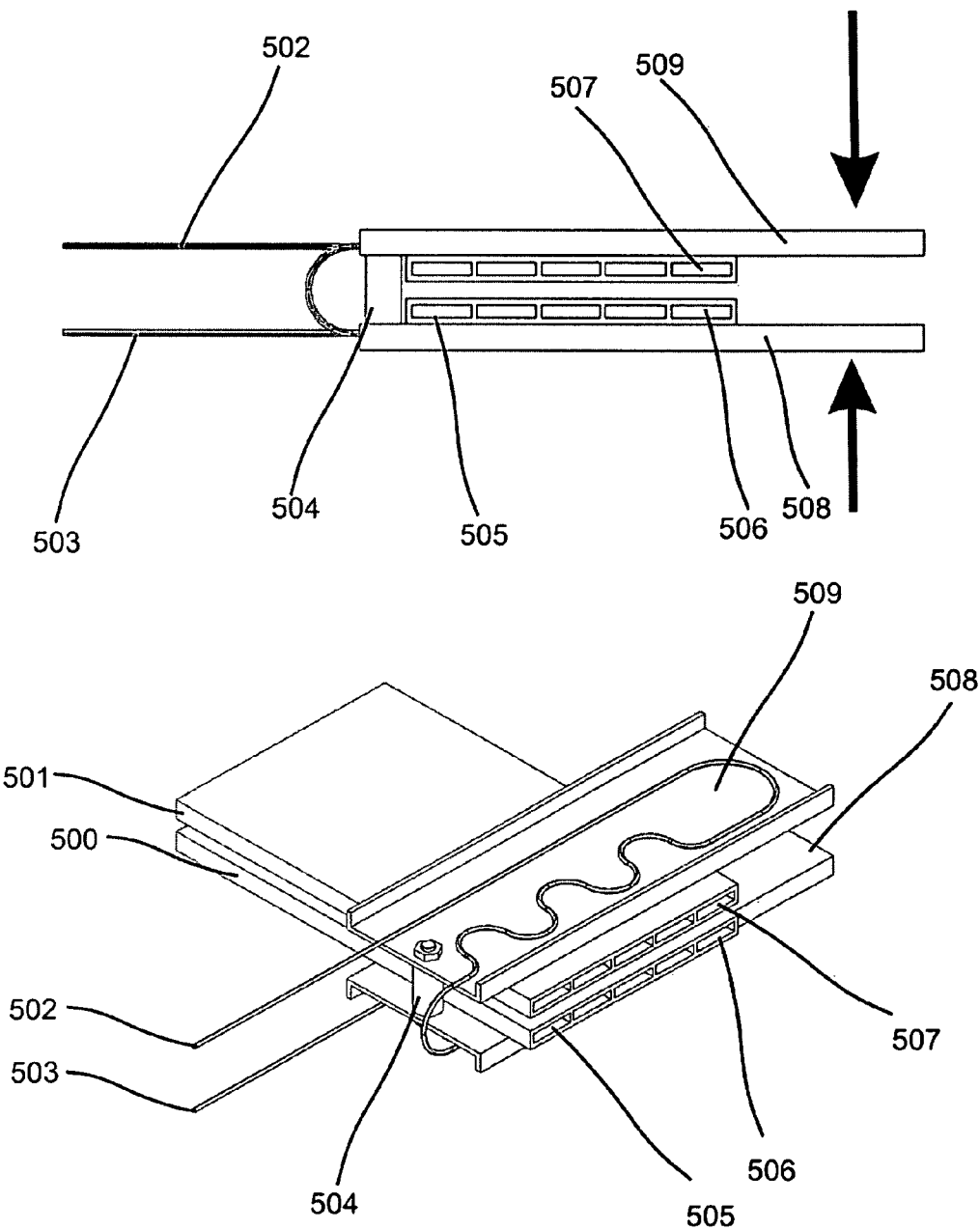
Figure 24:
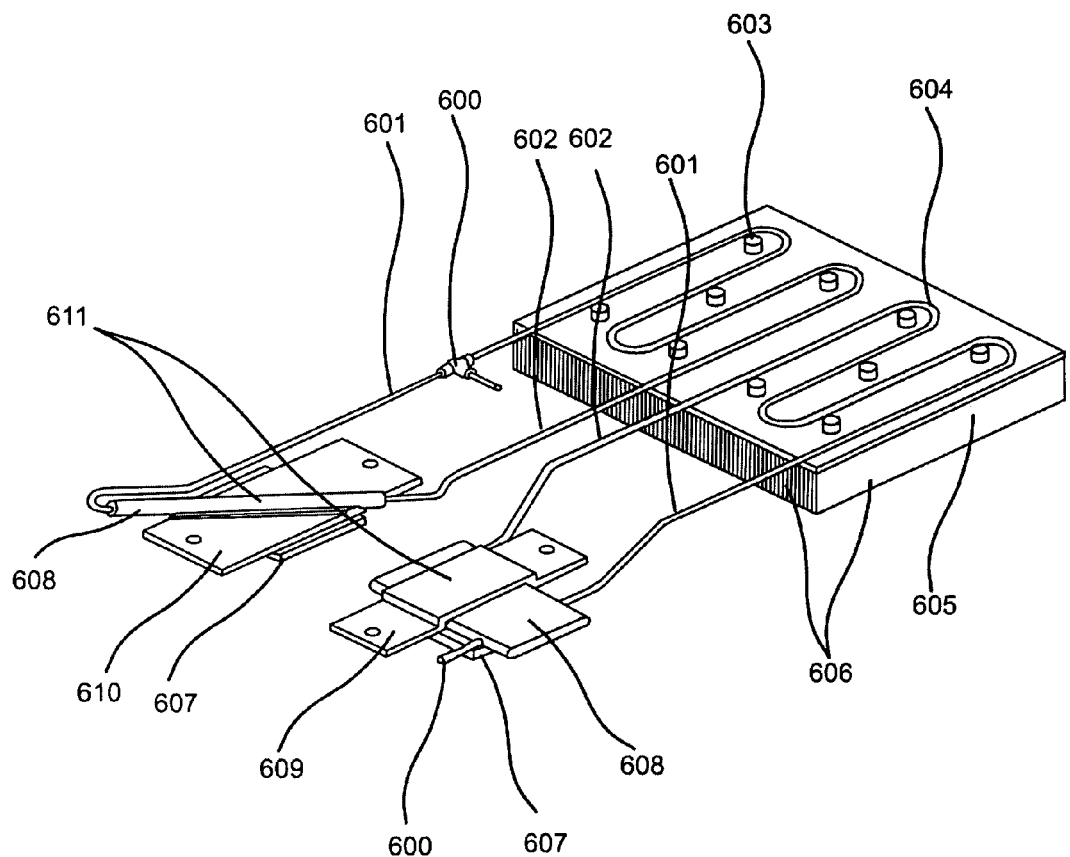
Figure 25:
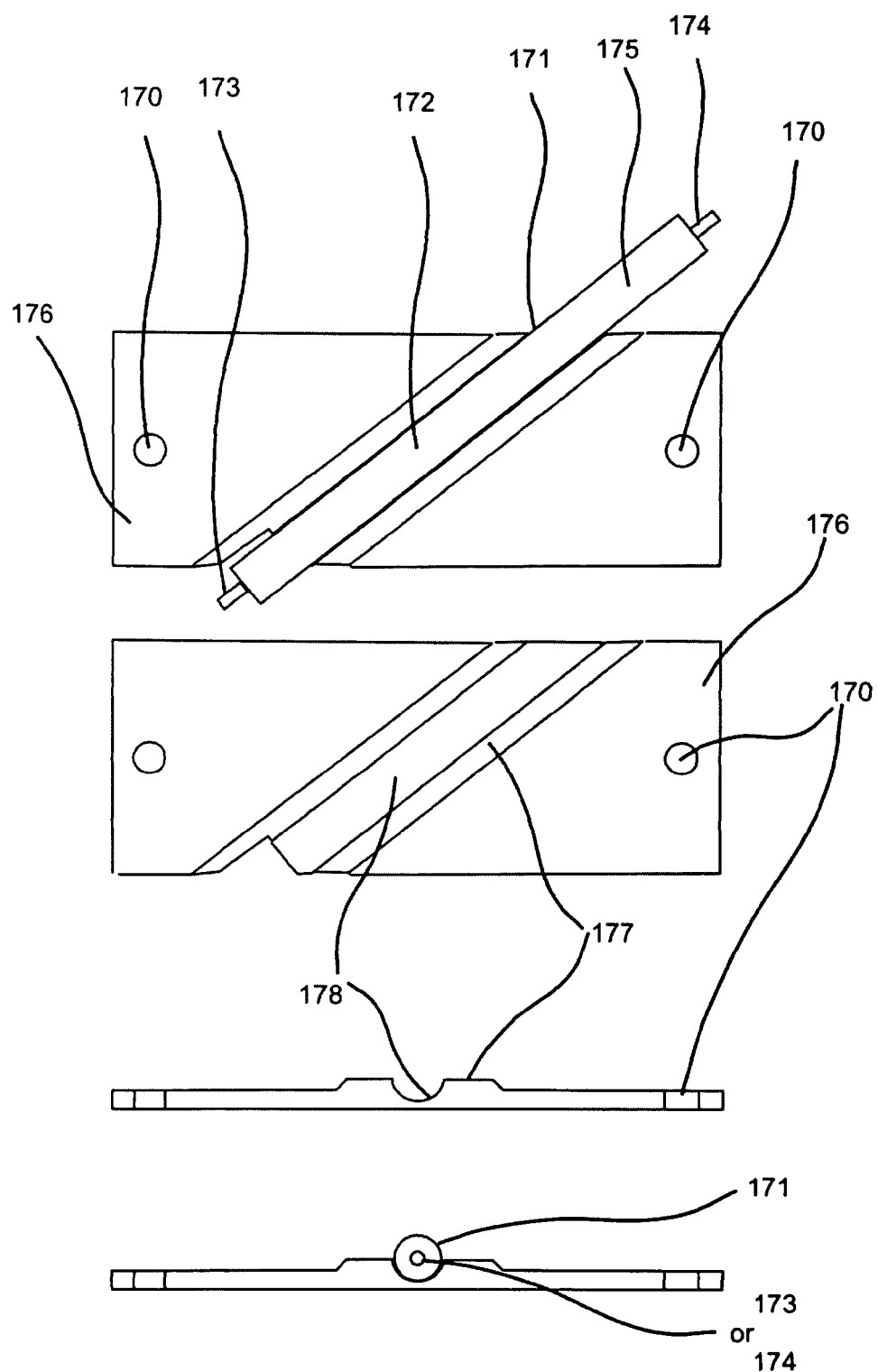
Figure 26:
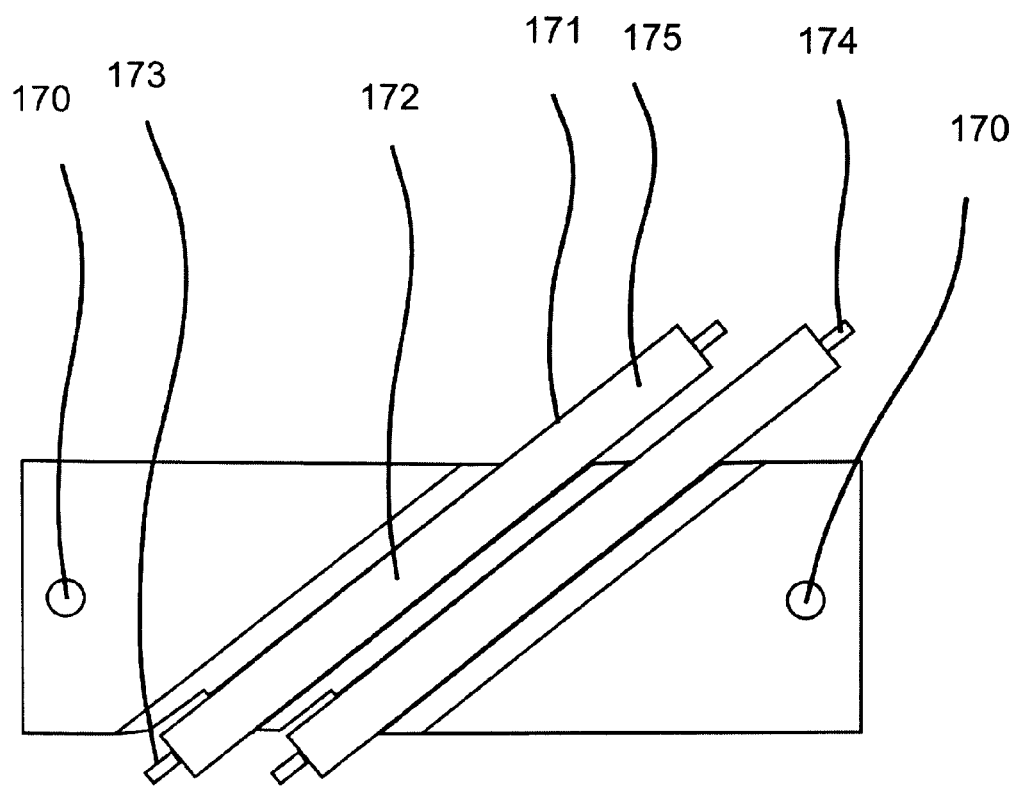
Figure 27:
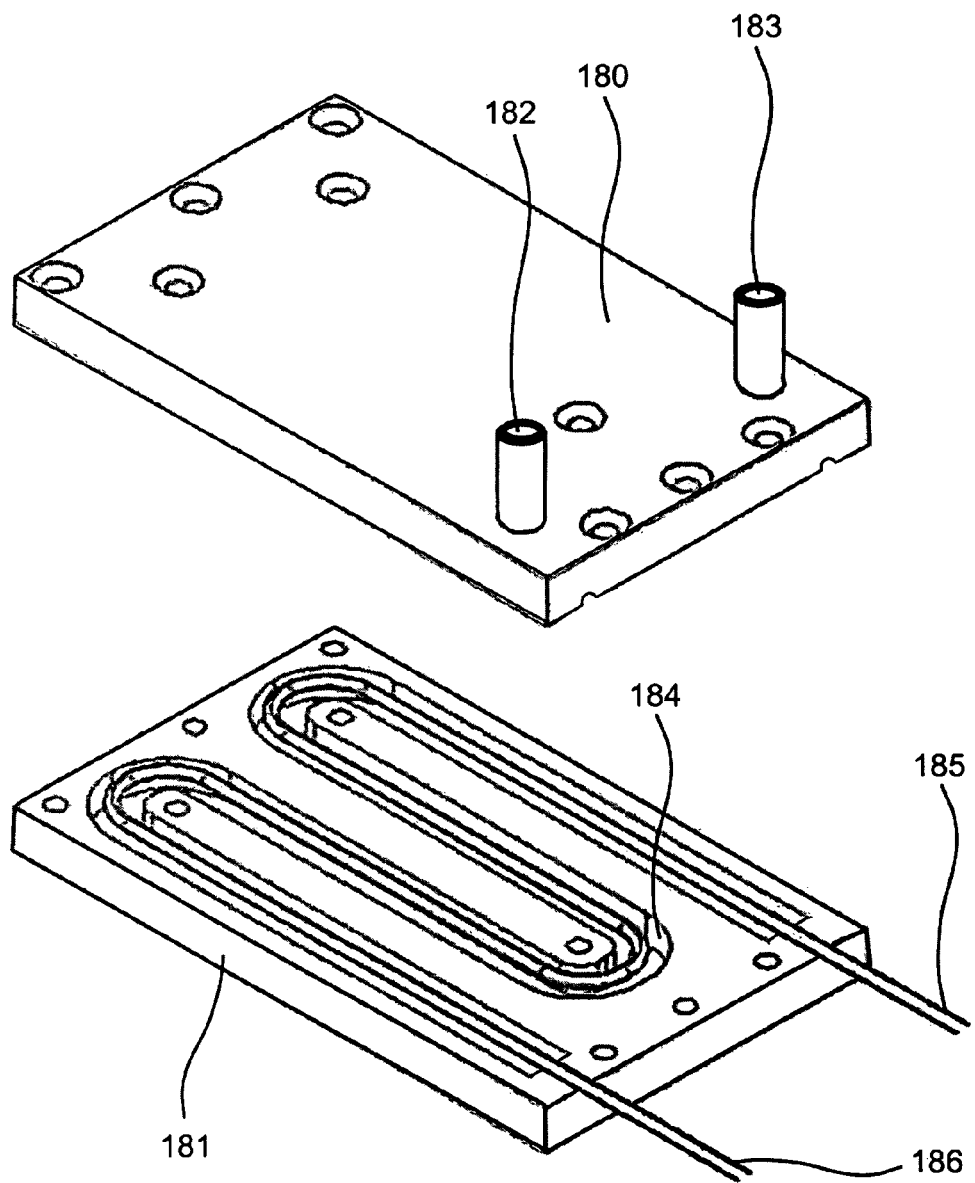
Figure 28:
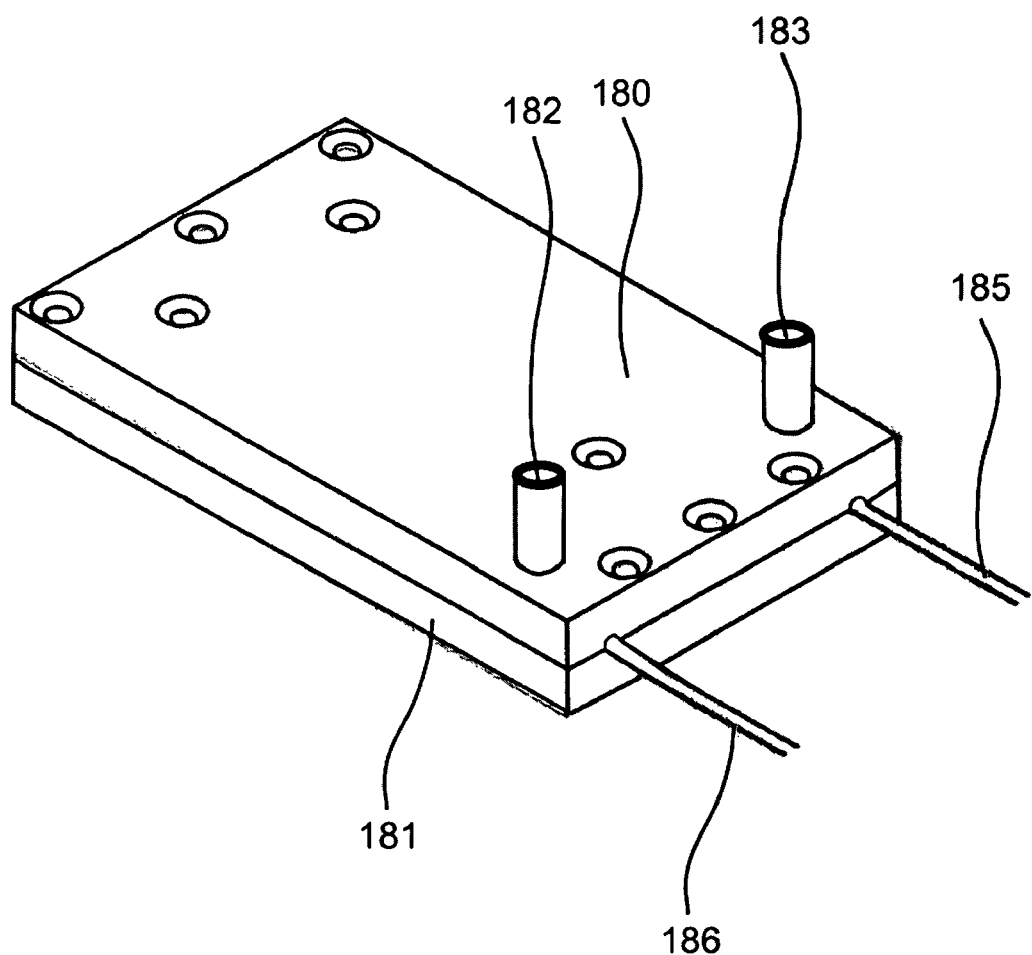
Figure 29:
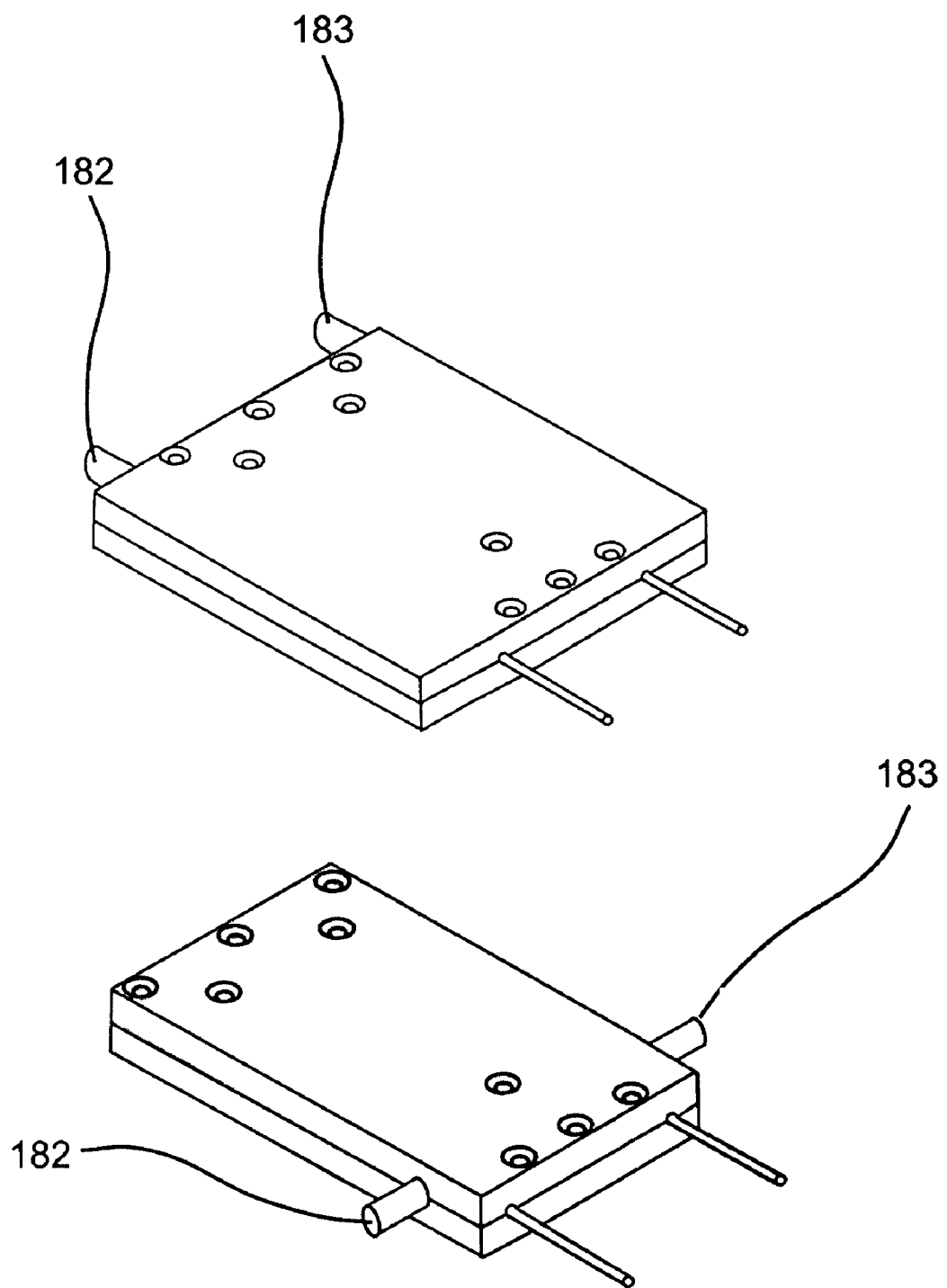
Figure 30:
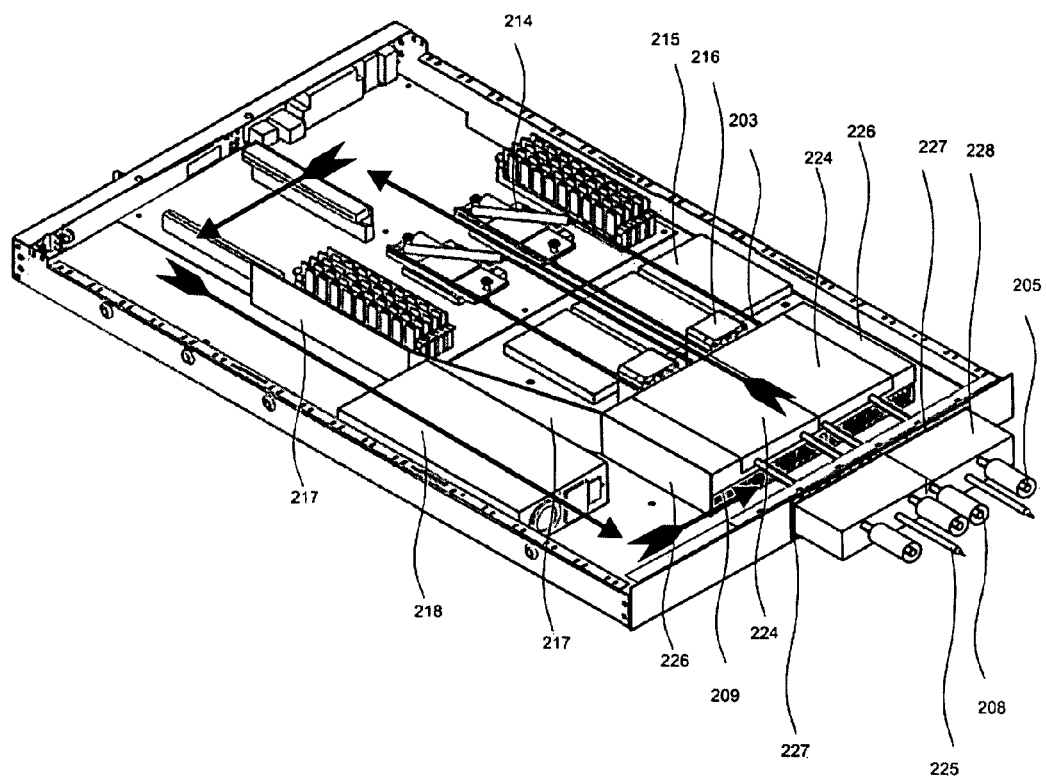
Figure 31:
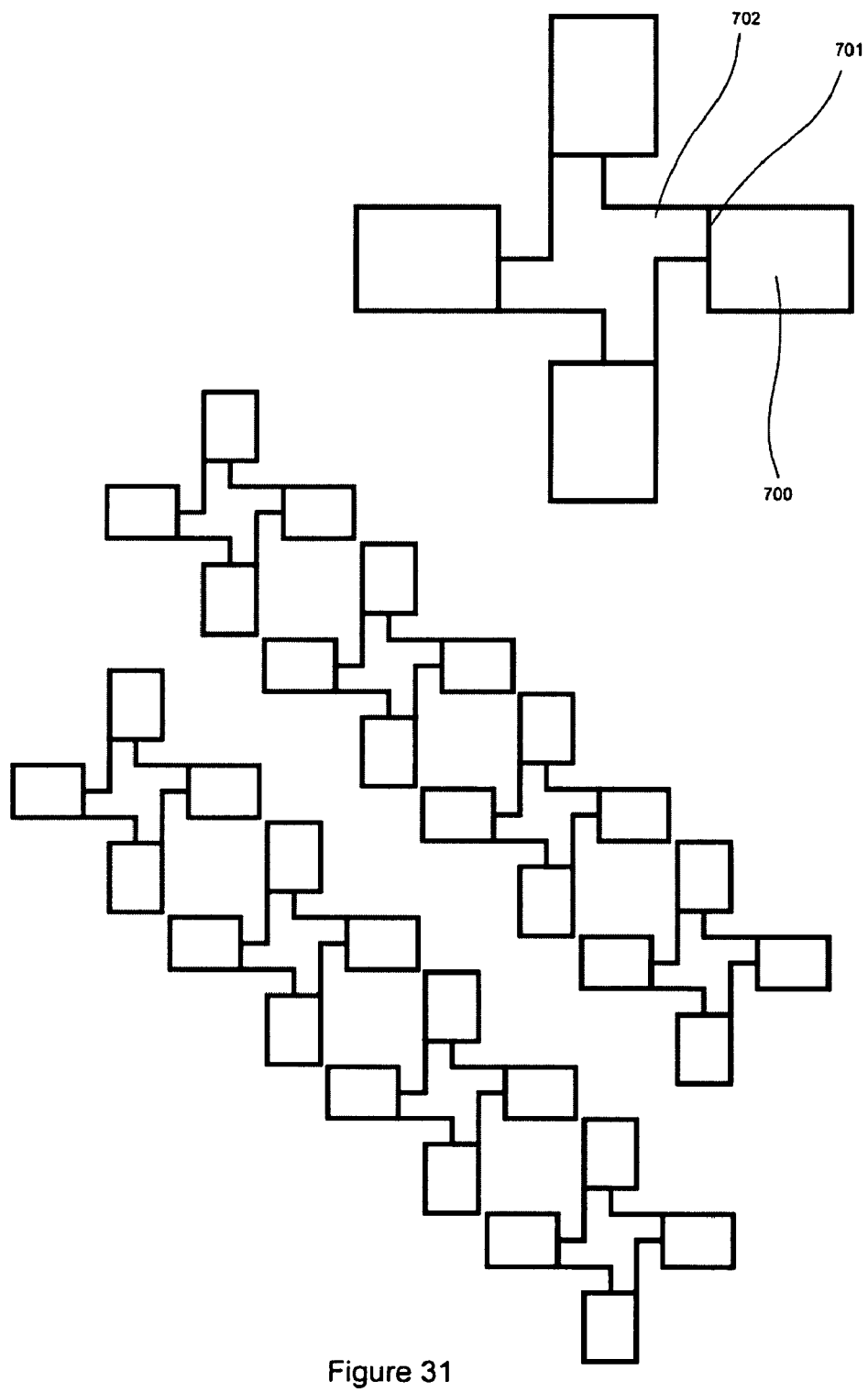
Figure 32:
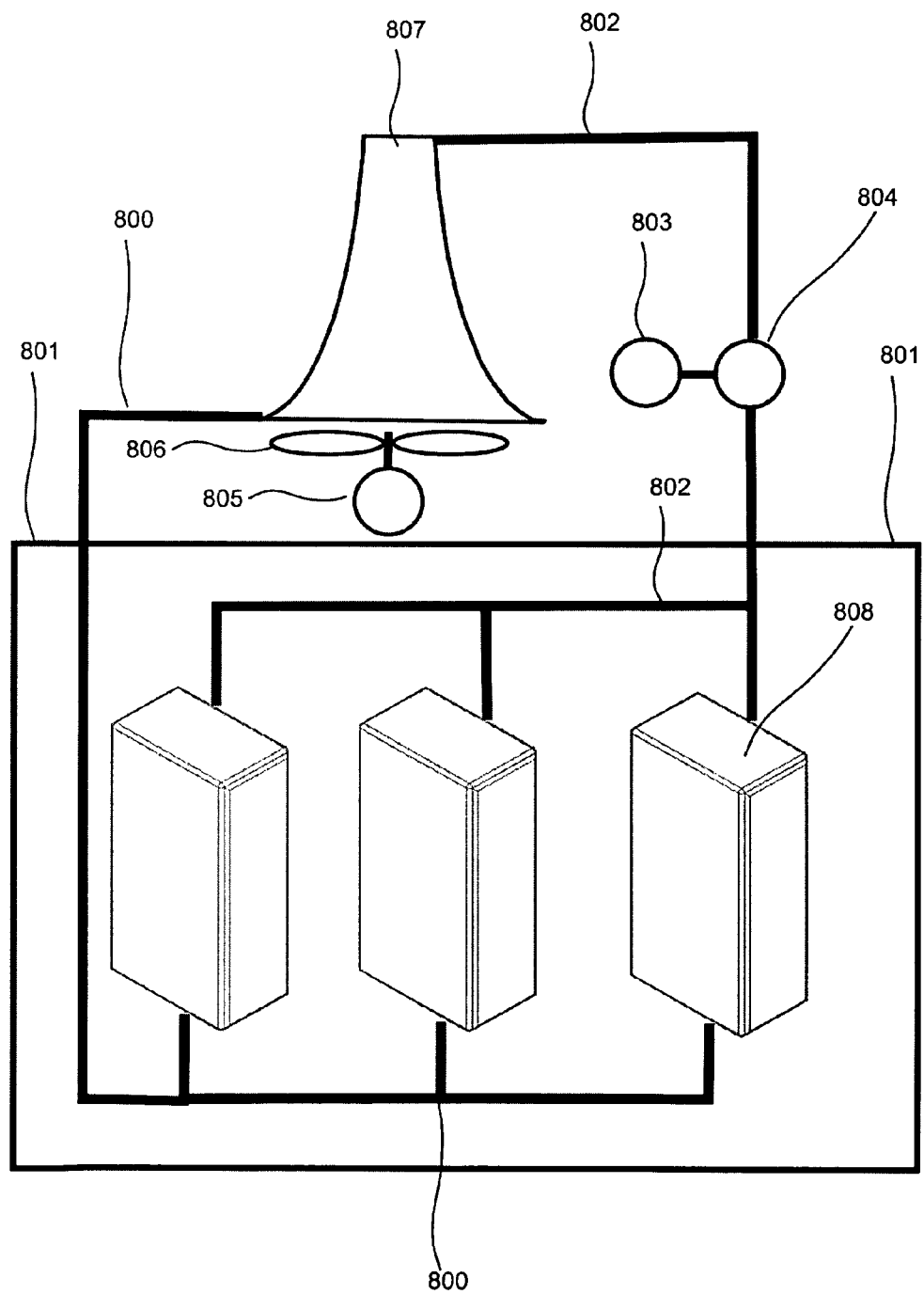
Figure 33:
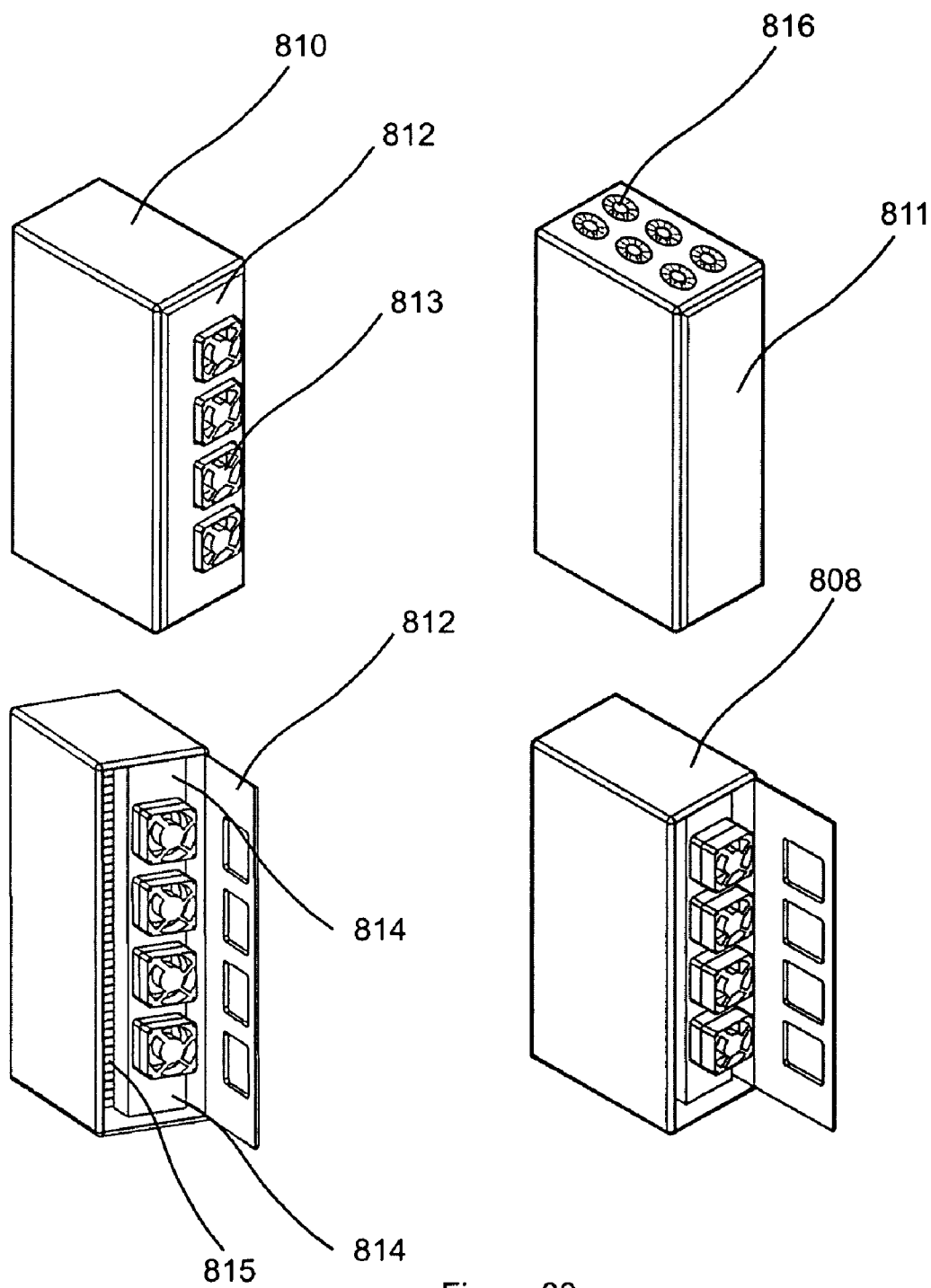

FIG. 16 an exploded view of the split condenser shown in FIG. 15 which also demonstrates how the condenser tubing links to an Ammonia evaporator;

FIG. 17 contains before and after perspective views of the split condenser components described in FIGS. 15 and 16 coming together in a 1 U chassis;

FIG. 18 is a perspective drawing of a 1 U chassis that employs a 1 U chassis that is sealed and uses the fans in both the power supply and ahead of the split condenser to circulate cooling air within the chassis using the lower half of the split condenser to cool this air;

FIG. 19 is a perspective view of a stack of split condenser male cold plates that protrude from a negative pressure air duct used to cool 1 U chassis that attach to it;

FIG. 20 is a perspective view of a stack of 1 U chassis that employ split condensers that attach to the duct in FIG. 19 and employ the negative pressure duct to remove hot air from them;

FIG. 21 contains a pair of side views of an LHP split condenser designed to cool processor blades that employs a combination of cold plates that are fixed into the chassis and cold spreaders that are attached to the blades which slide into place and employ a scissors jack to provide the thermal contact interface pressure;

FIG. 22 is a before and after sequence of perspective drawings which demonstrates how to make a split condenser that employs a counter flow architecture and which employs a cold spreader that sits outside of a chassis and makes contact with a partitioned cold plate that is vertically mounted inside of a rack cabinet;

FIG. 23 is a perspective view of the design details of the split condenser shown in FIG. 22;

FIG. 24 is a perspective view of how both an Ammonia and water LHP can be employed within a 1 U chassis and used to interface a common set of condenser fins;

FIG. 25 is a cross sectional view of the copper heat spreader used by the Ammonia LHP evaporator shown in FIG. 24;

FIG. 26 demonstrates how it is possible to employ a pair of Ammonia evaporators mounted on the same copper heat spreader;

FIG. 27 is a perspective view of a serpentine shaped condenser tube that has been enclosed within a jacket through which a cooling liquid like water is passed to cool the condenser tubing;

FIG. 28 is a perspective view of the water jacket first drawn in FIG. 27 showing the condenser tubing coming out and vertical entry and exit ports used to circulate coolant through the jacket;

FIG. 29 is a perspective of the jackets shown in FIGS. 27 and 28 with the entry and exit ports moved to locations which provide more convenient access;

FIG. 30 is a perspective view which shows a sealed 1 U chassis in which a jacketed LHP condenser is employed along with internal circulating fans and a set of quick disconnects at the rear of the chassis for providing it with the liquid coolant that cools all of the components within the chassis;

FIG. 31 shows a method of laying out rack cabinets in a data center that are attached in groups of four to a negative pressure duct;

FIG. 32 is a schematic drawing of a data center that employs three rack cabinets, a cooling tower and circulation used to move coolant directly between the chassis in the rack cabinets and the cooling tower;

FIG. 33 shows several different view of rack cabinets which employ cooling ducts and fans.

Figure 34:
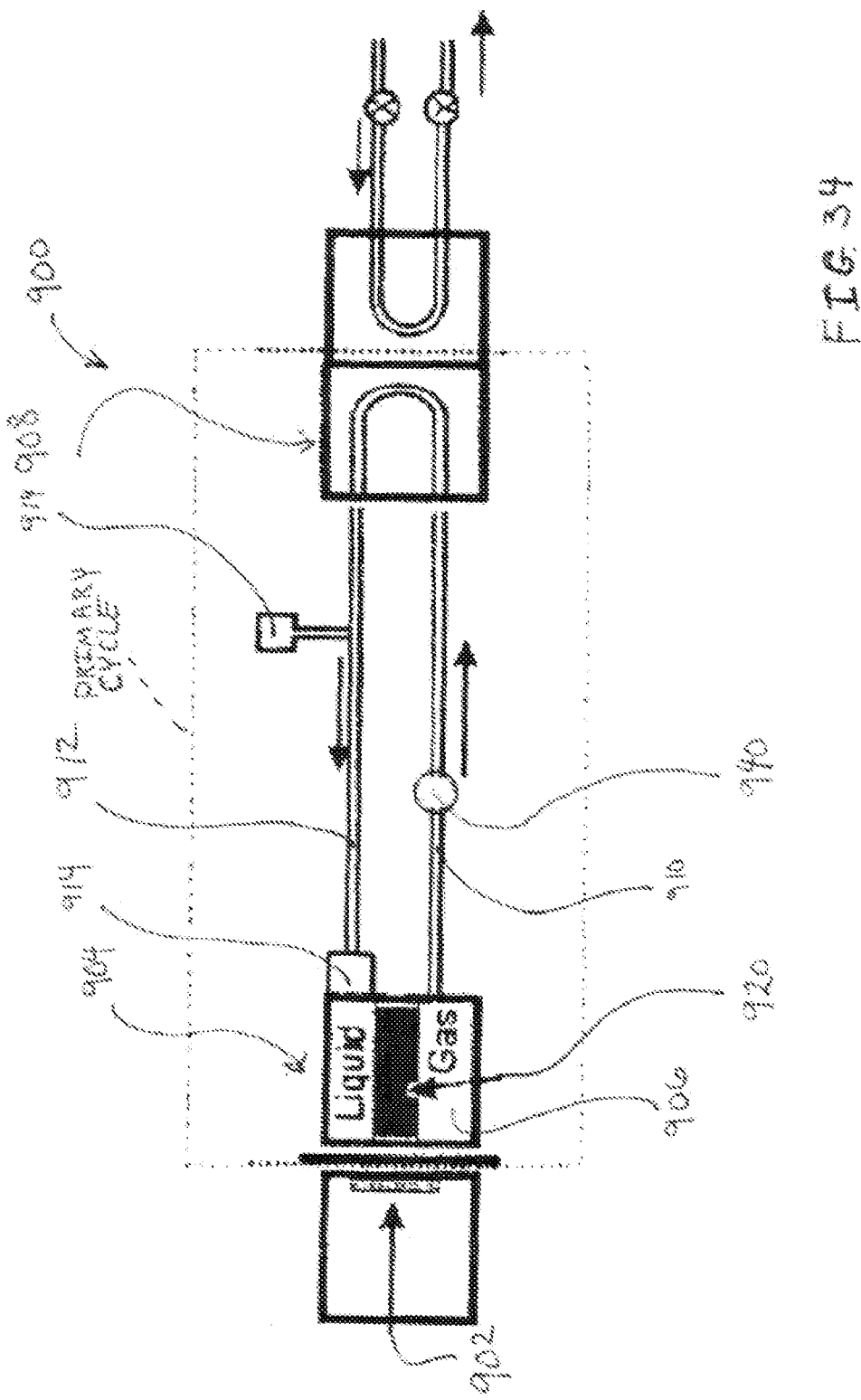

FIG. 34 is a schematic representation of a primary closed loop system.

Figure 35:
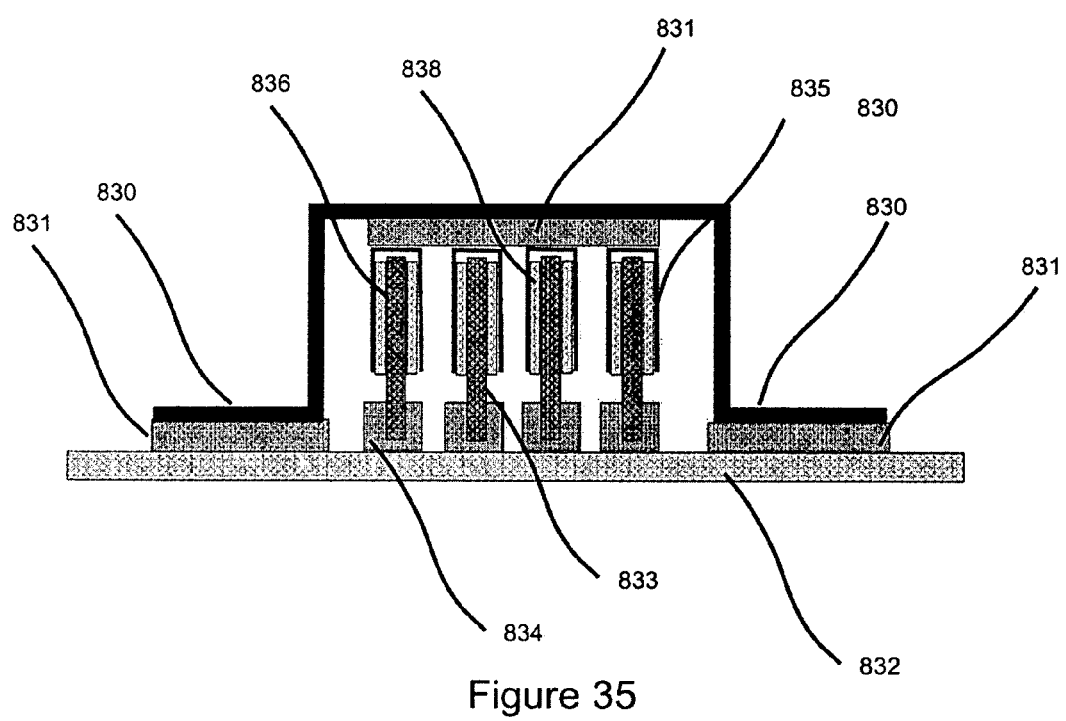

FIG. 35 is a cross sectional view of a device intended to remove heat from a group of DIMM modules.

DETAILED DESCRIPTION OF THE INVENTION

Figure 1:
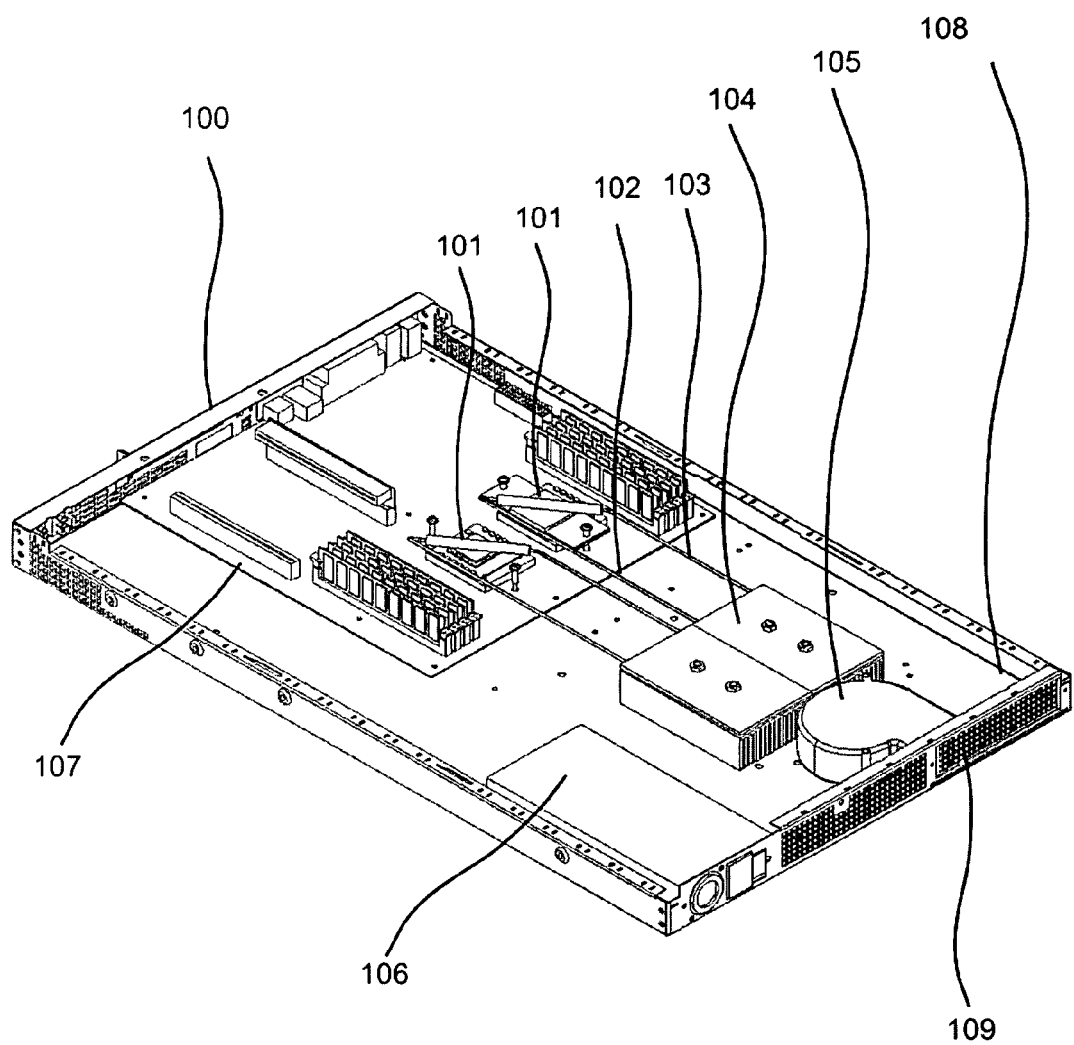
FIG. 1 is a perspective representation of an exemplary embodiment of a 1 U rack mount chassis that employs Ammonia Nickel Loop Heat Pipes to cool a pair of hot running CPUs.
Figure 2:
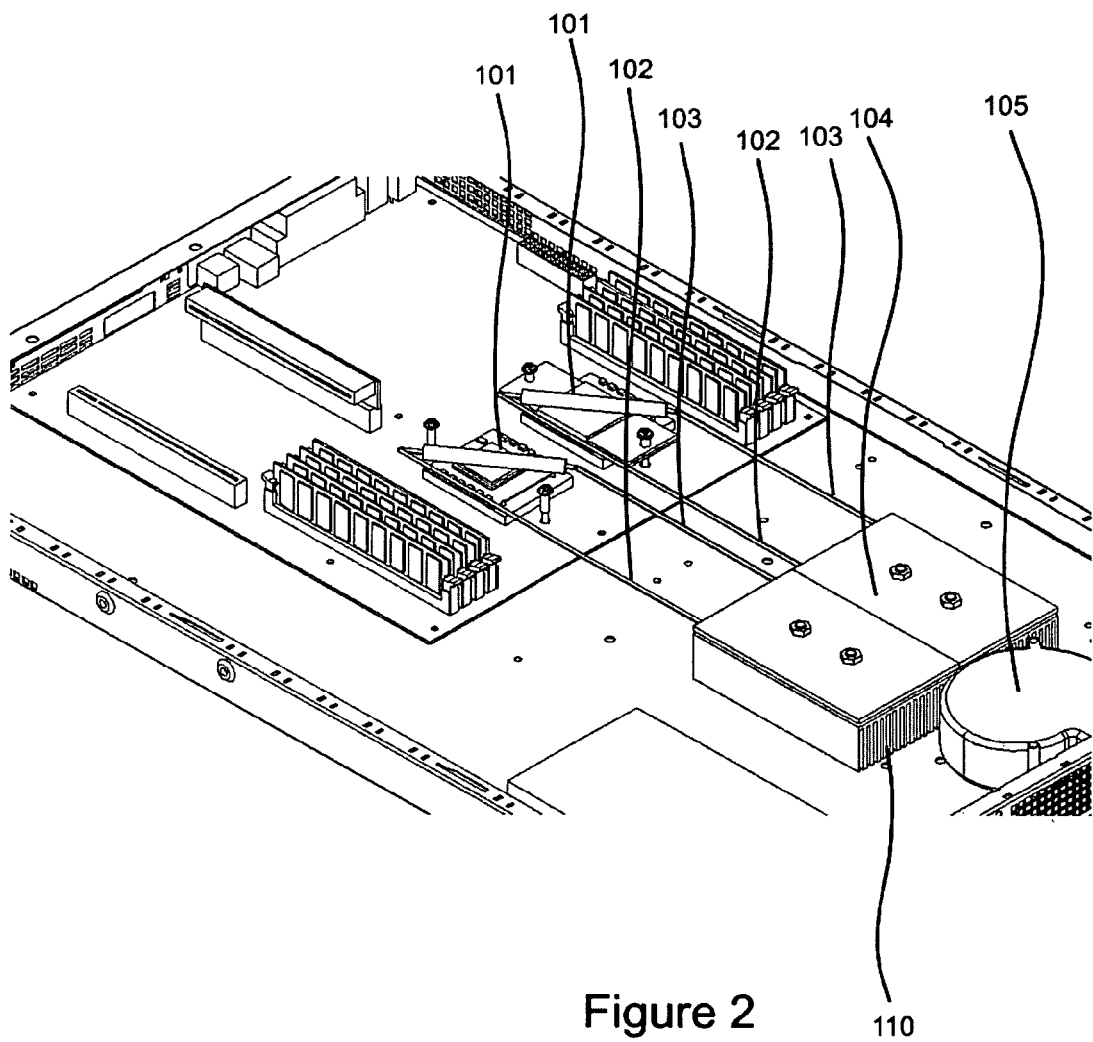
FIG. 2 is a perspective representation of the design shown in FIG. 1 shown in greater detail.
Figure 3:
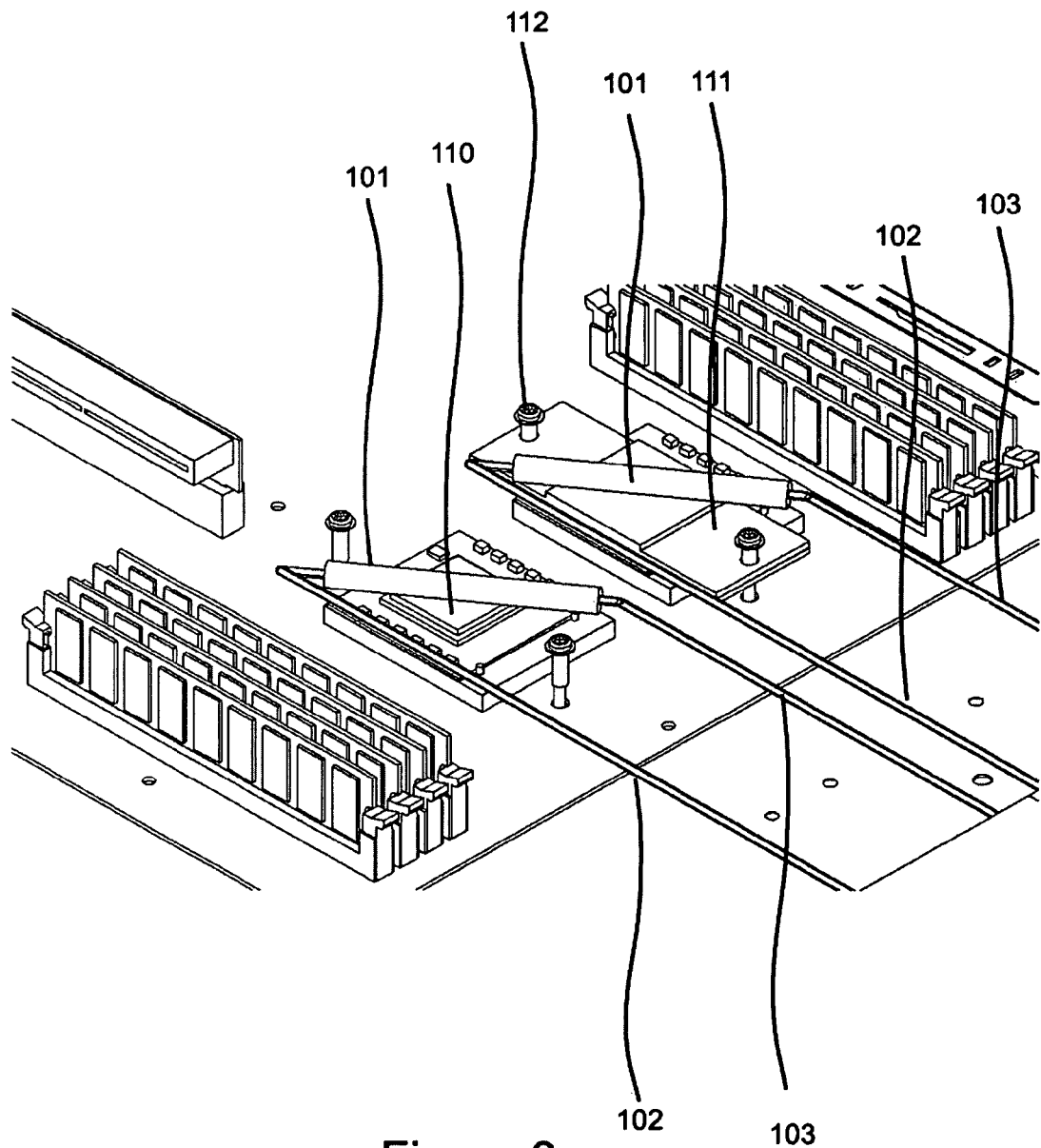
FIG. 3 is a perspective representation of the design shown in FIG. 1 shown in greater detail.
Figure 4:
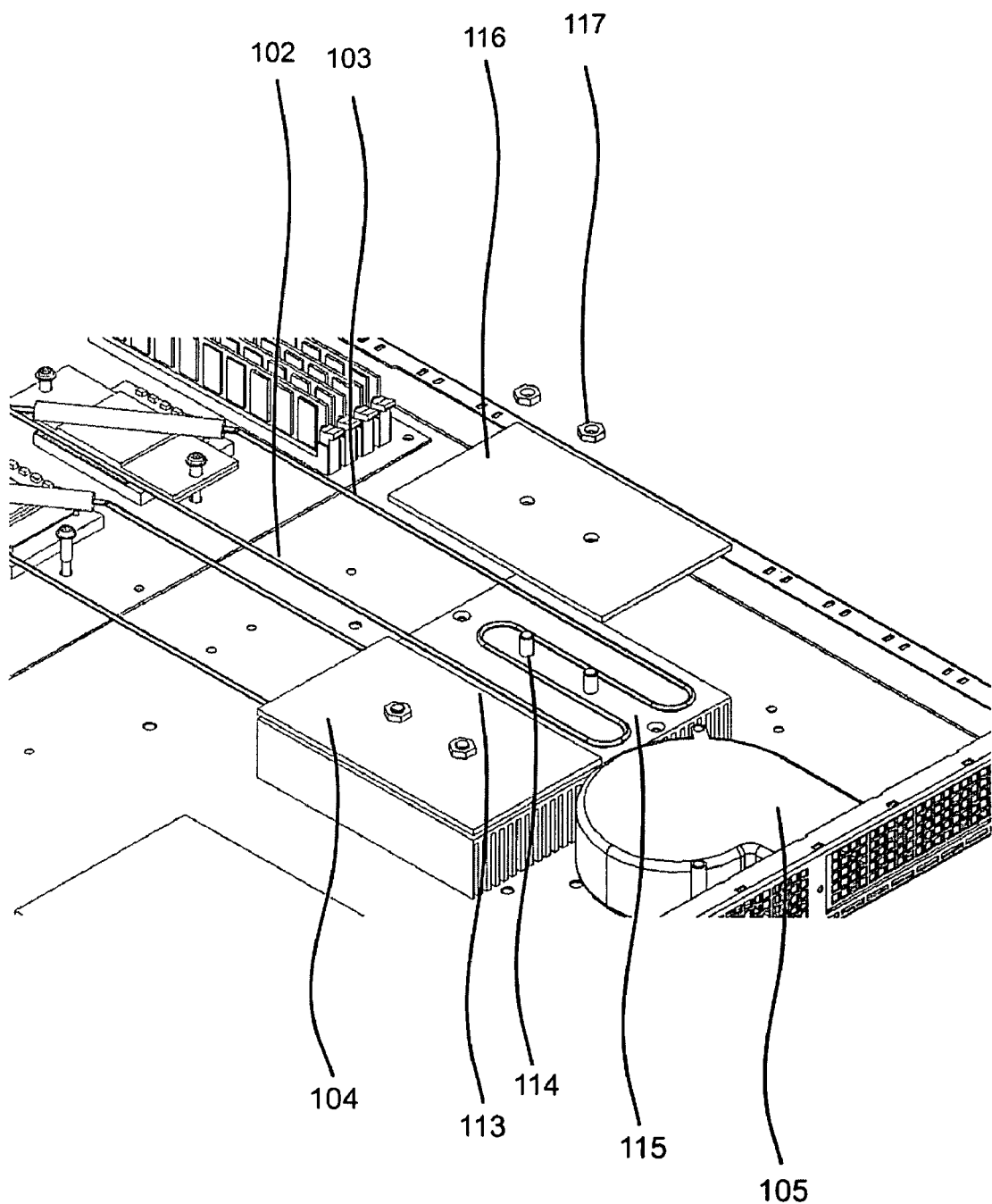
FIG. 4 is a perspective representations of the design shown in FIG. 1 shown in greater detail.

Referring in FIG. 1 of this disclosure, this figure provides a perspective representation of an exemplary embodiment of a 1 U rack mount chassis 100 that employs Ammonia Nickel Loop Heat Pipes to cool a pair of hot running CPUs. FIGS. 2, 3 and 4 are perspective representations of the same design shown in greater detail. Many of the drawings and figures include oblique perspective 3D views of full scale devices that we have experimented with or modeled and were designed to prove the concepts contained in this document. Frequent reference will be made to the specific exemplary embodiments presented of devices that demonstrate the principles claimed, but it is to be understood that the claims and inventions are not limited to the specific exemplary embodiments used to demonstrate the claims and concepts. Nor are the Loop Heat Pipe Like devices referred to limited to Loop Heat Pipes or for that matter the Ammonia Nickel Loop Heat pipes shown in all but one of the figures, but can include other Loop Heat Pipes made of different materials that employ different working fluids that have been described in prior art and publications.

Contained within the 1 U rack mount chassis 100 is a pair of CPUs that are mounted on a PC server motherboard 107 that are being cooled by a pair of in this exemplary embodiment, Ammonia Nickel LHPs whose evaporators 101 sit on the CPUs being cooled and whose working fluid is being cooled and condensed from a gas back into a liquid by the a condenser 104 using cool air flowing through the chassis by the exit blower 105 that is normally employed to pull air through 1 U chassis. The device being used to pull air from a chassis can also be a 1 U fan. This exemplary embodiment illustrates how the existing fan that comes with a 1 U chassis can also be used to cool a pair of CPUs using a condenser whose details are discussed below. This figure also calls out the condenser line 103 that returns the condensate back to the evaporator and the condenser line 102 that transports vapor from the evaporator to the condenser. The sharp angle shown in the drawing where the condenser line 102 attaches to the evaporator body 101, in the devices we used, was rounded. Also called out in this figure are the power supply 106, the rear wall of the 1 U chassis, 108, and the exhaust port employed by the blower, 109.

In this exemplary embodiment the rear exhaust device 105 that already is a part of existing 1 U chassis designs is used to cool both processors eliminating the need for between four and eight CPU cooling fans that are needed when heat exchangers are mounted directly on top of CPUs. This reduction in components, points of failure, noise and the need for electrical power is made possible by the passive nature of the loop heat pipes employed along with the use of a condenser whose finned heat exchanger has a much larger area than the fins typically used to cool these CPUs when they are mounted on a base plate that sits on top of the CPUs. It is this increased fin area that dramatically reduces the need for high speed air to cool the CPUs. The rear region of the 1 U chassis is being accessed here using LHP condenser tubing whose OD can be as small as 0.1" and carries the hot vapor that is being extracted from the wick inside of the LHP evaporator that is thermally attached to the CPUs and carries this vapor to the condenser where the heat it carries gets exchanged with the air flowing out of the chassis just before it leaves, eliminating recirculation within the chassis, reducing the need for increased air cooling velocities, all of which combine to make it possible for a single blower to cool a pair of CPUs.

FIG. 2 is a more detailed view of the exemplary embodiment shown in FIG. 1. In it we can now see all four of the condenser lines used to connect a pair of LHP evaporators with their condensers. In this figure the liquid return lines 103 and the vapor exhaust lines 102 can be clearly seen as well as the fins at the bottom of the condenser.

FIG. 3 is an even more detailed view of the exemplary embodiment shown in FIG. 1 in which we have exposed the left hand CPU 110 by eliminating the heat spreader 101 seen covering the right hand CPU 111. This figure also calls out the four screws that are exemplified by 112 that are used to clamp both heat spreaders to their CPUs as well as the evaporator shells 101 that contains the wick structure that pumps the primary coolant passing through the LHP and also exchanges heat between it and the CPU being cooled.

FIG. 4 is the first of many exemplary embodiments of a three piece condenser. All of the exemplary embodiments in FIGS. 1 thru 6 uses three piece condensers similar to the one pictured here. In this exemplary embodiment, the finned portion of the condenser becomes semi-permanently attached to the base of the 1 U chassis, greatly simplifying the removal of CPUs. This condenser design makes it possible to remove one or both CPUs by first removing the screws 117 and studs 114 that provide the pressure required to get good thermal contact between the condenser tubing 113 and the base plate of the heat exchanger 115 using a clamping plate 116 that can be easily removed to make it possible to remove heat spreaders 101 (in FIG. 3) that clamp the evaporator section to the CPU without removing the bulk of the condenser's body.

Figure 5:
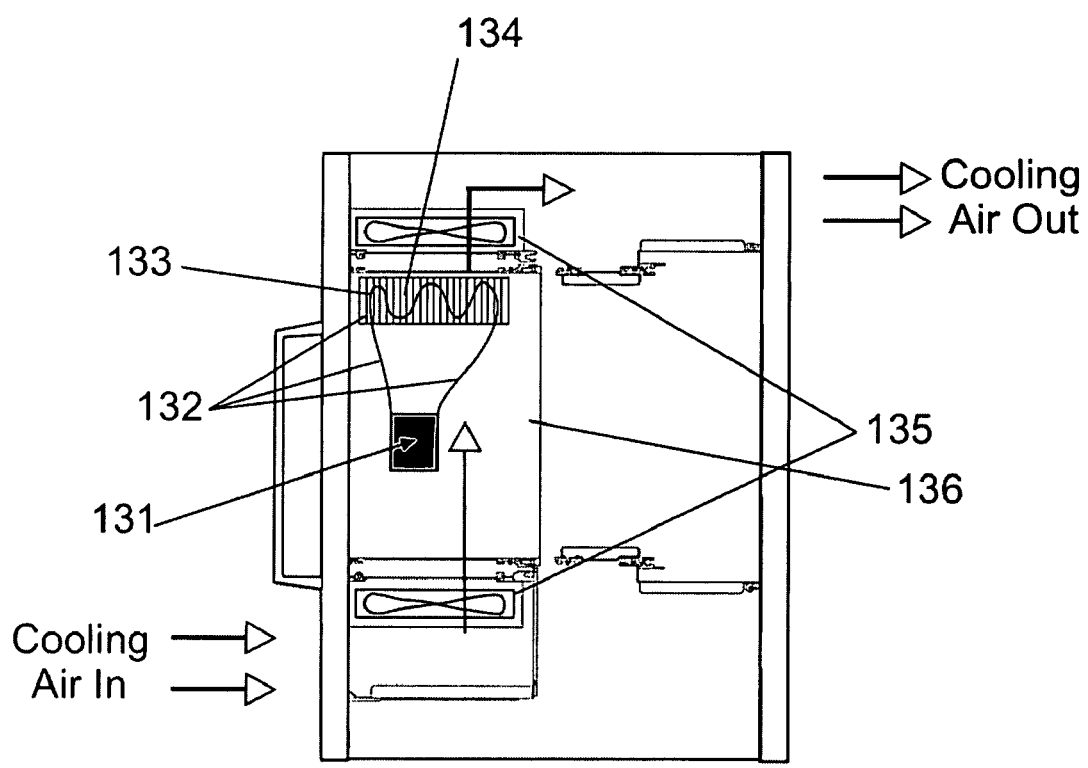
FIG. 5 is a sketch that demonstrates where to locate an LHP and its exit flow condenser used to cool SBC (single board computer) cards in a typical COTS (i.e. PICMG, VME or similar chassis) chassis that contains semiconductor devices that reject large quantities of heat.
Figure 6:
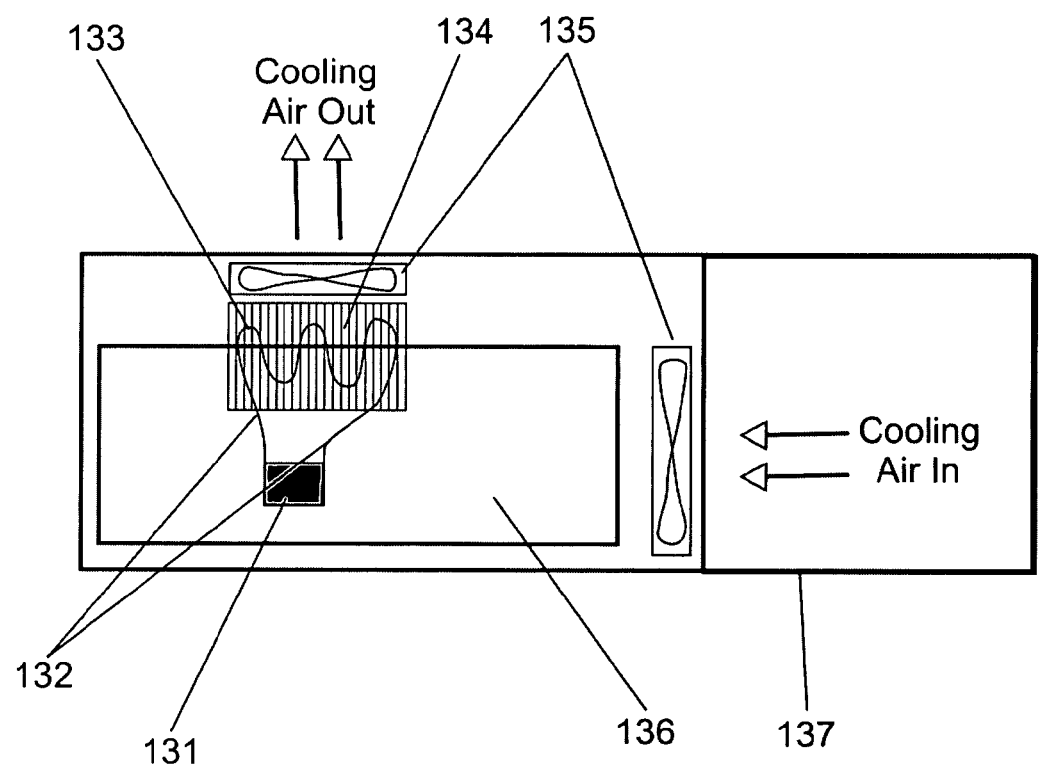
FIG. 6 is a sketch which demonstrates one method of cooling a PC chassis that contains an add in card (i.e. ISA, EISA, PCI, PCIe, HTX or similar) located in an "I/O" channel that contains a component which rejects a lot of heat and is cooled by an LHP and its condenser.

FIGS. 5 and 6 are sketches that demonstrate where to locate exit flow condensers used to cool SBC (single board computer) cards and similar devices upon which are mounted semiconductor devices that reject large quantities of heat, including but not limited to high power CPUs, GPUs and FPGAs all of which are designed to slide or fit into a chassis that includes some sort of backplane that connects these cards to either similar devices in the system or a motherboard. The cards that we are typically talking about include COTS style cards one well known form of which is called PICMG used in standard systems that are not limited to the ISA, EISA, PCI, PCIX or PCIe busses, even though these have become the standard and most popular busses for interconnecting such devices. Either of the techniques could also be used to cool what are today referred to as blades—PCBs that slide into blade chassis and which like COTS cards typically use card edge guides to guide them into a rear mounted backplane for which there is no common interconnect standards. Blades turn out to be just another form of SBC used in HPC (high performance computing).

In the case of a blade or SBC card mounted in a COTS or Blade chassis, an air path is normally provided for cooling which directs the air across the board in either a vertical or horizontal direction. Normally, COTS style SBCs are housed in special chassis. The solutions described herein could be used in situations where multiple rows of blades are cooled by air that is directed vertically through a plurality of them.

The ideal location for an LHP air-cooled condenser in this exemplary embodiment of the invention is at the location where the air normally exits the blade. FIG. 5 is a side view of an industry standard COTS PICMG chassis taken off of the web. In this commercial design a pair of fans (135) are used to bring air in below a CPU card (136) and pull it over the card and then exhaust it vertically. The route used causes the air to flow over the other components in the card before flowing over the LHP evaporator (131) that is mounted on a hot component like a CPU before flowing over the finned heat exchanger (134) that forms half of a split condenser whose other half is a serpentine shaped condenser line (133) that is connected to the evaporator with a pair of lines (132). The rising air leaves the region of the processor card helped by the second fan in this push pull arrangement.

FIG. 6 uses a similar technique to cool cards installed in the I/O channel of a typical PC motherboard installed in a PC desktop chassis that is shown lying on its side. In this case a heat exchanger is mounted between the top of the card and the chassis cover (i.e. top), which has been fitted with an exhaust fan that pulls air out of the I/O channel section of the chassis. The PC chassis (137) has a front section that normally contains hard disks and peripherals that gets followed by one or more fans (135). The air leaving the fans in the mid section of the chassis then enters the motherboard cavity of the box that also contains the peripheral interface cards (136) that get plugged into its "I/O Channel." FIG. 6 shows an I/O channel card in outline (136) that has a hot component on it that is thermally attached to an LHP evaporator (131) that employs a pair of condenser lines (132) to feed vapor to a condenser before returning liquid back to the evaporator. The serpentine (133) portion of the condenser is symbolically located as well as the air-cooled fins (134) that condense the vapor back into a liquid before returning it to the evaporator. Directly above the fins is a fan that exhausts air out of the box through the cover.

Figure 7:
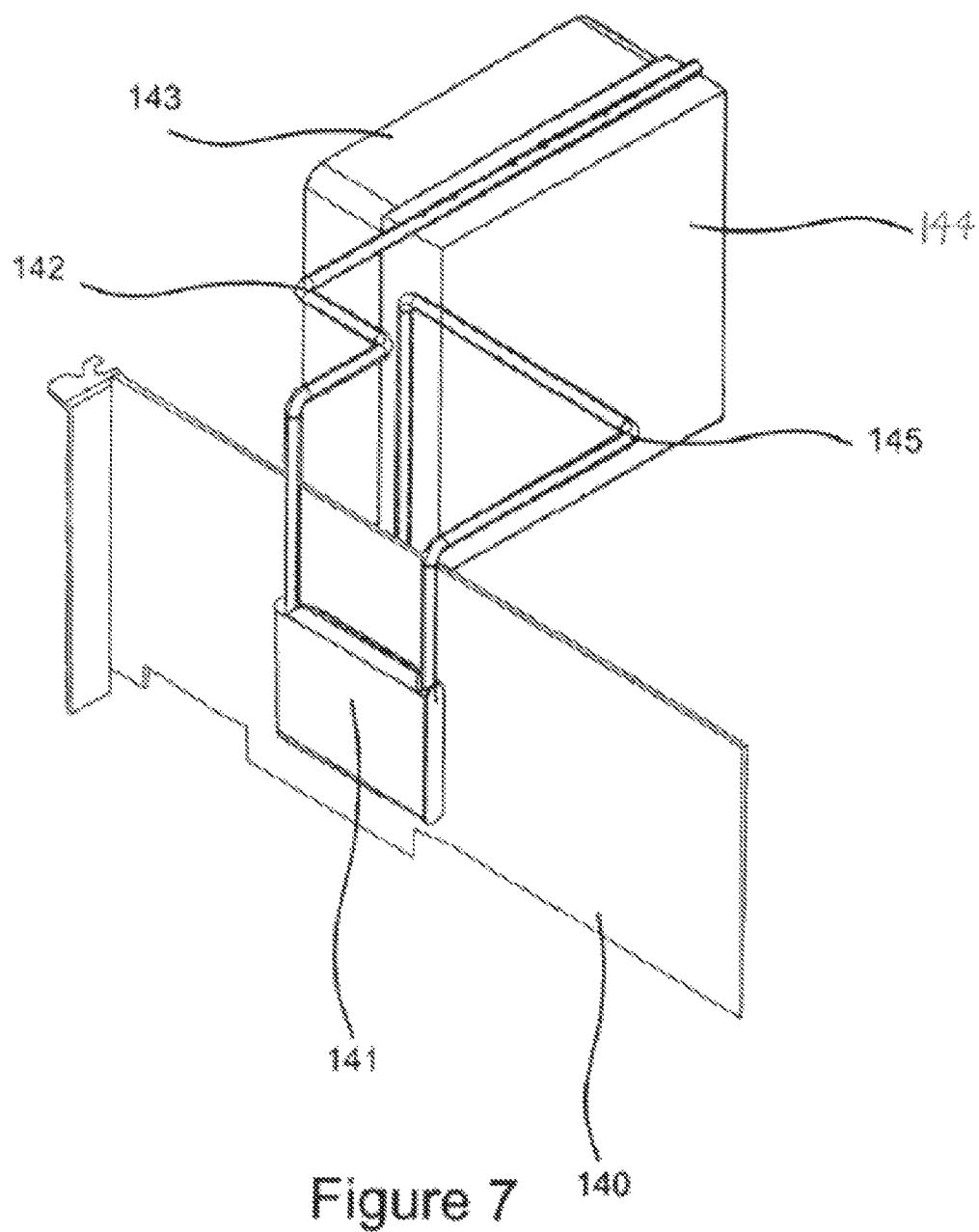
FIG. 7 is a perspective drawing of a PC add in card that is cooled by an LHP whose condenser fan is located on the rear wall of a chassis.

FIG. 7 is a 3D rendering of an exemplary embodiment of a PCIe card 140 that contains a hot device mounted to it that is being cooled using and LHP and exit flow cooling. The exit flow fan 143 in this case gets mounted in most PC chassis on the rear wall of the chassis and employs a 120 mm device to remove hot air from the chassis. The LHP evaporator 141 that is attached to the device(s) being cooled employs a pair of condenser lines: 145 carries the vapor from the evaporator to the condenser 144 while 142 returns the condensate back to the evaporator.

Figure 8:
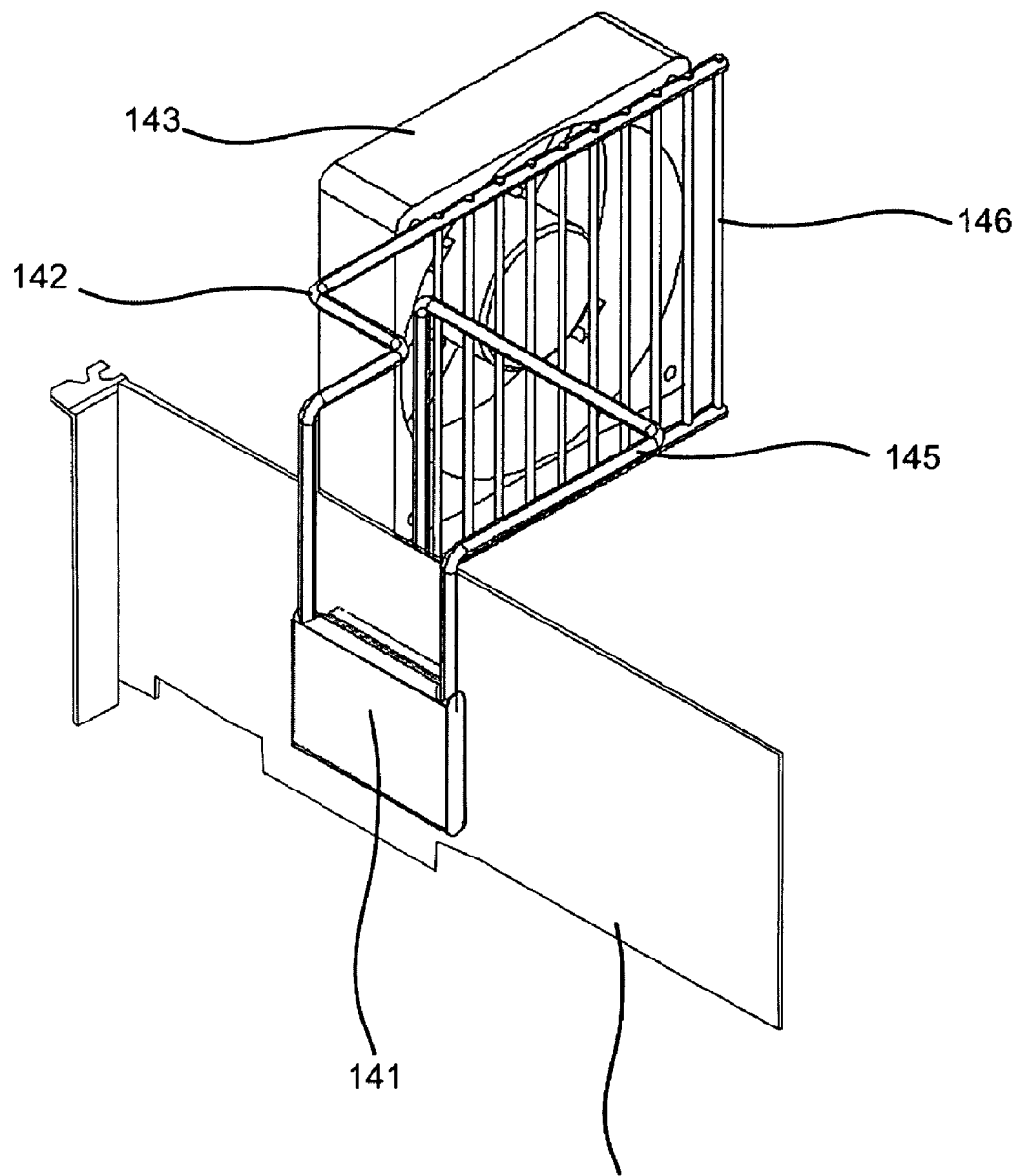
FIG. 8 shows in detail the LHP condenser shown in FIG. 7, including the fan used to pull air through the condensers cooling fins and a low pressure drop manifold within the condenser that improves the performance of a water copper Loop Heat Pipe.
Figure 9:
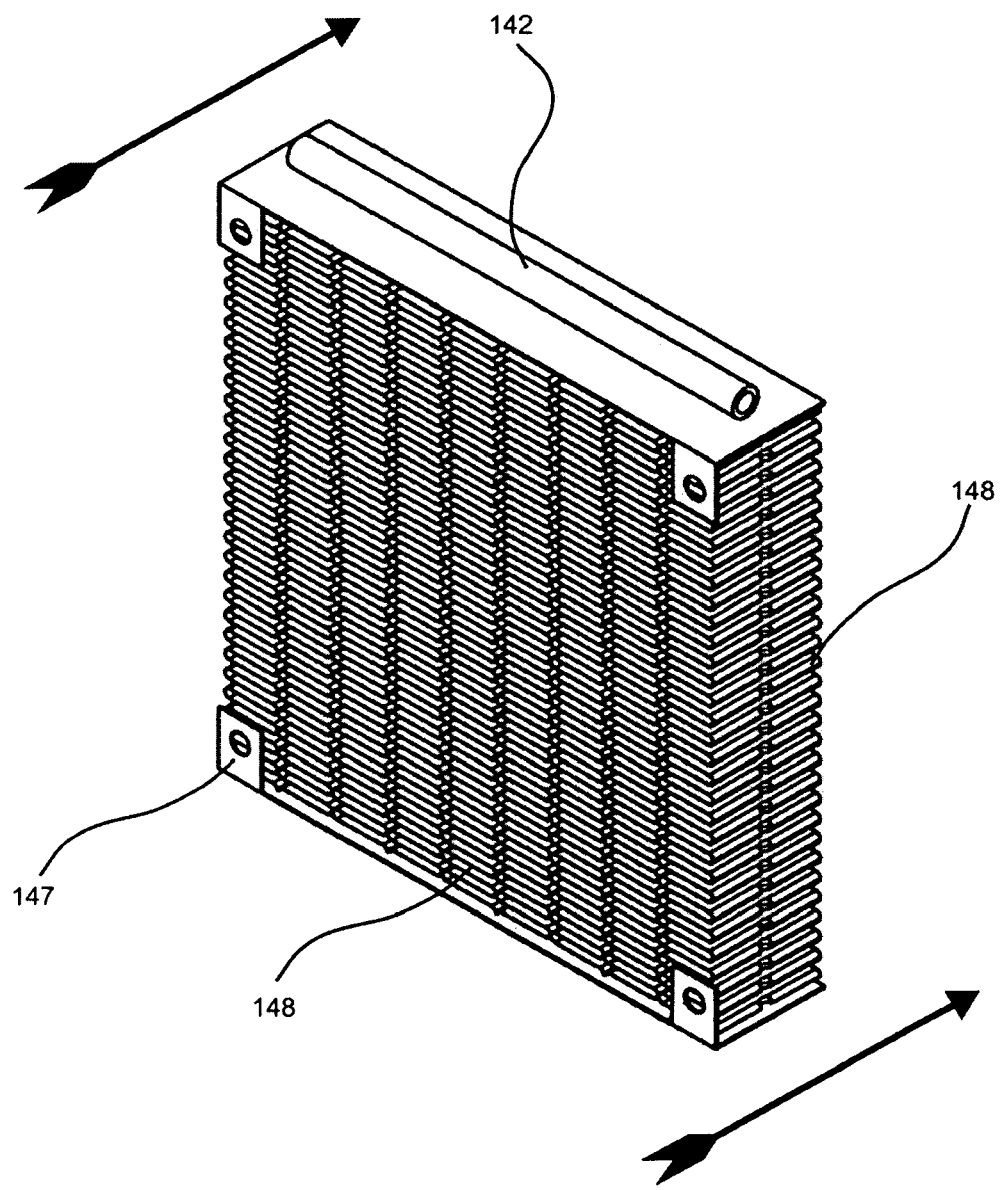
FIG. 9 is a perspective representation of a copper ribbon fin heat exchanger employed by the design shown in FIGS. 7 and 8.

FIG. 8. is a 3D rendering of the same exemplary embodiment shown in FIG. 7. In this drawing a plurality of vertical condenser lines 146 feed the vapor being condensed through the copper ribbon like fins of the exchanger whose approximate details are depicted in FIG. 9 along with the bolt holes 147 that attach the condenser to the fan that draws air through it and expels out of the chassis. Some details of the fan, 143, can also be seen in FIG. 8.

This condenser design employs a series of ribbon like fins seen in FIG. 9, 148, that are thermally attached to the small condenser tubes 146 that sit in the middle of the ribbon like fins which lie in a plane that is perpendicular to the axis of the air flow (depicted in FIG. 9 with large arrows). The plurality of condenser tubes makes it possible to spread the heat being rejected to the plurality of fins without having to use the technique that has been used in the past (i.e. adding ordinary heat pipes that get used to distribute heat within a heat exchanger), taking advantage of one of the major benefits of LHPs over standard heat pipes, and that is the ability of the wick to drive its vapor long distances, which in this case makes it possible to distribute the heat over a huge area of fin like devices that get used to transfer the vapor's heat to the air passing through them. In general, there are two features of condenser design that need to be taken into account in any LHP application. The first is adequate contact area: a condenser design that does not have adequate contact area between the primary vapor and the secondary coolant condensing the vapor will end up not condensing all of the secondary coolant back into liquid when the power being rejected exceeds a critical value. When this point is reached the LHP shuts down. The other is thermal resistance. The total thermal resistance of Loop Heat Pipes and LHPLs is essentially the sum of the thermal resistance of the evaporator and the condenser. Distributing the heat over a large area of fins minimizes the thermal resistance of the condenser helping to improve the overall efficiency of the LHP. This particular condenser has been used to reject up to 600 Watts of power, and while it doesn't have the lowest thermal resistance of the condensers we experimented with, it is ideal for high power devices being cooled by air.

Figure 10:
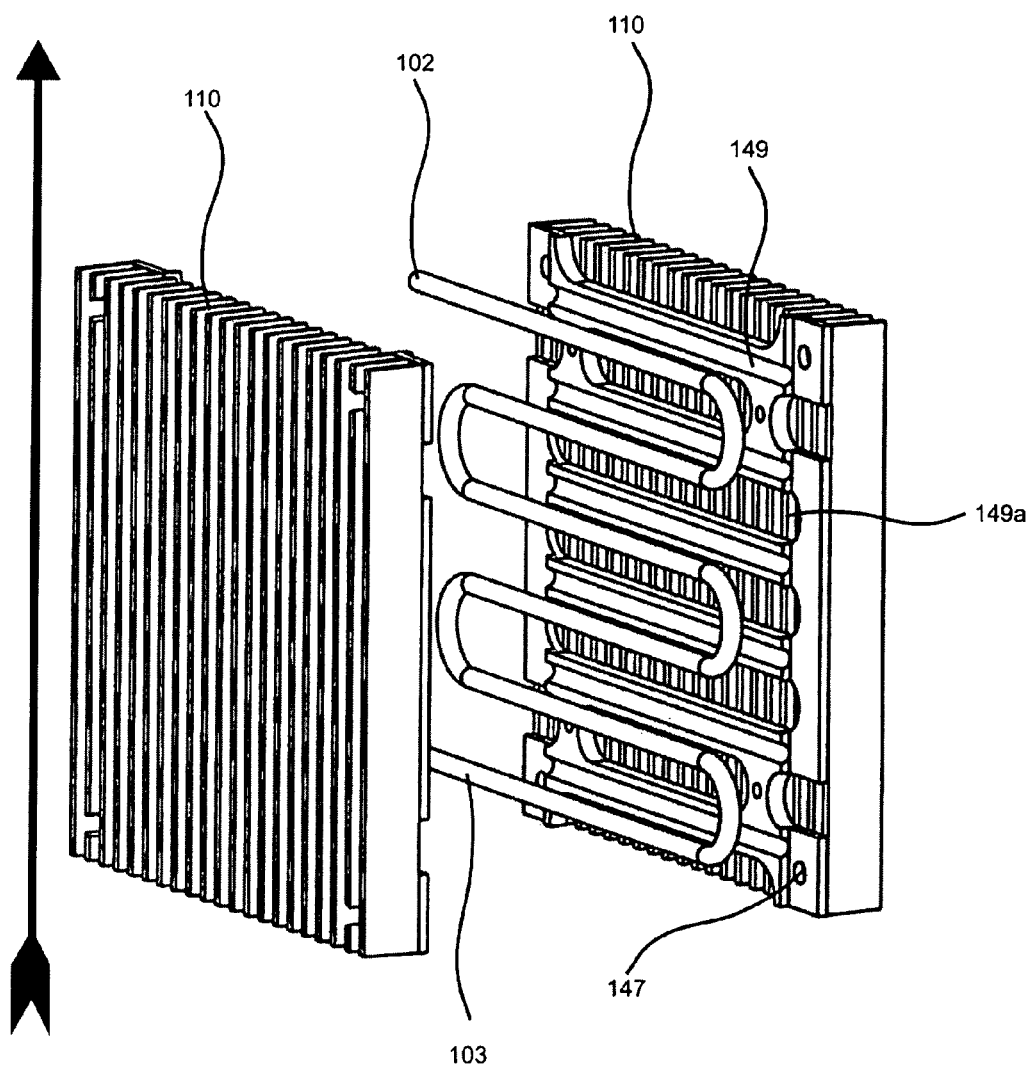
FIG. 10 is a perspective drawing of a set of Aluminum fins that have been arranged to provide counter flow cooling with air running the length of the fins cooling a serpentine LHP condenser pipe.

FIG. 10 is an air-cooled condenser designed to fit into rack mount chassis, such as the 1 U chassis shown above in FIG. 1 . . . 4. This condenser has been designed for minimum thermal resistance employing a technique that we will also employ below in two other designs. The definition of the thermal resistance of an LHP involves only a pair of parameters, the delta T between the device being cooled and the outlet temperature of the secondary coolant that the condenser emits, divided by the power in Watts that is being transmitted by the device. The goal in any LHP whose thermal resistance we desire to minimize requires us to minimize the delta T between the device being cooled and the secondary coolant. This can be restated when it comes to the condenser, and that is the design that maximizes the temperature of the coolant will minimize the delta T. To maximize the coolant temperature one of the things we need to make sure is that the hottest primary coolant (i.e. the vapor leaving the evaporator) that enters the heat exchanger come into contact with the secondary coolant just prior to its leaving. In addition, if we really want to increase the temperature of the effluent we need to eliminate conduction paths which make it possible for the hot side of the condenser to be cooled by the cold side, which in this case is the side that first comes into contact with cold air. The design in FIG. 10 employs these general principles.

FIG. 10 is a 3D exemplary 3D rendering of an efficient counter-flow style air-cooled condenser. The condenser lines are arranged so that the vapor inlet 102 is at the exhaust end where the air that is traveling up the cooling the fins 110 leave the two finned halves. The primary coolant leaves the condenser pipe at 103 and then moves back to the evaporator. The two halves clamp together using bolts that are inserted into the left half and engage threaded holes on the right side (seen here) labeled 147. The condenser lines make thermal contact with the two halves in machined out groves 149 whose contour has the same radius as the condenser line. To help reduce thermal conduction from the hot end of the condenser fins (at the top in FIG. 10) the base plate that the fins attach to has been hogged out with a plurality of channels 149a that cut through the based plate. The direction of the air flow is vertical and is indicated by the large arrow.

Figure 11:
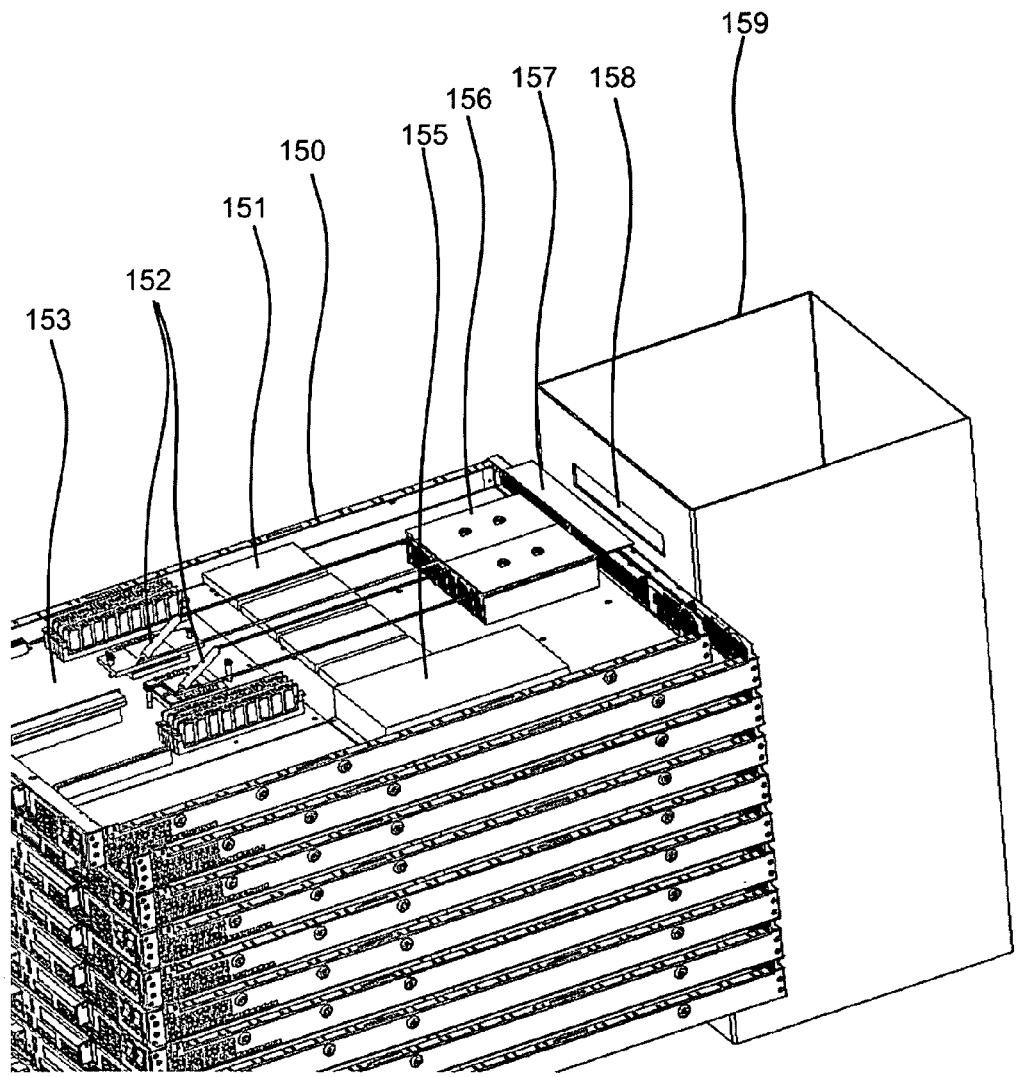
FIG. 11 is a perspective drawing that shows a stack of 1 U rack mount chassis, whose top most chassis is in the process of engaging an air duct used to remove air from all of the chassis in a rack cabinet.

FIG. 11 is a 3D rendering of an exemplary embodiment of a plurality of 1 U rack mount chassis that are being 100% air-cooled using a duct to draw air out of the chassis. The scheme employed is not limited to 1 U chassis, but can be employed by rack mount chassis of any height (1 U, 2 U, . . . NU, etc.). This approach eliminates the need for the exhaust fans employed in FIGS. 1 through 4, all of which employed either the 12V blowers or fans typically used to extract hot air from rack mounted chassis. The use of 12V fans to remove air is wasteful, as the power is most often provided by a power supply that converts AC to DC voltages. Such conversions are never 100% efficient and in general, employing power supplies within rack mount chassis to carry out unnecessary conversions is wasteful. The proper way to evacuate such a duct is using large AC fans located somewhere else in the system. A convenient way to evacuate such a duct is employing the large AC fans that often are mounted on the rear doors of a rack cabinet. Adding plenums (not shown in these drawings but obvious to anyone familiar with the art of fabricating ducts) that connect the duct to these fans is a simple way to simultaneously cut our recirculation within the rack cabinet and at the same time improve the performance of such fans. When this method is combined with water-cooled air heat exchangers placed in the path between the chassis and the duct, it makes it possible to return ambient air to the room eliminating the need for expensive refrigeration units that also take up a lot of space. The duct 159 in this exemplary embodiment has the air within it exhausted by a connection to some negative pressure source below the duct that in the case of an air-cooled data center that relied on its main water chilled heat exchanger only could be the main HVAC return line. The only difference between this exemplary embodiment and one that employed a vertically rising air column would be the orientation of the sheet metal tabs that get described below which get used to seal the duct when a chassis is removed. One of the most important features of the exemplary embodiment is the fact that there exists a seal between the chassis and the duct (typically a crushable material) as well as a method for closing off the slots in the duct that the air is being pulled through when a chassis is removed. One of the main benefits to the cooling of components within the electronics contained by the chassis is the ability to employ bleed air-cooling (i.e. admitting cool air into the chassis through vents placed about the chassis) that is not possible in a typical rack cabinet for the simple reason that there is no guarantee that the air that surrounds a chassis on its sides is cool. In fact, just the opposite, circulation paths frequently set up within rack cabinets about the chassis contained within that allow the hot air at the rear to make its way back to the sides and front. The system within the 1 U rack mount chassis in this exemplary embodiment is virtually identical to the systems rendered in FIG. 1 . . . 4, employing a pair of LHPs whose evaporators 152 are seen along with the motherboard 153, a power supply 155, four hard disks 151 one of which is called out along with the chassis frame 150 and the split condenser 156 and the horizontal tab 157 that opens the blade that seals the slot in the duct 158 when the chassis gets fully inserted into either an open rack or a rack cabinet.

Figure 12:
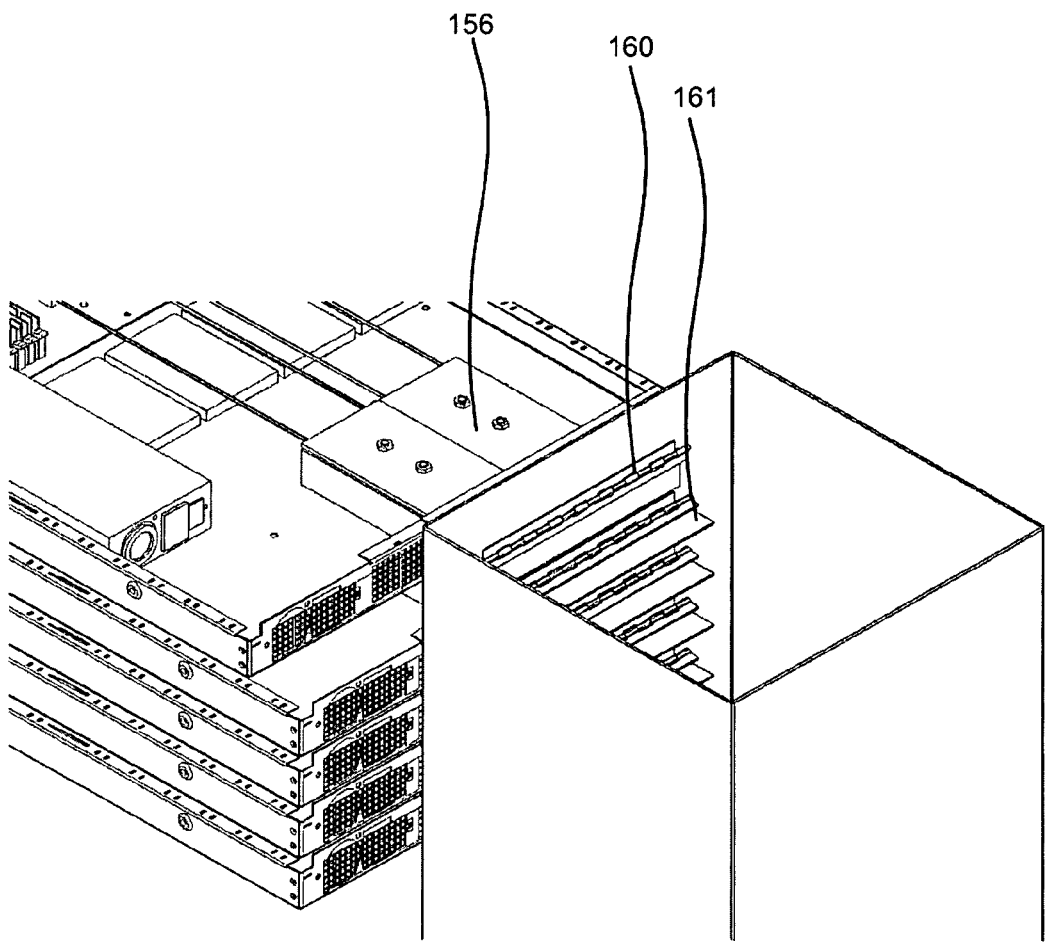

FIG. 12 is another view of the exemplary embodiment shown in FIG. 11. From this angle we can see the condenser 156 that is being cooled by the exit flow along with the hinge line 160 of the first spring loaded sealing plate 161 that is closed at this time because the chassis is not fully pushed into the rack or rack cabinet that holds it. The remainder of the duct sealing plates are pushed out into the air flow, enabling these other which chassis to exhaust their air into the duct.

Figure 13:
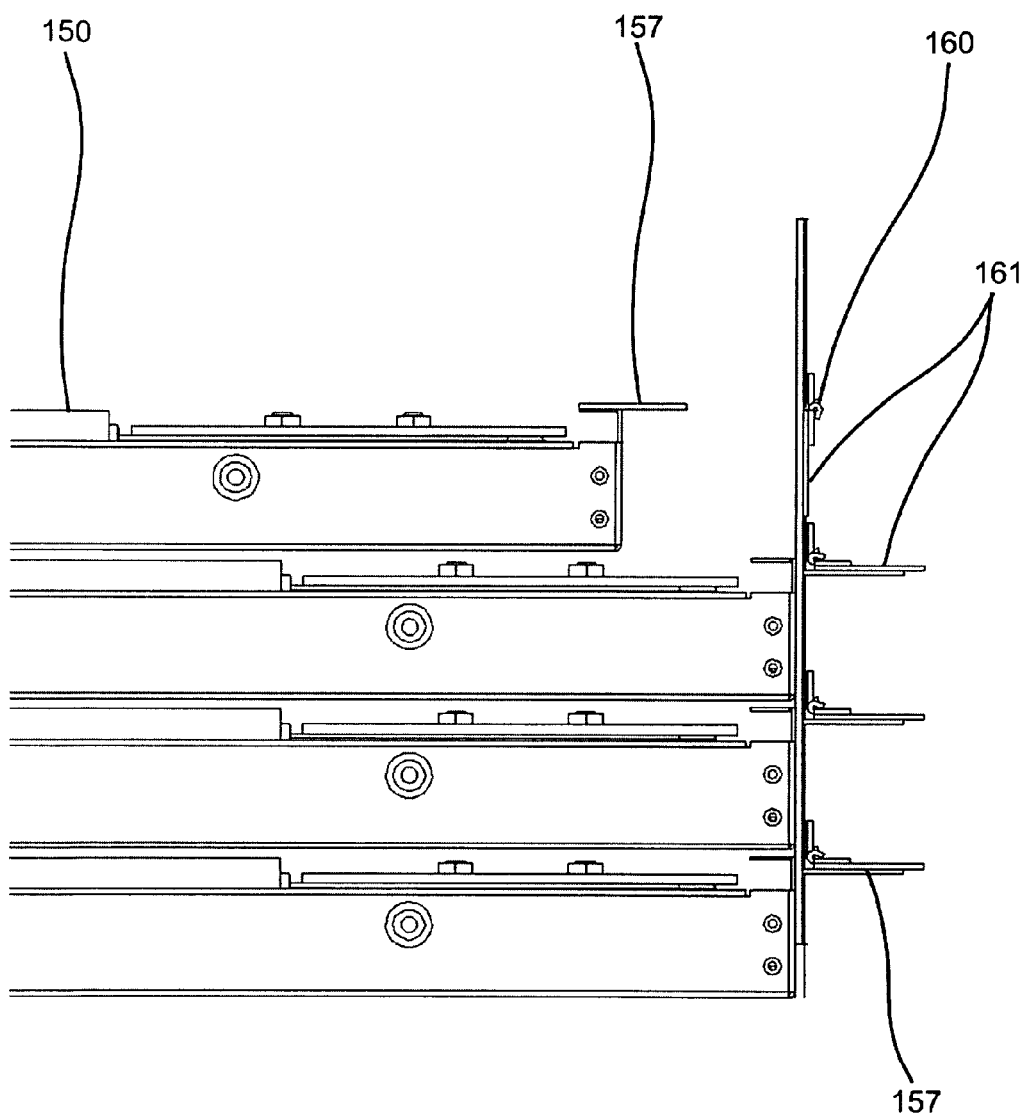
FIG. 13 is a cross section of the negative pressure duct shown in FIGS. 11 and 12 which demonstrates how a metal piece on the 1 U chassis forces open upon insertion, the spring closed flap which seals the duct when the chassis is not installed.

FIG. 13 is a side view of the exemplary embodiment shown in FIG. 11. The 1 U chassis 150 at the top of the stack of chassis can be seen to not be fully inserted into the open rack or rack cabinet. The horizontal tab 157 that gets used to push out the top duct sealing plate 161 along with the hinge line 160 can also be easily seen.

Figure 14:
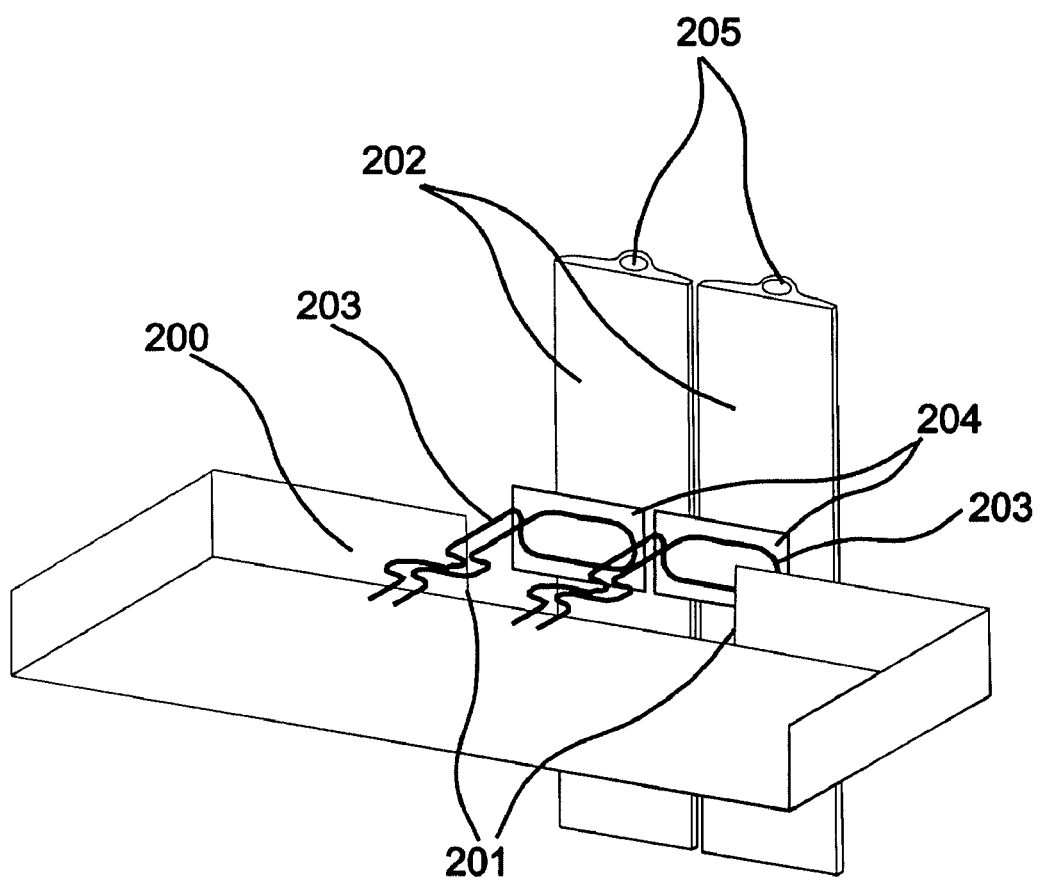
FIG. 14 is a perspective view of the rear of a 1 U chassis that contains an LHP whose split condenser protrudes out the rear and whose cold spreaders make contact with a vertically mounted water cooled cold plate mounted inside of a rack cabinet.

FIG. 14 is the first in a series of exemplary embodiments of what we call a split condenser. There are a number of issues that suggest that this is a good approach to cooling electronic devices that need to be "hot swapped" into and out of chassis that enable cards or chassis to be installed and removed while the remainder of the cards or chassis in a plurality of such devices continues to run. This method makes it possible to make and break thermal connections whose source of cooling is a chilled liquid, such as water without actually making or breaking the interconnect of a pipe that is carrying a liquid. In this first and simplest exemplary embodiment, a 1 U rack mount chassis 200, whose height is 44.5 mm and which has a slot 201 cut in its rear that in this case just happens to be 150 mm wide and is being cooled by a pair of split condensers, whose LHP condenser pipes 203 return back into the chassis from presumably its rear where they presumably cool a pair of hot running electronic devices. The dimensions of the chassis and the other components are not relevant to the explanation of the exemplary embodiment and need to be adopted to the particular situation by a chassis and thermal engineer familiar with all of the details. A chilled liquid flowing through vertically oriented pipes 205 located in the rear of a rack cabinet behind the chassis being cooled is used to cool a pair of vertical cold plates 202 that are thermally attached to a pair of cold spreaders 204 that are thermally attached to a pair of condenser pipes 203 that are thermally attached to them. There is no reason why the cold plates and their supply lines could not run horizontal. This exemplary embodiment did not include a convenient method for clamping the cold spreader against the cold plate that is cooling it, rather we employed a pair of bolts and nuts that were mated to holes in the cold plate (not shown). The clamping arrangement is an important part of the overall design, as it is needed along with a thermal interface material that helps make good thermal contact between the cold plate and spreader, for the apparatus to work. The design seen in FIG. 14 was implemented, and it was discovered that for copper cold plates and an aluminum heat spreader whose area was 3 square inches the upper limit that could be cooled when this split condenser was used with an LHP evaporator that we later discovered was potent enough to service a 320 Watt load, was 80 Watts. This demonstrates the importance of condenser design in LHPs and LHPLs, and suggested that we needed to increase the contact area in split condensers, which is what the following split condenser exemplary embodiments all do.

FIG. 15 shows a split condenser whose contact area between its cold plate and cold spreader is much greater than that depicted in FIG. 14. The cold spreader 204 that is in contact with the condenser lines 203 is actually a component that is part of a rack mount chassis (not shown in this figure) that is being inserted into a rack cabinet in a direction that is parallel to the large arrow drawn. Air whose direction of motion is also called out by the large arrow is being either drawn or blown through the air heat exchanger one of whose plurality of fins 209 can be seen in FIG. 15. The fins of this heat exchanger are cooled by virtue of the fact that their base is in thermal contact with the bottom plate of the cold plate whose upper plate is called out as 202. As it exits this particular split condenser (but not necessarily the chassis) exemplary embodiment it passes through a finned heat exchanger 209 that in this case sits below the cold plate 202. The split condenser does not need to employ a liquid assisted air heat exchanger, but can be created using a pair of cold spreaders both of which are used to cool LHPL evaporators or possibly a pair of air heat exchangers, depending on the nature of the devices housed in the rack mount chassis can contain any combination of primary and secondary heat loads. The cold plate in this instance is formed from a pair of identical metal pieces that may be sandwiched around a U tube through which a chilled liquid flows. In this possible exemplary embodiment the chilled liquid can be seen entering the cold plate 202 through a U shaped pipe 205 which exits the cold plate at 208. When the cold spreader and finned heat sink within a chassis in this particular exemplary embodiment passes over the cold plate, six bolts whose precise number is again a function of the mechanical design and the size of the split condenser that employ springs 211 shown in FIG. 16 get used to pull the cold spreader down on top of the cold plate when it is being inserted. The cold plate has slots 206 that makes it possible for the cold plate to enter the female cavity without hitting the clamping bolts 210. The cavity is prevented from closing up and preventing the cold plate from entering by six sleeves 212 seen in FIG. 16. A second set of identical chilled liquid pipes are drawn to the left but not labeled. There is nothing unique about the particular way in which the cold plate is fabricated. It could just as easily have been cooled using a single entrance and exit pipe that fed a serpentine section of pipe instead of a U channel or a channel that was machined inside of the cold plate that was intended to provide a counter-flow cooling path. The choice of the precise method used to cool the cold plate is a function of the design constraints, including the cost, heat being rejected and thermal resistance. There is also no need for the split condenser to sit inside of a chassis, it can be located behind the chassis in the rack cabinet and there is also no need for the male portion to be a cold plate: it is possible to employ a variation of the design in which the LHP condenser tubes are embedded within a male device that gets inserted into a pair of female cold plates.

FIG. 16 provides the details of a one of many possible mechanisms that can be created to apply clamping pressure between a pair of female plates. The bottom plate in this exemplary embodiment could be a spreader plate (we did not draw any condenser lines on it for this case) or a shim plate that was used with an extruded air heat exchanger that is ultimately in thermal contact with the cold plate. For the cold plate 204 to be easily inserted between the cold spreader 202 and the bottom plate 213, it is necessary to provide an inclined plane whose surface is "greased" with a thermal bonding material. As the cold plate rides into position (and the motion in the case we are dealing is relative, the actual motion comes from the chassis being inserted: the cold plate is fixed and enters the female section as the chassis that contains it is inserted into a rack cabinet) the inclined planes of all four surfaces exert vertical pressure on each other which is resisted by a set of six springs. The bottom shim 213 of the heat exchanger in this exemplary embodiment is attached to the chassis. For this scheme to work, the height of the cold plate needs to be correctly set up so that at the end of the travel it comes into contact with the shim, as neither have a lot of vertical freedom. The upper cold spreader, though, is free to move up and down, easily bending the LHP condenser lines 203 which are both small and fairly flexible. The vertical clamping pressure is provided in this exemplary embodiment by six bolts 210 that pass up through six springs 211 before passing through the bottom plate 213 and a set of six sleeves that guarantee that the gap between the top 202 and bottom 213 of the female cavity stays open. The top of the bolt 210 has a shoulder and a smaller threaded section. The shoulder, screw and nut 207 make it possible to fix the end of the bolt to the cold spreader plate 202. When the cold plate is inserted, the springs allow the cold spreader to rise, while at the same time providing vertical clamping pressure on the entire assembly.

FIG. 17 provides an oblique 3D view of the split condenser design detailed in FIGS. 15 and 16 placed inside of a 1 U rack mount chassis. In this exemplary embodiment two LHPs are being cooled one of which 214 is called out. The bottom half of the figure is identical to the top, and shows the same units after the cold plate is fully engaged. The total number of LHPs used to cool primary heat loads is a function of the number of motherboards being installed in the rack mount chassis: using current motherboard designs up to four processors can easily be mounted in a 1 U chassis and eight in a 2 U tall chassis. In FIG. 17 the bottom chassis has been fully inserted into its location in a rack cabinet or rack, as can be seen from the fact that the split condenser's cold plate is fully inserted within the combination cold spreader/liquid assisted air heat exchanger. This chassis happens to be a 1 U rack mount design, but the size of the rack mount chassis is not fixed: the chassis employed may be smaller or larger. Care has not been taken in this figure to make the modifications to the chassis that one might make to improve its cooling performance. For example, the rear wall of the chassis contains breathing holes in it that are left over from the normal manner in which power supplies get installed (i.e. near the rear wall). The drawing calls out one of four hard disks 215 and a pair of standard high speed 1 U fans, one of which is labeled, 216. These figures do not show a baffle that couples the fans to the air heat exchanger that forms the lower half of the female split condenser. In the top half of the figure, the cold plate can be seen entering the heat spreader air heat exchanger combination as the chassis gets inserted into a rack cabinet that contains a cold plate mounted on pipes. Some additional supporting structure for the cold plate will probably need to be provided as well. The cold plate is stationary and is permanently attached to a pair of chilled liquid pipes that typically would reside within the rack cabinet behind the chassis (see FIG. 20). The bottom half of the figure shows the chassis fully inserted into the heat spreader air heat exchanger split condenser combination. In situations where there is adequate air flow leaving the chassis and fin area between the air leaving it and the fins, this particular arrangement is one of those that makes it possible to return the air leaving the chassis to the ambient temperature of the air in the room eliminating the need for refrigeration units that take up space in rack mount chassis in situations where the heat being rejected within a rack cabinet exceeds 25 KW. Again, we should point out that split condensers are not limited to rack mount chassis and when used in rack mount solutions are not limited to 1 U chassis.

FIG. 18 is an oblique view of a similar exemplary embodiment of the same split condenser, in which we almost seal the chassis off from the air in the room or the rack cabinet. One of the goals of this design is to let ambient air into the chassis proper slowly and not to employ ambient air in the cooling scheme. The large arrows seen within the region of this 1 U rack mount chassis depict the circulation pattern of the air within the chassis. A pair of fans 216 sucks air through the split condenser air heat exchanger that is no longer called out but whose fins can easily be seen sitting beneath the remainder of the split condenser. In this figure we are primarily calling out new features that have not been presented in the prior split condenser designs that start with FIG. 15 and end with FIG. 22 below. The fans are interfaced to the split condenser using a baffle not depicted here. The airflow pattern is created using a containment baffle 217 that forces the air leaving the fans to travel to the front of the chassis before being sucked back to the rear of the chassis after it passes around the baffle. The airflow is helped by the positioning of the power supply 218 whose fans accelerate the air passing through before it turns the final corner and again passes through the finned heat exchanger that is part of the split condenser depicted in FIG. 18. This chassis partially isolates the internal air within the chassis from the air within the room and rack cabinet. In the rear, a plate 219 that is attached to the cold plate's water supply lines 205 and 208 has been added to seal the back slot in the chassis using a compression gasket at the point where the chassis is fully inserted into the rack cabinet and the cold plate is fully inserted in the split condenser. While this chassis does employ several fans, some of which might need to run at high speeds, it still consumes much less energy than a typical 1 U chassis, that can require as many as 18 fans to cool the electronics. This energy savings is a direct result of the fact that the primary load of the unit amounts to over 60% of the heat being rejected and this heat is being directly rejected to a chilled liquid instead of air. Not only that, the air that is circulating within the chassis will have very little need to leave it, eliminating the need for air-cooling outside of the chassis. This eliminates the energy typically expended within rack cabinets and the data center room to move air while at the same time eliminating the need for large heat air heat exchangers located within or adjacent to the rack cabinet to handle the high heat loads that densely packed rack mount chassis can produce. With new semiconductor devices hitting the market that reject as much as 500 Watts, it becomes possible to create 1 U rack mount chassis that reject up to 2 KW. Such rack mount chassis can reject up to 80 KW when installed in a 40 U tall rack cabinet. Solutions like the one shown in FIG. 18 are able to handle heat loads of this magnitude and are much more energy efficient than solutions which employ direct water cooling to cool CPUs instead of the factor of 100 more energy efficient two phase cooling provided by LHPLs. In addition, keeping the circulating air path within the chassis itself (instead of letting the air wander about a rack cabinet or out the rear door to the data center's CRAC unit heat exchanger) dramatically reduces the energy required to reject the secondary heat loads.

FIG. 19 is an oblique view of a section of duct 221 that may be used to exhaust the air out of a group of rack mounted chassis (not shown here). The design that is shown in detail in FIG. 20 employs a rack mount chassis, which may be 1 U tall, which may not need any fans at all within the rack mount chassis. This design provides secondary cooling using the duct to suck air through the chassis while at the same time cooling the air that passes through the air heat exchanger that is a part of the split condenser seen in FIG. 20. The primary and secondary heat loads are rejected using a plurality of chassis that employ a plurality of split condensers 202 that can be seen in FIG. 19. This particular duct employs the rack mount chassis seals described in FIGS. 11, 12 and 13. A pipe 220 is used to feed cold water to the plurality of cold plates seen and another pipe 222 gets used to return the hot water produced to the next cooling loop in the series that carries the rejected heat to the cooling tower. The pipes that carry the secondary coolant to and from the split condenser are labeled 205 and 208 as seen in FIGS. 15 through 18. The precise location of the pipes 220 and 222 within the duct is not important and can change as a function of many design parameters.

FIG. 20 is an oblique view of a 100% air-cooled plurality of split condenser equipped 1 U rack mount chassis, most of which are installed within either an open rack or rack cabinet (not seen) that employs a duct 221 to remove air from the rack mount chassis being cooled. The pipe 220 that feeds cold water to a plurality of cold plates 202 and the pipe 222 that returns the hot water to the next cooling loop, can also be seen. The top most 1 U rack mount chassis has still to be slid into place in the rack cabinet, making it possible to see its cold plate 202. Within the topmost chassis we have labeled the heat spreader 203, a hard disk 215 and an LHP that is used to cool one of the two processors being cooled in this exemplary embodiment. Also visible in this figure but not market are a second LHP, memory, power supply, three more hard disks and a motherboard. This system employs the 1 U rack mount to duct sealing method described above.

FIG. 21 depicts a pair of "blades," single board computers that are designed to slide into an enclosure that has a backplane 415 that is designed to accept mating sockets that provide the blade's PCB 402 with the power needed for its electronic components to function. This approach to split condenser design does away with a rear exit interface to a chilled liquid. What we do instead is employ cold plates 400 above and below each of the blades being cooled. These cold plates presumably receive their coolant from pipes that run up and down the sides of the enclosure used to contain the blades and which get delivered to them at the front (left side in FIG. 19) of the chassis, delivering the coolant to a channel in the rear before it leaves to go back to the return pipe. What makes the design unique and novel is the use of cold spreaders 401 that are made of U channels and which upon insertion of the blade into its enclosure, make contact with the cold plates, top and bottom. Once installed and seated in the sockets that mate with the backplanes 415, a scissors jack 407,408,416,417, 418,419 is employed to apply the clamping pressure to a spring 409 the cold spreader channel which is in thermal contact with both LHP condenser lines in this exemplary embodiment and standard heat pipes which are being used to cool DIMM modules with a copper heat spreader that fits over the modules and is thermally attached to them.

The upper portion of the figure is an end on view of the blades inserted into the chassis. The end view provides a detailed description of the cooling arrangement. A pair of cold plates, 400, each cooled by a liquid stream 403 is employed to cool the components on the blade employing a split condenser. The blade PCBs 402 slide into the enclosure using "card edge guides" 414 that are designed to both guide and hold the PCB as it slides into place. Between each of the card edge guides used by adjacent blade PCBs we have inserted a "U channel" 401, at both the top and bottom of the blade. These U channels provide the metallic component that defines the cold spreader and are in thermal contact with the cold plates, LHP condenser lines 412 and DIMM module heat pipes, 413. The blades are inserted into the electronic enclosures with their U channel cold spreaders 401 making light contact with the cold plates 400 that they will become thermally attached to after the board is completely inserted into the enclosure. For the channels 401 to make good thermal contact with the cold plates, 400, it is necessary to apply pressure to them.

In this kind of situation there are few possibilities for creating this pressure. The method we have chosen to provide the clamping pressure, which is certainly not unique but does demonstrate a possible approach, is to employ a scissors jack with arms 408. The jack is engaged using a knob 406 that comes out the front of the blade and uses a shaft 407 and threaded nuts 417 to squeeze the two arms 408 of the scissor together, creating a vertical compression stress on the springs 409 that in turn is applied to the channels 401. The squeezing action is effected using a pair of threaded nuts, 417, one of which is called out and is opposed by a second in each jack. As the threaded section of the shaft 416 turns the two nuts 417 get pulled together putting opposing forces on the springs, 409, one of which is being used to exert pressure on each of the cold spreaders 401. The sleeve 419 rides up and down on a vertical shaft not called out which attaches at its end to a cold spreader with a female attachment 418 that holds it snuggly to the channel.

The cold plates 400 are obvious in the side view and we mark the cold (404) and hot (405) liquid coolant channels that feed them at the top as well as the LHP 410 and its condenser lines 412 that get used to cool the processors which sit beneath them. The memory region of the card 413 is also called out as well as the device used to cool the DIMM modules, which employs an ordinary heat pipe 411 whose condenser is also thermally attached to a cold spreader. The balance of the components on the board that dissipate energy can be easily cooled using a copper mask that fits over them and is attached to them using a thermal interface material that is in turn attached to either the LHP of the heat pipe used to cool the DIMM modules. Or alternatively, the ground planes of the PCB can be thermally attached to the cold spreaders using a flexible sheet of copper made of shim stock that is soldered to the PCB and gets inserted between the cold spreader and the cold plate.

For this blade cooling solution to work, the thermal resistance of the split condenser defined by the cold spreader and the cold plates has to be adequate. In situations where the cards are spaced on 1 inch centers and are 18 inches deep, this solution provides 36 square inches of interface area between each of the cold spreaders and their cold plates. Based on earlier experiments this ought to handle at least 500 Watts of power per card. Sixteen of these devices packed into a chassis that is 7 inches (i.e. 4 U tall) will reject 8 KW, and in a 40 U tall rack cabinet this results in a cooling system that will handle 80 KW! This cooling solution also turns out to be much more efficient than any blade cooling solution that employs air and direct water cooling, both of which require additional power. The power densities here are high enough to suggest that the resulting water might even be hot enough to be sent directly to a cooling tower bypassing a systems water chiller. But, since we haven't built one of these units, we feel it is premature to make this claim, especially considering the fact that the split condenser here does not employ counter-flow principles like the unit we are about to describe.

In general, split condensers are not as efficient as the direct liquid cooled condenser design that we terminate this disclosure with. When working with them, one becomes aware of the fact that raising the temperature of the output flow is a non-trivial exercise. What makes it difficult to raise the temperature of the output flow from a water-cooled condenser, be it direct or indirectly (i.e. split condenser) cooled is the fact that for any design that employs heavy copper plates to exchange energy there are thermal conduction shorts that the plates enable which takes heat out of the hot side of the condenser and exchanges it with the cold side, reducing the delta T across the condenser and reducing the temperature of the effluent. The only way to eliminate this problem is to isolate the hot and cold sides of the condenser from each other. The design in FIG. 22 does precisely this.

FIG. 22 depicts a split condenser designed to sit behind a rack mount chassis inside of a rack cabinet. The cold plates 500 and 501 in this oblique 3D view may extend from the bottom of the rack cabinet to the top or over a more limited region that gets repeated at intervals to control the amount of heating that each section of cold plates needs to handle, making it possible to adjust flow rates and resistance to flow in such a manner that the maximum amount of heat gets transferred per Watt of energy expended pumping coolant through the cold plates and back out to either a chiller or cooling tower. In FIG. 22 we see a pair of cold spreaders 508 and 509 that are shown in different stages of being brought into their final mating station as the rack mount chassis or blade that they are attached to is inserted into rack cabinet or blade chassis. Neither the rack mount chassis or the blade or for that matter the structure that holds them in place behind the rack mount chassis or blade, is drawn.

The cold plates 500 and 501 may be created from extrusions, as depicted, that internally contain channels through which a coolant flows. In this case we show five such channels, but the number as well as the thickness of the channels is not to be inferred from these drawings. In this particular exemplary embodiment, five rectangular channels that conduct the coolant being used to cool the cold plate. The precise shape or number of channels is not important, but the material needs to be a good thermal conductor such as aluminum. The cold plates are mounted vertically inside of the rack cabinet with their secondary axis parallel to the direction that rack chassis take during their insertion into the rack cabinets. This makes it possible for their cold spreaders 508 and 509 to slip in over the cold plates 500 and 501 as a chassis is inserted.

Cold spreaders that have larger widths than those drawn that were modeled for 1 U rack mount chassis can be created in situations where the vertical extension of the chassis or blade being cooled is large. There is also no limitation on the number of cold plates and spreaders that may be mounted parallel to each other behind the chassis or blade held within a rack cabinet or blade enclosure, provided that space is left for other things to connect up to the chassis or blade, which in the case of a blade is at least a horizontally oriented PCB called a backplane. Creating a cold spreader that is wider than those shown here, but not as wide as the chassis or blade it is attached to is tall, makes it possible to increase the contact area of the cold spreader and cold plates, as does creating cold plates and cold spreaders that extend deeper into a rack cabinet or blade chassis. This design is not limited to just the two types of electronic enclosures just mentioned. In the case of COTS systems such as PICMG systems, these split condensers could easily be deployed just as easily for PICMG processor cards as they are employed here for blades. Increasing the contact are of the cold spreaders and cold plates makes it possible to cool devices which rejected very large amounts of energy. Alternatively, by taking advantage of the fact that LHP evaporators may be ganged together it makes it possible to cool a plurality of processors connected to a single split condenser whose contact area is large.

FIG. 23 call out more details in the design. Some provision must be made for holding the two channels at a precise distance from each other so that when finally clamped together, the make good thermal contact with the cold plates across their entire contact area. The mechanism that provides this separation at one end of the cold spreader is a bolt, sleeve and nut combination, 504. When the device is clamped (from the other end) this bolt keeps the end it is attached to from separating.

The upper portion of FIG. 23 is a downward looking view (what you would see looking down inside of a rack cabinet) that clearly shows the nature of the extrusions and their channels. The vapor in this particular exemplary embodiment arrives in LHP condenser pipe 502, and then proceeds to go all the way to the end of the top channel (in the bottom half of FIG. 22) before turning around and making thermal contact with its channel. The implications for this arrangement are that the channel carrying coolant labeled 507 will end up being in thermal contact with the hottest vapor coming off of the LHP evaporator, therefore it must be the last channel in the sequence, if our goal is to produce hot coolant. The liquid coolant channels within the extrusions are to be set up so that coolant flows sequentially through them, starting on one side and ending up on the other, in this case starting in channel 506 and ending up in 507, after passing through all of the intermediary channels one by one. Starting at the cold end with the LHP condenser line 503 that returns the condensed liquid vapor to the LHP evaporator, we discover that it makes thermal contact with channel 506 to begin with. What this means, is that starting with channel 506, and progressing towards channel 505, each channel gets progressively hotter as the coolant moves down the line. When it reaches the end, it shifts from the bottom extrusion to the top and then progresses down that line of channels until it finally arrives at 507, the end. Note that we employ a serpentine shaped condenser line on both sides of the cold spreader whose job it is to "spend some time" exchanging heat sequentially with each of the cold plate channels it passes over, whose temperature decreases as the vapor cools making it possible in some instances to sub-cool the primary coolant. We employ a pair of extrusions, for the simple reason that to maximize contact area it pays to employ a male female arrangement, and since in this case we are also attempting to maximize temperatures by also providing a counter-flow heat exchange situation it helps if we can at least divide the cold plate into two separate cold plates that are not in thermal contact with each other, as this is the only way we can be sure to minimize thermal shorts that bypass our cooling solution and bring down the temperature of our effluent. In an even more aggressive exemplary embodiment that we have chosen not to detail here, the cooling channels that the cold plates are made up of could be thermally isolated from each other, employing a material that is not a good conductor of heat to sit between each of the channels. However, one suspects that no matter how good a job one does with this approach to counter-flow cooling, the best performance and the smallest thermal resistance will ultimately be obtained using a device yet to be discussed which employs direct liquid cooling of a counter flow heat exchanger. This is not intended to demean the value of this exemplary embodiment. There are situations where it becomes difficult to employ liquid quick disconnects. This exemplary embodiment provides a solution for that combines efficiency with performance and can be scaled to reject very large quantities of heat more efficiently than the heroic devices being invented that use a combination of blowers, pumps and compressors mounted inside of rack cabinets.

FIG. 24 demonstrates how two different LHP types, one with a cylindrical evaporator and another with a box shaped one can be mounted on processors and reject their heat to a condenser whose fins 606 and base 605, they share.

Starting with the liquid return line 601 of the left hand cylindrical LHP, we observe that both LHPs employ serpentine shaped condenser lines 604 that get clamped to the base 605 of an air-cooled heat exchanger whose plurality of fins 606 can also be seen. The serpentine condenser line gets clamped to the base plate 605 by pressure exerted against it by a clamping plate and screws that connect to the plurality of studs, one of which, 603, is called out and all of which are mounted into the base plate 605. An exploded view of the clamping plate can be found in FIG. 4. Each of the serpentine condenser lines start off as a vapor feed line 602 that takes the hot vapor coming off the LHP Evaporator's wick and carries the vapor to its respective serpentine condenser sections. The liquid return inlets of both LHPs include a compensation chamber 608 that essentially is a hollow area inside of the evaporator proper that gets used to store liquid that gets forced to the evaporator as the LHP heats up. The remainder of the evaporator contains the wick and the vapor exhaust ports, neither of which can be seen here, as no claims are being made in this document for the details that pertain to the internal details of LHP evaporators. The region of the evaporator shell near where the wick resides is called out by 611.

In the case of the cylindrical evaporator on the left hand side, a copper heat spreader 610 that sits between the device being cooled and the thermally active region of the wick gets employed to transfer heat between the device being cooled, whose socket 607 is called out. The sealed tubes that get used during manufacture to fill the LHPs with working fluid 600 are also called out. The evaporator on the right hand side is basically flat and gets used in situations where the pressure of the working fluid at temperature is roughly equal to atmospheric pressure. Because it can be made of rather thin sheet metal, the thermal resistance between its wick and the heat spreader of the CPU beneath it is less than the cylindrical design on the left. The right hand evaporator is held in contact with the CPU being cooled using a clamp 609. The cylindrical evaporator on the left hand side is designed to work with more volatile working fluids, which become active under smaller heat loads and whose pressure in the operating temperature range of most CPUs and GPUs is large enough to require a strong shell to contain it.

FIGS. 25 and 26 depict heat spreaders that are designed to interface a cylindrical evaporator with the device being cooled. The evaporators in these pictures employed a working fluid whose pressure runs between 10 and 20 atmospheres when used to cool devices rejecting energy at 65 to 100 C. The high pressures require that the evaporator be made of a strong material. The cylindrical structure 171 is ideal for containing high pressure gases. The diameter of the cylindrical shells 171 employed is only 0.3 inches, which is just slightly larger than the tubing used to make standard heat pipes. However the condenser tubing (173 and 174) is only 0.1 inches, which is much smaller than the ¼ inch tubing used in heat pipes. This is partly a result of the fact that higher pressure working fluids have higher densities, making it possible for them to carry the same heat as water using much lower flow rates. The evaporators seen here were made of Nickel and interfaced to copper heat spreaders using solder. Two heat spreaders 176 are shown, one that employs a single evaporator (FIG. 25) and another (FIG. 26) that contains two. When cooling a 1" square device, it is actually possible to mount three evaporator shells on a single heat spreader to obtain a maximum heat rejection of three times that available from a single evaporator tube.

The peak power that this design ought to reject working with a 100° C. semiconductor device is close to 1000 Watts—25 times the amount of heat being rejected by ordinary heat pipes that take up roughly the same amount of headroom in a chassis, and whose outside diameter is actually greater than that of the condenser pipes used here!

The items called out in the two figures are: clearance holes 170 for the motherboard spring loaded clamping bolts, the return liquid intake line 174, the region 175 of the evaporator where the return fluid gets stored internally and which is called the compensation chamber, the shell 171 itself, the region of the shell 172 where the internal wick converts liquid to gas and produces the pressure gradient that drives the cooling loop and the condenser exhaust port (173). To reduce thermal resistance between the evaporator wick internal to the evaporator shell and the device being cooled, a shoulder 177 was introduced in the heat spreader. In addition, the cavity 178 that was milled into the heat spreader was also designed to minimize thermal resistance by reducing the amount of copper between the bottom of the shell and the bottom of the heat spreader as much as possible.

The only difference between the heat spreader shown in FIG. 26 and that already examined, is the fact that the spreader in FIG. 26 has two evaporators soldered to it. Otherwise, the numbers that are called out here are identical to those called out in FIG. 25.

FIGS. 27, 28 and 29 are for a direct liquid cooled counter flow heat exchanger that was designed to make further reductions in LHP thermal resistance. At the time that we designed these devices, our goal shifted from simply cooling hot processors, to rejecting a secondary coolant that was as hot as possible, and certainly much hotter than the air that is typically rejected by rack mount chassis and rack cabinets into data center rooms. Using this device overall LHP thermal resistances of 0.15° C./Watt were achieved, making it possible to cool a 100 Watt CPU and maintain a die temperature as little as 65° C. using warm intake water whose temperature was 30° C., while producing output water as hot as 50° C. A similar device that also employed a coolant jacketed serpentine heat exchanger was able to cool a device rejecting 320 Watts operating at higher temperatures. LHPs and LHPLs that satisfy this criterion are capable of operating in climates as hot and humid as Atlanta Ga. driving evaporative cooling towers, whose output hits 30° C. on the hottest most humid days of the year.

The exact form of the liquid cooled condenser exchanger is not critical. The liquid jacket can be as simple as a pipe that encloses the condenser line. The distance that the condenser pipe travels while encased in a water jacket is. And, when the goal switches from simply condensing the primary vapor to condensing it while at the same time producing the hottest secondary coolant, then other things become important as well. These include preventing heat leaks across the condenser while at the same time making it possible for the smallest secondary coolant flows to be fully taken advantage of. All three criterion can be met in LHP and LHPL condensers making LHPs and LHPLs probably the best devices available for not only efficiently transferring energy off hot running semiconductor devices but also producing secondary coolant flows whose temperatures are as hot as possibly can be obtained.

FIG. 28 shows what the assembled unit looks like. This particular exemplary embodiment was made of two pieces of plastic, 180 and 181, that were machined and attach together using 9 screws that passed through the upper piece of plastic 180 and engaged threaded holes in 181. The orientation of the devices is not critical, provided that the liquid is flown through the channel 184 (FIG. 27) in a counter flow manner in which the hot vapor arrives at the end of the heat exchanger opposite the point where the hot liquid return is situated. In both figures, we assume that 186 is the vapor input line, which makes 182 to hot water return. The chilled (but possibly warm in summer months when Free Cooling is being used) coolant enters the heat exchanger from the opposite side through pipe 183 near the point where the condensed primary coolant 185 returns to the LHP evaporator.

The ability of the LHP evaporator to accomplish the three critical tasks starts with their ability to drive primary coolants through long lengths of condenser tubing making it possible to employ large heat contact areas between the primary and secondary working fluids. Making the condenser jacket out of a thermal insulator solves the second problem. The third problem, making it possible to get good thermal conduction between the primary and secondary coolants even when the secondary coolant velocity has been reduced, is made possible in our case by the use of a helically wound device that we thermally attach to the condenser pipe which is made of a thermally conducting material that may take the form of a wire or foil that has been helically wound about the condenser pipe and is thermally attached to it. Adding this helical shape to the condenser pipe doubles its area while at the same time forcing the liquid to take a much longer helical shaped path through the heat exchanger. In addition, it breaks up boundary layers that inhibit heat conduction when a fluid is simply allowed to flow along a pipe. The net effect on the ability of the device to provide adequate condensation while at the same time employing liquid (i.e. water) coolant flow rates as low 1 CC/sec, is large and plays a crucial role in decreasing the overall thermal resistance of LHPs and LHPLs.

A critical person might want to know what is so different between this situation and the one where direct water-cooling is used to cool a CPU, ignoring all the energy wasted in pumping water. After all, now that we have efficiently gathered energy off of the device being cooled, the next thing we are doing is using it to do the same thing that direct water cooling does, which is to heat water. As was the case with the LHP wick, whose wick has a huge internal contact area, the critical aspect that makes efficient heat transfer possible at the condenser end of LHP and LHPL devices, is the area that is available to carry out the transfer, with the devices that have the largest contact areas, resulting in the smallest flow velocities and hence, the smallest loss of energy to devices that enable high speed flows. It turns out that the effective heat exchange area of the condensers pictured in FIGS. 27,28 and 29 is around 4 square inches. Employing a helical foil or wire doubles the area to around 8 square inches. The typical heat exchanger that used in direct liquid cooled CPU heat exchangers employ a liquid that is directed at a surface whose area is around one square inch, which might get doubled to two, using bumps. While this provides us with a four to one advantage, the actual advantage when it comes to producing a coolant that is heated is actually greater because in our case the liquid has to pass from one end to the other of the condenser line, and at each station along this path, the temperature of the vapor that is heating the secondary coolant rises, whereas in the case of a silicon die being cooled by exposure to a heat spreader that is in turn being cooled by water, the spreader itself and mixing within the plenum opposite the contact surface end up providing thermal energy short circuits as well as recirculation within the flow itself. All of which makes it difficult to produce a liquid coolant whose delta T across the inlet and outlet is large. The corollary to the situation where the delta T is reduced, is the velocity (and the energy put into it) needs to be increased.

FIG. 29 shows alternate exemplary embodiments of this design that have liquid coolant inlet and outlet ports (182 and 183) in locations that make feasible many different ways to employ these devices in semiconductor cooling situations.

FIG. 30 is an oblique 3D diagram of a specific exemplary embodiment of a very efficient method for cooling electronic devices enclosed in an electronic enclosure that has direct access to a chilled liquid coolant that implements one of the general claims made by the disclosure. The electronic enclosure drawn happens to be a 1 U rack mount chassis, but may be any electronic enclosure with direct access to a chilled liquid manifold. The specific implementation drawn here employs a particular method of delivering chilled coolant to the electronic enclosure but any method that suffices to deliver coolant to the enclosure will also work. The main features of the exemplary embodiment include:

1) The use of energy efficient passive devices of any type, including LHPs, LHPLs and ordinary heat pipes to remove the primary heat load from the devices rejecting it and to deliver this heat load to one or more efficient direct liquid cooled heat exchangers.
2) A method for removing the ancillary heat load and transferring this heat load directly to a chilled liquid, that may employ one or more methods including combinations thereof, including direct liquid cooled closed loop air circulation, passive connections between the ancillary components and a chilled liquid cold source such as a cold plate, chilled liquid cold plates in contact with PCBs enclosed by the enclosure and circulation of air within the chassis in a closed loop that does not involve the use of a chilled liquid air heat exchanger. The last method was specifically included in the list of ancillary methods to allow distributed cold plates within the chassis to directly cool the PCBs that reject most of the ancillary heat (outside of the primary loads) including motherboards and power supplies while at the same time employing circulating air within the chassis to gather up the remainder of this heat and allow it to be inexpensively exchanged with the PCBs being cooled by cold plates, which just happen to contain a lot of copper distributed over large surface areas.

The specific exemplary embodiment in FIG. 30 is for a "sealed 1 U chassis" that employs a pair of LHP evaporators 214 that are cooled by a pair of counter flow LHP heat exchangers 224 previously described, to cool a pair of processors. This particular exemplary embodiment is similar to that shown in FIG. 18, with the exception that we have now replaced the split condensers (that employ permanently connected liquid connections) with a liquid cooling system in which we employ quick disconnects 205 and 208 (note we are calling out two of the four liquid feed lines and are using the same numbers we previously did for the hot and cold chilled liquid lines to now point to the quick disconnects that they are attached to. The quick disconnects happen to be female components, but they could just as easily have been male. They protrude into a small optional duct (not shown) that surrounds the main liquid feed mains and employs the same or a similar chassis to duct sealing arrangement as was previously employed with the negative pressure air duct. Within the duct sits a mating device that in this case happens to contain four male interconnects as well as a pair of guide holes that interface the guide pins 225 (one of which is labeled) seen here. This method of using pins that get larger as they expand into a guide hole for automatically connecting together couplings that carry liquids is similar to the ones employed in computers to align sockets that need to accurately mate. The purpose of this optional duct or shield 228, though is quite different. Enclosing the main liquid feed lines in a sealed duct and then avoiding the use of internal connections within the rack mount chassis itself, greatly reduces the possibility of liquid leaks within a chassis that may also be receiving electric power at 110 AC, 240 AC or 300 VDC power. The crushable seal 227 that makes contact with the duct can also be seen here.

Beneath the LHP counter flow heat exchangers can be seen the fins 209 of a liquid cooled air heat exchanger. The liquid that feeds the air heat exchanger in this exemplary embodiment just happens to come from a distribution block 226 that surrounds and contains the heat exchangers and includes a liquid cooled base plate that is thermally attached to the fins. The liquid that cools the air heat exchanger does not have to be shared with the heat exchangers and the precise order in which the liquids that cool the LHPs and the air get applied, is up to the engineer designing the system and the inclusion of other methods, which such as a method for bleeding air at a particular relative humidity into the rack mount chassis. Another pair of lines could have also been employed to supply the liquid assisted air heat exchanger or two of the four lines in FIG. 30 could have been split within the chassis and used to cool the primary load LHP heat exchangers while the other two were employed to cool the air heat exchanger.

This method uses a similar technique described in the exemplary embodiment in FIG. 18 to handle the secondary heat load, which is to circulate air within the chassis proper. The large arrows in FIG. 30 display the path taken by the closed loop air-cooling circuit employed. The actual path employed is not fixed. Any path that returns cooling air that has been heated by the secondary load, back to the liquid assisted air heat exchanger inlets, will suffice.

What is different about the method is its use of direct liquid cooling of the primary LHPs or LHPLs along with the fact that it can combine direct liquid cooled air heat exchangers, cold plates and air circulating without the use of liquid assisted air heat exchangers. In the exemplary embodiment displayed in FIG. 30, the secondary heat load is being picked up by a closed loop sealed air flow that stays within the chassis that passes beneath the LHP heat exchangers before being accelerated by a pair of fans 216 (one of which is called out) that could just as easily been one or more blowers before passing over a line of hard disks that could just as easily been located at the front of the chassis or omitted altogether and under and over the motherboard before turning the corner defined by the baffle 217 on the left hand side of the chassis interior and then passing through the power supply 218 where it gets accelerated again before reaching the entry plenum of the liquid assisted air heat exchanger that sits beneath the LHP primary load heat exchangers and then being sucked up again by the cooling fans that are the primary drivers of this closed loop cooling circuit. The intention here is to seal the chassis, using a positive pressure technique that slowly bleeds dry air into the chassis when the temperature of condensing surfaces within the chassis are below the relative humidity of the air in the room. In poorly managed data centers, up to 10% of all energy gets devoted to condensing and then humidifying the airflow. This is done to make the data center more convenient for humans and to reduce ESD. It turns out that in well designed and grounded circuits, such as those employed within rack mounted chassis, the ESD requirement has now been eliminated. However, care still has to be taken not to condense water vapor out within the chassis.

The two things that make this method so extraordinarily energy efficient are the very low thermal resistance of the LHP primary heat load cooling mechanism combined with an efficient as possible approach to recovering the secondary heat load. The latter has been greatly improved over other methods that combine direct chilled liquid cooling of the primary load (which is two orders of magnitude less efficient than the passive techniques employed here) with circulating air, by minimizing the energy required to circulate the air and also by employing optional PCB cold plates where possible to minimize the amount of air-cooling required in addition to keeping the length of the path used by the closed loop air circuit, much smaller than other solutions which often take the air on excursions that are a few to many meters in length.

FIG. 31 demonstrates how rack mounted chassis 700 that are being serviced by ducts 702 that provide either negative pressure air or chilled liquid manifolds can be employed to cool a plurality of rack mount chassis installed in racks or possibly cabinets. The rectangles labeled 700 in the grouping in the upper left corner represent four rack cabinets or open racks containing rack mount chassis that employ seals 701 that connect them to the duct 702 employed to provide these cooling services. This particular implementation uses a common service duct to handle four groups of rack mount chassis. The potential here is to be cooling 50 and 80 KW per rack cabinet or open rack, making it possible for each of these service ducts to have to provide as much as 300 KW in power while rejecting roughly the same amount of energy to a liquid flow. A gram of water heated up 20° C. can carry 20*4.184=83.7 Joules of energy. Dividing 300,000 Joules/sec by 83.7 reveals that it takes 3584 grams per second of water, or 3.58 Liters per second which is equal to 0.96 gallons per second to carry off this much heat. However, the delta T that we used here, 20° C., is really quite large, and could only be achieved using the LHPs we describe in this disclosure that employ very efficient counter-flow heat exchangers. For any other method, the typical delta T would be around 5° C., which would increase the water flow rate needed to service a group of four racks up to 4 gallons per second. For the grouping shown below a delta T of only 5° C. would result in a flow rate of 32 gallons per second or 1920 GPM. When you start to deal with flow rates of this magnitude, it becomes necessary to become water supply concentric, which is what our approach to creating this network of ducts is.

FIG. 32 demonstrates how a cooling tower 807 can be hooked up directly to a data center, whose data center room 801 contains a plurality of rack cabinets 808 is sending chilled water to the cooling tower through a pipe network 802 whose pipes have been insulated both going to and coming from the cooling tower that includes a pump 804 that is driven by an electric motor 803. The precise manner in which the chilled water and the connections to any such cooling tower are normally created by architects and engineers who are experts in the art. This drawing is just an exemplary embodiment of a way that the author believes such a system could be set up. The cooling tower may or may not need a cooling fan 806 driven by a motor 805, depending on its architecture and size, but one has been provided in this schematic presentation. And it may take one or more pumps in the system to move the chilled and heated water about along with other devices that might include tanks and other devices used to process water. The chilled water that results leaves through a network of insulated pipes 800 and returns to the data center room and its rack cabinets 808.

FIG. 33 shows four different rack cabinets 811 in different orientations. The one in the upper right corner employs six fans in its top panel to evacuate the air from the cabinet, which can be provided to this "fan tray" by an internal duct. The upper left cabinet is pictured with its door 812 closed, revealing four large fans 813 that protrude from it two inches. The top panel for this unit 810 is also called out. The unit on the lower right, has a lead line 808 that is intended to point to the entire unit, to remain consistent with FIGS. 32, 33 and 34 and like the unit on the lower left, it also provides a view of the fans 813 and the duct 814 that they sit on as well the door 812. The unit in the lower right hand corner provides a view of the rack mount chassis 815 within the cabinet. The duct that is sealed to them 814 can now be clearly seen.

FIG. 34 is a schematic representation of a primary closed loop system 900 that uses a split condenser. A processor 902 or other device (not necessarily restricted to an electric device) is thermally attached to an evaporator 904. A hot working fluid 906 exits the evaporator and travels to a condenser 908 via a first line 910. When the fluid 906 has moved through the condenser 908, the fluid 906 returns to the evaporator 904 via a second line 912. The condenser 908 cools the fluid 906 to create a phase change in the fluid 906 from gas to liquid. Within the evaporator 904, the fluid 906 undergoes a phase change from liquid to gas. A plurality of compensation chambers 914 may be included in the first line 910. In the embodiment illustrated, the evaporator 904 includes a capillary pump 920.

In an embodiment where the working fluid 906 is single phase gas, an optional pump 940 is required to reduce the pressure of the gas in the first line which reduces the pressure of the gas (working fluid vapor) in the evaporator thereby reducing the boiling point temperature of the working fluid at high power densities.

FIG. 35 is an exemplary embodiment of a DIMM module cooler. It consists of a metal heat conducting channel 830 preferably made of copper or aluminum, DIMM modules 836 (four of which are drawn but many more of which could be employed), that each contain a pair of memory chips 838 that sit on a small printed circuit board 833 and are surrounded by heat spreaders 835 all of which plug into sockets 834 that sit on a motherboard 832. A soft sponge like thermal conducting material 831 is situated between the inverted channel 830 and the motherboard or PCB that the DIMM modules are mounted on and is also employed to conduct heat between the DIMM modules and the channel and is situated just above the heat spreaders of the modules 835. This solution can be improved upon in cases where the modules reject more heat than the motherboard or PCB can accept by thermally attaching heat sinks to the top and sides of the channels or by thermally attaching either heat pipes or LHPLs to the top surface of the channel.

I claim:

1. A cooling device for cooling a plurality of heat rejecting components and a plurality of other components, the cooling device comprising:
   an enclosure housing enclosing the plurality of heat rejecting components and the plurality of other components;
   an external heat rejection device including an external coolant that transfers primary heat from a primary cooling system and secondary heat from a secondary cooling system to an environment outside of the enclosure;
   the primary cooling system including a loop heat pipe like (LHPL) device, the primary cooling system cooling a primary heat rejecting component, wherein the primary heat rejecting component is one of the plurality of heat rejecting components;
   the LHPL device includes
      an evaporator module,
      a condenser module,
      a vapor line,
      a liquid return line, and
      a working fluid having a liquid phase and a vapor phase, wherein the primary heat produced by the primary heat rejecting component being cooled causes the working fluid in the evaporator module to change from the liquid phase to the vapor phase, the vapor phase leaves the evaporator module passing through the vapor line and into the condenser module where the working fluid releases the primary heat absorbed in the evaporator module and returns to the liquid phase, the liquid phase then leaves the condenser module passing through the liquid return line and the working fluid returning to the evaporator module;

the evaporator module includes
  a component-evaporator heat spreader,
  an evaporator body, and
  an evaporator-component clamping means,
  wherein the component-evaporator heat spreader is clamped to the primary heat rejecting component providing thermal contact to transfer the primary heat produced by the primary heat rejecting component being cooled to the evaporator body by reducing the thermal resistance between the primary heat rejecting component and the evaporator body, the evaporator body comprises
  an evaporator outer shell,
  a working fluid inlet port,
  a compensation chamber,
  a working fluid exit port, and
  an evaporator wick having vapor escape channels,
  wherein the evaporator body receives the working fluid through the working fluid inlet port where the working fluid enters the compensation chamber located within the evaporator body before passing by capillary action into the evaporator wick where the working fluid absorbs the primary heat being rejected by the primary heat rejecting component causing the liquid phase of the working fluid to change the vapor phase that carries the primary heat produced by the primary heat rejecting component out of the evaporator wick through the vapor escape channels into the working fluid exit port;

the condenser module includes
  a condenser coolant inlet,
  a condenser coolant exit,
  a condenser condensation channel,
  a condensation channel working fluid inlet,
  a condensation channel working fluid exit, and
  a condensation channel-coolant thermal interface further comprises a coolant passageway,
  wherein the working fluid enters the condensation channel through the condensation channel working fluid inlet in the vapor phase, the working fluid changes phase in the condensation channel from the vapor phase back to the liquid phase and leaves the condensation channel through the condensation channel working fluid exit, delivering the primary heat produced by the primary heat rejecting component that was temporarily stored as heat of evaporation within the vapor phase to the external coolant which enters the condenser module through the condenser coolant inlet where the external coolant passes into the coolant passageway, the external coolant then carries away the primary heat produced by the primary heat rejecting component by exiting out of the coolant passageway through the condenser coolant exit;

the secondary cooling system including a secondary coolant, the secondary cooling system cooling a secondary heat rejecting component, wherein the secondary heat rejecting component is one of the plurality of other components;

the secondary cooling system includes
  an air cooled finned heat exchanger that is in thermal contact with the secondary heat rejecting component, and
  a rotary electric device for directing air across the air cooled finned heat exchanger and the secondary heat rejecting component to convection cool of the secondary heat rejecting component,
  wherein the secondary heat produced by the secondary heat rejecting component is released to the secondary coolant, the secondary coolant releases the secondary heat to the air cooled finned heat exchanger, and the air cooled finned heat exchanger releases the secondary heat to the external coolant.

2. The device of claim 1 wherein a direction of flow of the working fluid in the condenser module is opposite a direction of flow of the external coolant.

3. The device of claim 1 wherein the condenser module includes the coolant passageway whereby a thermal resistance of the condenser module is not reduced by a reduction in temperature between the condenser coolant exit and the condenser coolant inlet caused by conduction of heat from the condenser coolant exit through the coolant passageway to the condenser coolant inlet.

* * * * *